(12) United States Patent
Regev et al.

(10) Patent No.: US 11,332,736 B2
(45) Date of Patent: May 17, 2022

(54) METHODS AND COMPOSITIONS FOR MULTIPLEXING SINGLE CELL AND SINGLE NUCLEI SEQUENCING

(71) Applicants: The Broad Institute, Inc., Cambridge, MA (US); Massachusetts Institute of Technology, Cambridge, MA (US)

(72) Inventors: Aviv Regev, Cambridge, MA (US); Orit Rozenblatt-Rosen, Cambridge, MA (US); Jellert Gaublomme, Cambridge, MA (US); Bo Li, Cambridge, MA (US); Kathryn Geiger-Schuller, Cambridge, MA (US); Pratiksha Thakore, Cambridge, MA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 2 days.

(21) Appl. No.: 16/770,380

(22) PCT Filed: Dec. 7, 2018

(86) PCT No.: PCT/US2018/064563
§ 371 (c)(1),
(2) Date: Jun. 5, 2020

(87) PCT Pub. No.: WO2019/113506
PCT Pub. Date: Jun. 13, 2019

(65) Prior Publication Data
US 2021/0171938 A1    Jun. 10, 2021

Related U.S. Application Data

(60) Provisional application No. 62/595,904, filed on Dec. 7, 2017, provisional application No. 62/751,489, filed
(Continued)

(51) Int. Cl.
*C12N 15/10*    (2006.01)

(52) U.S. Cl.
CPC ............... *C12N 15/1065* (2013.01)

(58) Field of Classification Search
CPC .................................. C12N 15/1065
See application file for complete search history.

(56) References Cited

U.S. PATENT DOCUMENTS

| 4,971,903 A | 11/1990 | Hyman |
| 5,202,231 A | 4/1993 | Drmanac et al. |
(Continued)

FOREIGN PATENT DOCUMENTS

| AU | 2015101792 A4 | 1/2016 |
| CA | 3028158 A1 | 12/2017 |
(Continued)

OTHER PUBLICATIONS

Cusanovich et al., Science 348 (6237), 910-914, May 7, 2015 (Year: 2015).*
(Continued)

*Primary Examiner* — Kaijiang Zhang
(74) *Attorney, Agent, or Firm* — Johnson, Marcou, Isaacs & Nix, LLC; F. Brent Nix, Esq.; Michael B. Scher, Esq.

(57) ABSTRACT

The present invention provides methods and tools for analyzing genetic interactions. The subject matter disclosed herein is generally directed to single cell genomics and proteomics. In one embodiment provided is a method of cell and nuclei hashing using sample barcodes. In another embodiment are method of performing genomewide CRISPR perturbation screens.

21 Claims, 19 Drawing Sheets
Specification includes a Sequence Listing.

Related U.S. Application Data on Oct. 26, 2018, provisional application No. 62/770,580, filed on Nov. 21, 2018.

(56) References Cited

U.S. PATENT DOCUMENTS

| | | |
|---|---|---|
| 5,210,015 A | 5/1993 | Gelfand et al. |
| 5,403,708 A | 4/1995 | Brennan et al. |
| 5,445,934 A | 8/1995 | Fodor et al. |
| 5,525,464 A | 6/1996 | Drmanac et al. |
| 5,547,839 A | 8/1996 | Dower et al. |
| 5,580,737 A | 12/1996 | Polisky et al. |
| 5,604,097 A | 2/1997 | Brenner |
| 5,636,400 A | 6/1997 | Young |
| 5,641,870 A | 6/1997 | Rinderknecht et al. |
| 5,660,985 A | 8/1997 | Pieken et al. |
| 5,695,934 A | 12/1997 | Brenner |
| 5,695,940 A | 12/1997 | Drmanac et al. |
| 5,795,782 A | 8/1998 | Church et al. |
| 5,846,719 A | 12/1998 | Brenner et al. |
| 5,863,722 A | 1/1999 | Brenner |
| 5,869,326 A | 2/1999 | Hofmann |
| 5,902,723 A | 5/1999 | Dower et al. |
| 6,138,077 A | 10/2000 | Brenner |
| 6,150,516 A | 11/2000 | Brenner et al. |
| 6,172,214 B1 | 1/2001 | Brenner |
| 6,172,218 B1 | 1/2001 | Brenner |
| 6,235,475 B1 | 5/2001 | Brenner et al. |
| 6,352,828 B1 | 3/2002 | Brenner |
| 7,041,481 B2 | 5/2006 | Anderson et al. |
| RE39,793 E | 8/2007 | Brenner |
| 7,393,665 B2 | 7/2008 | Brenner |
| 7,537,897 B2 | 5/2009 | Brenner et al. |
| 7,544,473 B2 | 6/2009 | Brenner |
| 7,708,949 B2 | 5/2010 | Stone et al. |
| RE41,780 E | 9/2010 | Anderson et al. |
| 8,003,312 B2 | 8/2011 | Krutzik et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,790,490 B2 | 10/2017 | Zhang et al. |
| 2004/0171156 A1 | 9/2004 | Hartley et al. |
| 2005/0172476 A1 | 8/2005 | Stone et al. |
| 2006/0163385 A1 | 7/2006 | Link et al. |
| 2007/0003442 A1 | 1/2007 | Link et al. |
| 2007/0184489 A1 | 8/2007 | Griffiths et al. |
| 2007/0195127 A1 | 8/2007 | Ahn et al. |
| 2008/0003142 A1 | 1/2008 | Link et al. |
| 2008/0014589 A1 | 1/2008 | Link et al. |
| 2008/0081330 A1 | 4/2008 | Kahvejian |
| 2009/0005254 A1 | 1/2009 | Griffiths et al. |
| 2009/0131543 A1 | 5/2009 | Weitz et al. |
| 2010/0002241 A1 | 1/2010 | Hirose et al. |
| 2010/0137163 A1 | 6/2010 | Link et al. |
| 2010/0172803 A1 | 7/2010 | Stone et al. |
| 2011/0265198 A1 | 10/2011 | Gregory et al. |
| 2012/0017290 A1 | 1/2012 | Cui et al. |
| 2012/0219947 A1 | 8/2012 | Yurkovetsky et al. |
| 2013/0236946 A1 | 9/2013 | Gouble |
| 2013/0337441 A1 | 12/2013 | Lohse |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0256595 A1 | 9/2014 | Link et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2015/0051088 A1 | 2/2015 | Kim |
| 2015/0184139 A1 | 7/2015 | Zhang et al. |
| 2015/0259674 A1 | 9/2015 | Steelman et al. |
| 2016/0060691 A1 | 3/2016 | Giresi et al. |
| 2016/0208323 A1 | 7/2016 | Bernstein et al. |
| 2016/0370266 A1 | 12/2016 | White et al. |
| 2017/0211142 A1 | 7/2017 | Smargon et al. |
| 2017/0349894 A1 | 12/2017 | Dahlman et al. |
| 2018/0112255 A1 | 4/2018 | Chen et al. |
| 2018/0251825 A1* | 9/2018 | Stoeckius ............ C12Q 1/6844 |
| 2018/0320224 A1 | 11/2018 | Gaublomme et al. |
| 2018/0341744 A1 | 11/2018 | Regev et al. |
| 2019/0085324 A1 | 3/2019 | Regev et al. |

FOREIGN PATENT DOCUMENTS

| | | |
|---|---|---|
| CN | 108513582 A | 9/2018 |
| EP | 0 404 097 A2 | 12/1990 |
| EP | 2 047 910 A2 | 4/2009 |
| EP | 2 771 468 B1 | 2/2015 |
| EP | 2 784 162 B1 | 4/2015 |
| EP | 2 764 103 B1 | 8/2015 |
| EP | 3 009 511 A2 | 4/2016 |
| WO | 93/11161 A1 | 6/1993 |
| WO | 93/23564 A1 | 11/1993 |
| WO | 96/39154 A1 | 12/1996 |
| WO | 97/03211 A1 | 1/1997 |
| WO | 97/49450 A1 | 12/1997 |
| WO | 98/13523 A1 | 4/1998 |
| WO | 98/28440 A1 | 7/1998 |
| WO | 98/52609 A1 | 11/1998 |
| WO | 01/89788 A2 | 11/2001 |
| WO | 2004/002627 A2 | 1/2004 |
| WO | 2004/091763 A2 | 10/2004 |
| WO | 2005/021151 A1 | 3/2005 |
| WO | 2006/040551 A2 | 4/2006 |
| WO | 2006/040554 A1 | 4/2006 |
| WO | 2006/096571 A2 | 9/2006 |
| WO | 2007/081385 A2 | 7/2007 |
| WO | 2007/089541 A2 | 8/2007 |
| WO | 2007/133710 A2 | 11/2007 |
| WO | 2008/063227 A2 | 5/2008 |
| WO | 2009/012418 A2 | 1/2009 |
| WO | 2010/056728 A1 | 5/2010 |
| WO | 2011/079176 A2 | 6/2011 |
| WO | 2012/106385 A2 | 8/2012 |
| WO | 2014/018423 A2 | 1/2014 |
| WO | 2014/047556 A1 | 3/2014 |
| WO | 2014/047561 A1 | 3/2014 |
| WO | 2014/085802 A1 | 6/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/143157 A1 | 9/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |

(56) References Cited

FOREIGN PATENT DOCUMENTS

| | | |
|---|---|---|
| WO | 2014/204727 A1 | 12/2014 |
| WO | 2014/204728 A1 | 12/2014 |
| WO | 2014/204729 A1 | 12/2014 |
| WO | 2014/210353 A2 | 12/2014 |
| WO | 2015/050998 A2 | 4/2015 |
| WO | 2015/058052 A1 | 4/2015 |
| WO | 2015/070083 A1 | 5/2015 |
| WO | 2015/089351 A1 | 6/2015 |
| WO | 2015/089354 A1 | 6/2015 |
| WO | 2015/089364 A1 | 6/2015 |
| WO | 2015/089419 A2 | 6/2015 |
| WO | 2015/089427 A1 | 6/2015 |
| WO | 2015/089462 A1 | 6/2015 |
| WO | 2015/089465 A1 | 6/2015 |
| WO | 2015/089473 A1 | 6/2015 |
| WO | 2015/089486 A2 | 6/2015 |
| WO | 2015/130968 A2 | 9/2015 |
| WO | 2015188839 A2 | 12/2015 |
| WO | 2016/028682 A1 | 2/2016 |
| WO | 2016/040476 A1 | 3/2016 |
| WO | 2016/049024 A2 | 3/2016 |
| WO | 2016/049163 A2 | 3/2016 |
| WO | 2016/049251 A1 | 3/2016 |
| WO | 2016/049258 A2 | 3/2016 |
| WO | 2016/094867 A1 | 6/2016 |
| WO | 2016/094872 A1 | 6/2016 |
| WO | 2016/094874 A1 | 6/2016 |
| WO | 2016/094880 A1 | 6/2016 |
| WO | 2016/100974 A1 | 6/2016 |
| WO | 2016/106236 A1 | 6/2016 |
| WO | 2016/106244 A1 | 6/2016 |
| WO | 2016/149422 A1 | 9/2016 |
| WO | 2016/161516 A1 | 10/2016 |
| WO | 2016/168584 A1 | 10/2016 |
| WO | 2016/205749 A1 | 12/2016 |
| WO | 2016/205759 A1 | 12/2016 |
| WO | 2017/044893 A1 | 3/2017 |
| WO | 2017/070605 A1 | 4/2017 |
| WO | 2017/075292 A1 | 5/2017 |
| WO | 2017/075294 A1 | 5/2017 |
| WO | 2017075265 A1 | 5/2017 |
| WO | 2017/156336 A1 | 9/2017 |
| WO | 2017/161325 A1 | 9/2017 |
| WO | 2017/164936 A1 | 9/2017 |
| WO | 2017/219027 A1 | 12/2017 |
| WO | 2018/035250 A1 | 2/2018 |
| WO | 2018/170333 A1 | 9/2018 |
| WO | 2019/005866 A1 | 1/2019 |
| WO | 2019/113506 A1 | 6/2019 |

OTHER PUBLICATIONS

Zilionis et al., "Single-cell Barcoding and Sequencing Using Droplet Microfluidics", Nature Protocols, vol. 12, No. 1, Jan. 2017, 44-73.

Rosenberg et al., "Single-Cell Profiling of the Developing Mouse Brain and Spinal Cord with Split-Pool Barcoding", Science, vol. 360, No. 6385, Apr. 13, 2018, 8 pages.

Sanjana et al., "Improved Vectors and Genome-Wide Libraries for CRISPR Screening", Nature Methods, vol. 11, No. 8, Aug. 2014, 5 pages.

Satija et al., "Spatial Reconstruction of Single-Cell Gene Expression Data", Nature Biotechnology, vol. 33, No. 5, May 2015, 495-502.

Shalem et al., "Genome-Scale CRISPR-Cas9 Knockout Screening in Human Cells", Science, vol. 343, No. 6166, Jan. 3, 2014, 10 pages.

Shalem et al., "High-Throughput Functional Genomics Using CRISPR-Cas9", Nature Reviews Genetics, vol. 16, No. 5, May 2015, 28 pages.

Shendure et al., "Massively Parallel Genetics", Genetics, vol. 203, Jun. 2016, 617-619.

Smith et al., "Massively Parallel Decoding of Mammalian Regulatory Sequences Supports a Flexible Organizational Model", Nature Genetics, vol. 45, No. 9, Jul. 2013, 11 pages.

Stoeckius et al., "Cell Hashing with Barcoded Antibodies Enables Multiplexing and Doublet Detection for Single Cell Genomics", Genome Biology, vol. 19, No. 224, 2018, 12 pages.

Stoeckius et al., "Simultaneous Epitope and Transcriptome Measurement in Single Cells", Nature Methods, vol. 14, No. 9, Jul. 31, 2017, 10 pages.

Swiech et al., "In Vivo Interrogation of Gene Function in the Mammalian Brain Using CRISPR-Cas9", Nature Biotechnology, vol. 33, No. 1, Jan. 2015, 102-106.

Tanenbaum et al., "A Protein-Tagging System for Signal Amplification in Gene Expression and Fluorescence Imaging", Cell, vol. 159, Issue 3, Oct. 23, 2014, 635-646.

Tsumura et al., "Maintenance of Self-Renewal Ability of Mouse Embryonic Stem Cells in the Absence of DNA Methyltransferases Dnmt1, Dnmt3a and Dnmt3b", Genes Cells, vol. 11, No. 7, Jul. 2006, 805-814.

Vitak et al., "Sequencing Thousands of Single-Cell Genomes with Combinatorial Indexing", Nature Methods, vol. 14, No. 3, Mar. 2017, 19 pages.

Wang et al., "Genetic Screens in Human Cells Using the CRISPR/Cas9 System", Science, vol. 343, No. 6166., Jan. 3, 2014, 12 pages.

Wang et al., "Identification and Characterization of Essential Genes in the Human Genome", Science, vol. 350, No. 6264, Nov. 15, 2015, 1096-1101.

Wong et al., "Multiplexed Barcoded CRISPR-Cas9 Screening Enabled by CombiGEM", Proceedings of the National Academy of Sciences of the United States of America, vol. 113, No. 9, Mar. 1, 2016, 2544-2549.

Zheng et al., "Haplotyping Germline and Cancer Genomes with High-Throughput Linked-Read Sequencing", Nature Biotechnology, vol. 34, No. 3, Mar. 2016, 303-311.

The Broad Institute, Inc., International Preliminary Report on Patentability issued in International Application No. PCT/US2018/064553, dated Jun. 18, 2020, 9 pages.

The Broad Institute, Inc., International Preliminary Report on Patentability issued in International Application No. PCT/US2018/064563, dated Jun. 18, 2020, 11 pages.

The Broad Institute, Inc., International Search Report and Written Opinion issued in International Application No. PCT/US2018/064553, dated Feb. 26, 2019, 12 pages.

Adamson et al., "A Multiplexed Single-Cell CRISPR Screening Platform Enables Systematic Dissection of the Unfolded Protein Response", Cell, vol. 167, No. 7, Dec. 15, 2016, 42 pages.

Aguirre et al., "Genomic Copy Number Dictates a Gene-Independent Cell Response to CRISPR/Cas9 Targeting", Cancer Discovery, vol. 6, No. 8, Jun. 3, 2016, 914-929.

Amit et al., "Strategies to Discover Regulatory Circuits of the Mammalian Immune System", Nature Reviews Immunology, vol. 11, No. 12, Nov. 18, 2011, 14 pages.

Amit et al., "Unbiased Reconstruction of a Mammalian Transcriptional Network Mediating Pathogen Responses", Science, vol. 326, Issue 5950, Oct. 9, 2009, 257-263.

Anders et al., "Structural Basis of PAM-Dependent Target DNA Recognition by the Cas9 Endonuclease", Nature, vol. 513, No. 7519, Sep. 25, 2014, 22 pages.

Bandyopadhyay et al., "Rewiring of Genetic Networks in Response to DNA Damage", Science, vol. 330, No. 6009, Dec. 3, 2010, 9 pages.

Bassik et al., "A Systematic Mammalian Genetic Interaction Map Reveals Pathways Underlying Ricin Susceptibility", Cell, vol. 152, No. 4, Feb. 14, 2013, 28 pages.

Berger et al., "High-throughput Phenotyping of Lung Cancer Somatic Mutations", Cancer Cell, vol. 30, No. 2, Aug. 8, 2016, 31 pages.

Briner et al., "Guide RNA Functional Modules Direct Cas9 Activity and Orthogonality", Molecular Cell, vol. 56, Issue 2, Oct. 23, 2014, 7 pages.

Butler et al., "Integrating Single-cell Transcriptomic Data Across different Conditions, Technologies, and Species", Nature Biotechnology, vol. 36, No. 5, May 2018, 17 pages.

(56) References Cited

OTHER PUBLICATIONS

Cao et al., "Comprehensive Single Cell Transcriptional Profiling of a Multicellular Organism by Combinatorial Indexing", Available at: BioRxiv https://doi.org/10.1101/104844, Feb. 2, 2017, 35 pages.
Cao et al., "Comprehensive Single-cell Transcriptional Profiling of a Multicellular Organism", Science, vol. 357, No. 6352, Aug. 18, 2017, 7 pages.
Capaldi et al., "Structure and Function of a Transcriptional Network Activated by the MAPK Hog1", Nature Genetics, vol. 40, No. 11, Nov. 2008, 18 pages.
Chavez et al., "Highly Efficient Cas9-mediated Transcriptional Programming", Nature Methods, vol. 12, No. 4, Apr. 2015, 11 pages.
Chen et al., "Genome-Wide CRISPR Screen in a Mouse Model of Tumor Growth and Metastasis", Cell, vol. 160, No. 6, Mar. 12, 2015, 28 pages.
Datlinger et al., "Pooled CRISPR Screening with Single-cell Transcriptome Readout", Nature Methods, vol. 14, No. 3, Mar. 2017, 20 pages.
Dixit et al., "Perturb-Seq: Dissecting Molecular Circuits with Scalable Singe-Cell RNA Profiling of Pooled Genetic Screens", Cell, vol. 167, No. 6, Dec. 15, 2016, 32 pages.
Zheng et al., "Massively Parallel Digital Transcriptional Profiling of Single Cells", Nature Communications, vol. 8, No. 14049, Jan. 16, 2017, 12 pages.
Duan et al., "LINCS Canvas Browser: Interactive Web App to Query, Browse and Interrogate LINCS L1000 Gene Expression Signatures", Nucleic Acids Research, vol. 42, Issue W1, May 13, 2014, 13 pages.
Fan et al., "Combinatorial Labeling of Single Cells for Gene Expression Cytometry", Science, vol. 347, Issue 6222, Feb. 6, 2015, 10 pages.
Feldman et al., "Lentiviral Co-Packaging Mitigates the Effects of Intermolecular Recombination and Multiple Integrations in Pooled Genetic Screens", BioRxiv, Feb. 8, 2018, 6 pages.
Gehring et al., "Highly Multiplexed Single-Cell RNA-seq for Defining Cell Population and Transcriptional Spaces", Retrieved as : https://doi.org/10.1101/315333. on Jul. 25, 2020, May 5, 2018, 19 pages.
Gierahn et al., "Seq-Well: Portable, Low-Cost RNA Sequencing of Single Cells at High Throughput", Nature Methods, vol. 14, No. 4, Apr. 2017., 9 pages.
Gilbert et al., "CRISPR-Mediated Modular RNA-Guided Regulation of Transcription in Eukaryotes", Cell, vol. 154, No. 2, Jul. 18, 2013, 20 pages.
Gilbert et al., "Genome-Scale CRISPR-Mediated Control of Gene Repression and Activation", Cell, vol. 159, No. 3, Oct. 23, 2014, 647-661.
Haber et al., "Systematic Triple-Mutant Analysis Uncovers Functional Connectivity Between Pathways Involved in Chromosome Regulation", Cell, vol. 3, No. 6, Jun. 27, 2013, 2168-2178.
Habib et al., "Div-Seq: Single-Nucleus RNA-Seq Reveals Dynamics of Rare Adult Newborn Neurons", Science, vol. 353, No. 6302, Jul. 28, 2016, 925-928.
Habib et al., "Massively Parallel Single-Nucleus RNA-seq with DroNc-seq", Nature Methods, vol. 14, No. 10, Oct. 2017, 18 pages.
Hill et al., "On the design of CRISPR-based Single-Cell Molecular Screens", Nature Methods, vol. 15, No. 4, Apr. 2018, 22 pages.
Hughes et al., "Functional Discovery via a Compendium of Expression Profiles", Cell, vol. 102, Jul. 7, 2000, 109-126.
Jaitin et al., "Dissecting Immune Circuits by Linking CRISPR-Pooled Screens with Single-Cell RNA-Seq", Cell, vol. 167, No. 7, Dec. 15, 2016, 29 pages.
Kabadi et al., "Multiplex CRISPR/Cas9-Based Genome Engineering from a Single Lentiviral Vector", Nucleic Acids Research, vol. 42, No. 19, Aug. 13, 2014, 11 pages.
Kampmann et al., "Functional Genomics Platform for Pooled Screening and Generation of Mammalian Genetic Interaction Maps", Nature Protocols, vol. 9, No. 8, Aug. 2014, 48 pages.
Kang et al., "Multiplexed Droplet Single-cell RNA-sequencing using Natural Genetic Variation", Nature Biotechnology, vol. 36, No. 1, Jan. 2018, 89-94.
Kemmeren et al., "Largescale Genetic Perturbations Reveal Regulatory Networks and An Abundance of Gene-Specific Repressors", Cell, vol. 157, No. 3, Apr. 24, 2014, 740-752.
Klein et al., "Droplet Barcoding for Single-Cell Transcriptomics Applied to Embryonic Stem Cells", Cell, vol. 161, No. 5, May 21, 2015, 24 pages.
Konermann et al., "Genome-Scale Transcriptional Activation by an Engineered CRISPR-Cas9 Complex", Nature, vol. 517, No. 7536, Jan. 29, 2015, 583-588.
Lamb et al.,"The Connectivity Map: Using Gene-Expression Signatures to Connect Small Molecules, Genes, and Disease", Science, vol. 313, Issue 5795, Sep. 29, 2006, 1929-1935.
Liberali et al., "Single-Cell and Multivariate Approaches in Genetic Perturbation Screens", Nature Reviews Genetics, vol. 16, No. 1, Dec. 2, 2014, 15 pages.
Macosko et al., "Highly Parallel Genome-Wide Expression Profiling of Individual Cells Using Nanoliter Droplets", Cell, vol. 161, No. 5, May 21, 2015, 25 pages.
Melnikov et al., "Systematic Dissection and Optimization of Inducible Enhancers in Human Cells using a Massively Parallel Reporter Assay", Nature Biotechnology, vol. 30, Feb. 26, 2012, 9 pages.
Nagy et al., "Single-nucleus RNA Sequencing shows Convergent Evidence from Different Cell Types for Altered Synaptic Plasticity in Major Depressive Disorder", Retrieved from : https://doi.org/10.1101/384479 as on Jul. 25, 2020, Aug. 3, 2018, 37 pages.
Parnas et al., "A Genome-Wide CRISPR Screen in Primary Immune Cells to Dissect Regulatory Networks", Cell, vol. 162, No. 3, Jul. 30, 2015, 24 pages.
Picelli et al., "Full-Length RNA-Seq from Single Cells using Smart-seq2", Nature Protocols,vol. 9, No. 1, Jan. 2, 2014, 171-181.
Platt et al., "CRISPR-Cas9 Knockin Mice for Genome Editing and Cancer Modeling", Cell, vol. 159, No. 2, Oct. 9, 2014, 31 pages.
Rajagopal et al., "High-throughput Mapping of Regulatory DNA", Nature Biotechnology, vol. 34, No. 2, Feb. 2016, 22 pages.
Rosenberg et al., "Scaling Single Cell Transcriptomics Through Split Pool Barcoding", Available at:Bio Rxiv http://dx.doi.org/10.1101/105163, Feb. 2, 2017, 13 pages.
The Broad Institute, Inc., et al., "Notification of Transmittal of The International Search Report and the Written Opinion of the International Searching Authority, or the Declaration", PCT/US2018/064563, dated Feb. 26, 2019, 14 pages.

\* cited by examiner demuxEM

- Define $\Theta = (\theta_0, \theta_1, \ldots, \theta_n)$, $\sum_{i=0}^{n} \theta_i = 1$

- $\theta_0$ is the probability that a hashtag comes from background noise
  - $\theta_1, \ldots, \theta_n$ are the probabilities that a hashtag comes from a sample

- Define background distribution $$P = (p_1, \ldots, p_n), \sum_{i=1}^{n} p_i = 1$$

- Probability of generating a HTO from sample $i$:

$$P(HTO = i) = \theta_0 p_i + \theta_i$$

- Log likelihood function:

$$L(\Theta) = \sum_{i=1}^{n} c_i \log(\theta_0 p_i + \theta_i) + \log \frac{(\sum_{i=1}^{n} c_i)!}{\prod_{i=1}^{n} c_i!}$$

FIG. 3

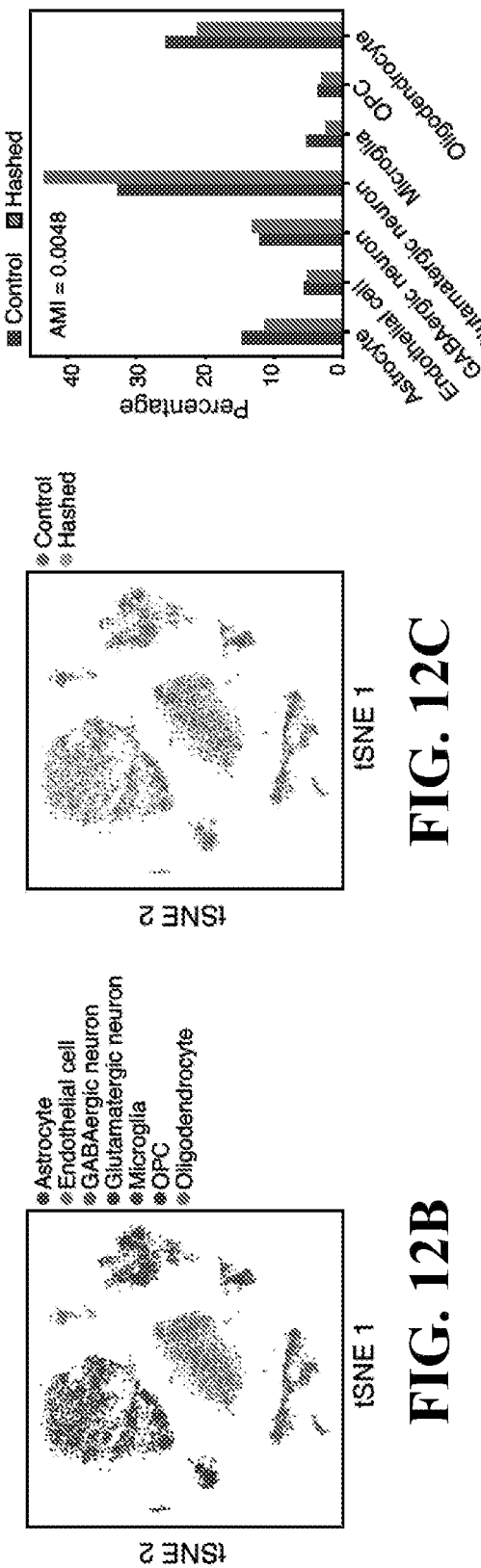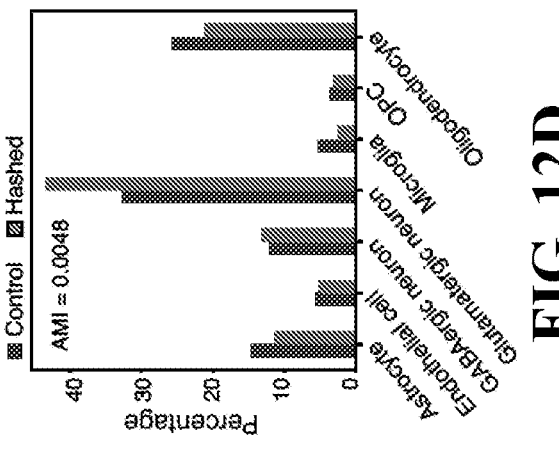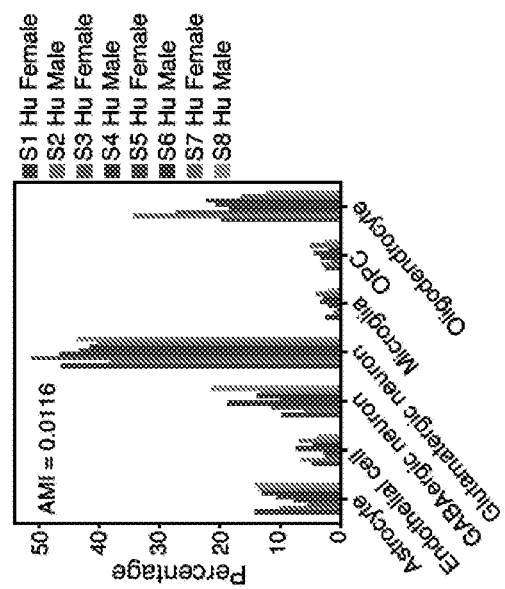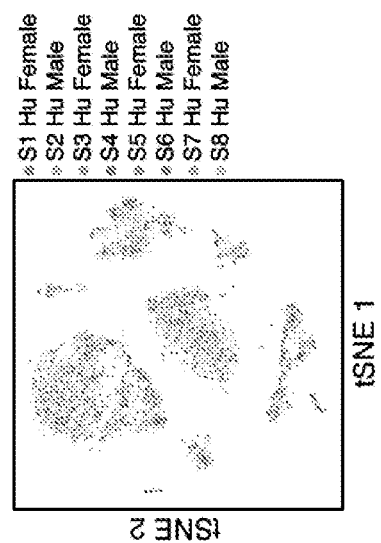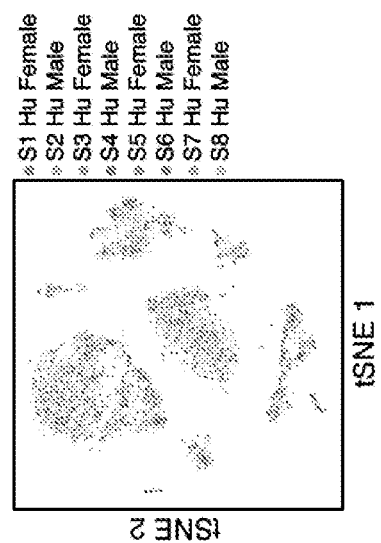
FIG. 12B  FIG. 12C  FIG. 12D
FIG. 12E  FIG. 12F  FIG. 12G

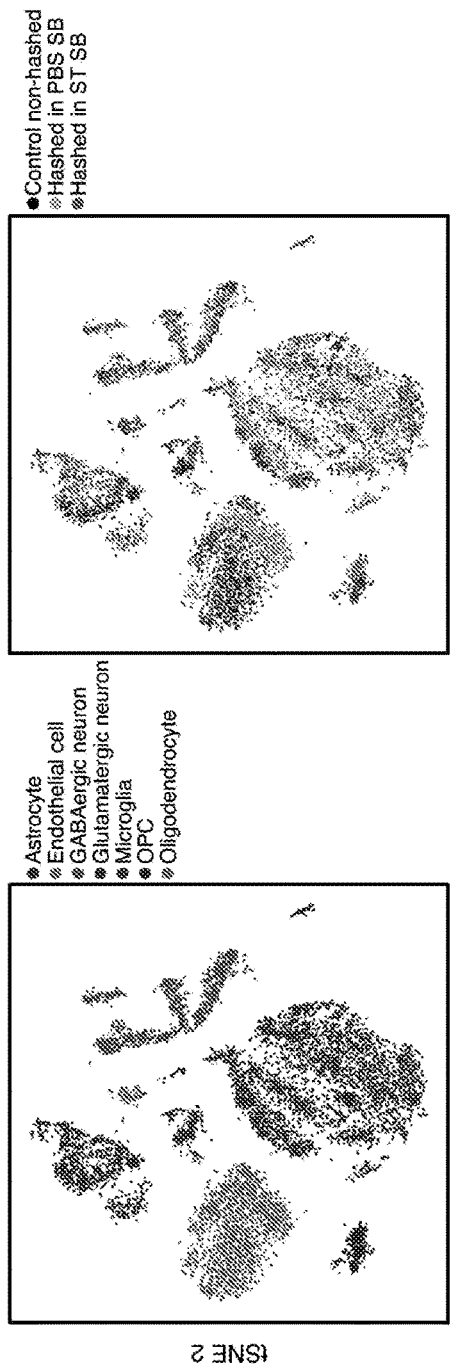
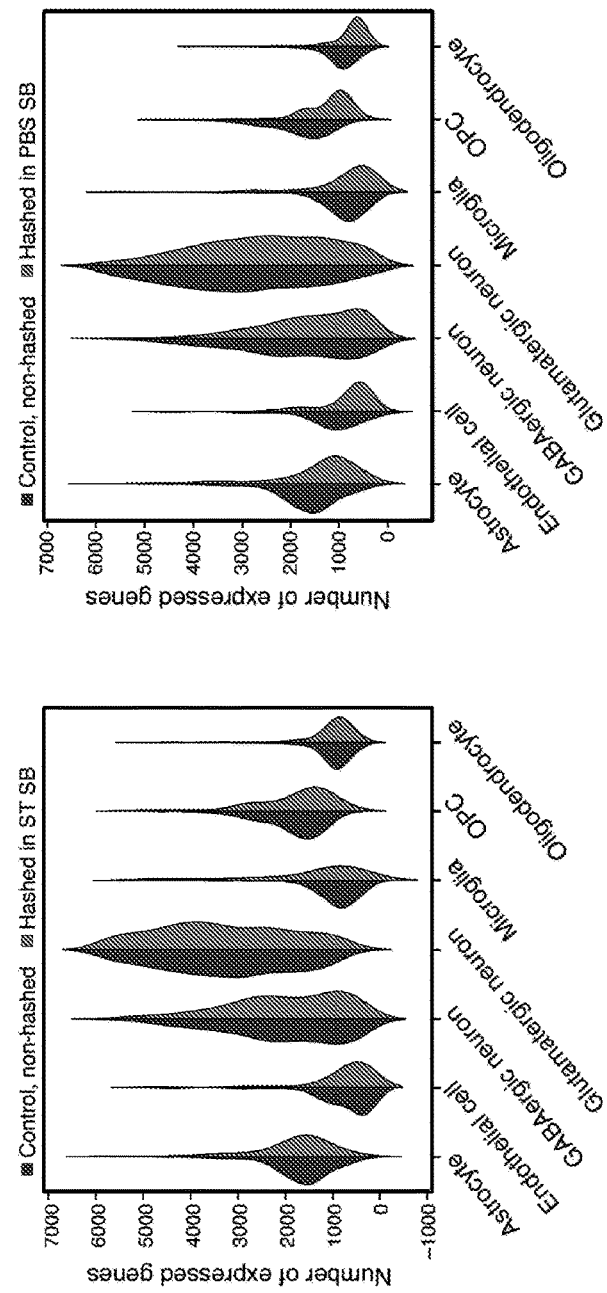
FIG. 14A
FIG. 14B
FIG. 14C

SEQUENCE LISTING

```
<160> NUMBER OF SEQ ID NOS: 35

<210> SEQ ID NO 1
<211> LENGTH: 15
<212> TYPE: DNA
<213> ORGANISM: Homo sapiens

<400> SEQUENCE: 1
ttcctgccat tacta                                                  15

<210> SEQ ID NO 2
<211> LENGTH: 15
<212> TYPE: DNA
<213> ORGANISM: Homo sapiens

<400> SEQUENCE: 2
ccgtacctca ttgtt                                                  15

<210> SEQ ID NO 3
<211> LENGTH: 15
<212> TYPE: DNA
<213> ORGANISM: Homo sapiens

<400> SEQUENCE: 3
ggtagatgtc ctcag                                                  15

<210> SEQ ID NO 4
<211> LENGTH: 15
<212> TYPE: DNA
<213> ORGANISM: Homo sapiens

<400> SEQUENCE: 4
tggtgtcatt cttga                                                  15

<210> SEQ ID NO 5
<211> LENGTH: 15
<212> TYPE: DNA
<213> ORGANISM: Homo sapiens

<400> SEQUENCE: 5
atgatgaaca gccag                                                  15

<210> SEQ ID NO 6
<211> LENGTH: 15
<212> TYPE: DNA
<213> ORGANISM: Homo sapiens

<400> SEQUENCE: 6
ctcgaacgct tatcg                                                  15
```

```
<210> SEQ ID NO 7
<211> LENGTH: 15
<212> TYPE: DNA
<213> ORGANISM: Homo sapiens

<400> SEQUENCE: 7
tgacgccgtt gttgt                                                    15

<210> SEQ ID NO 8
<211> LENGTH: 15
<212> TYPE: DNA
<213> ORGANISM: Homo sapiens

<400> SEQUENCE: 8
gcctagtatg atcca                                                    15

<210> SEQ ID NO 9
<211> LENGTH: 15
<212> TYPE: DNA
<213> ORGANISM: Homo sapiens

<400> SEQUENCE: 9
ttcctgccat tacta                                                    15

<210> SEQ ID NO 10
<211> LENGTH: 15
<212> TYPE: DNA
<213> ORGANISM: Homo sapiens

<400> SEQUENCE: 10
ccgtacctca ttgtt                                                    15

<210> SEQ ID NO 11
<211> LENGTH: 15
<212> TYPE: DNA
<213> ORGANISM: Homo sapiens

<400> SEQUENCE: 11
ggtagatgtc ctcag                                                    15

<210> SEQ ID NO 12
<211> LENGTH: 15
<212> TYPE: DNA
<213> ORGANISM: Homo sapiens

<400> SEQUENCE: 12
tggtgtcatt cttga                                                    15

<210> SEQ ID NO 13
<211> LENGTH: 15
<212> TYPE: DNA
<213> ORGANISM: Homo sapiens

<400> SEQUENCE: 13
atgatgaaca gccag                                                    15

<210> SEQ ID NO 14
<211> LENGTH: 15
<212> TYPE: DNA
<213> ORGANISM: Homo sapiens

<400> SEQUENCE: 14
ctcgaacgct tatcg                                                    15
```

```
<210> SEQ ID NO 15
<211> LENGTH: 15
<212> TYPE: DNA
<213> ORGANISM: Homo sapiens

<400> SEQUENCE: 15
tgacgccgtt gttgt                                                     15

<210> SEQ ID NO 16
<211> LENGTH: 15
<212> TYPE: DNA
<213> ORGANISM: Homo sapiens

<400> SEQUENCE: 16
gcctagtatg atcca                                                     15

<210> SEQ ID NO 17
<211> LENGTH: 15
<212> TYPE: DNA
<213> ORGANISM: Homo sapiens

<400> SEQUENCE: 17
atgatgaaca gccag                                                     15

<210> SEQ ID NO 18
<211> LENGTH: 15
<212> TYPE: DNA
<213> ORGANISM: Homo sapiens

<400> SEQUENCE: 18
ctcgaacgct tatcg                                                     15

<210> SEQ ID NO 19
<211> LENGTH: 15
<212> TYPE: DNA
<213> ORGANISM: Homo sapiens

<400> SEQUENCE: 19
cttatcaccg ctcaa                                                     15

<210> SEQ ID NO 20
<211> LENGTH: 15
<212> TYPE: DNA
<213> ORGANISM: Homo sapiens

<400> SEQUENCE: 20
tgacgccgtt gttgt                                                     15

<210> SEQ ID NO 21
<211> LENGTH: 15
<212> TYPE: DNA
<213> ORGANISM: Mus musculus

<400> SEQUENCE: 21
ttcctgccat tacta                                                     15

<210> SEQ ID NO 22
<211> LENGTH: 15
<212> TYPE: DNA
<213> ORGANISM: Mus musculus

<400> SEQUENCE: 22
```
ccgtacctca ttgtt                                                          15

<210> SEQ ID NO 23
<211> LENGTH: 15
<212> TYPE: DNA
<213> ORGANISM: Mus musculus

<400> SEQUENCE: 23
ggtagatgtc ctcag                                                          15

<210> SEQ ID NO 24
<211> LENGTH: 15
<212> TYPE: DNA
<213> ORGANISM: Mus musculus

<400> SEQUENCE: 24
tggtgtcatt cttga                                                          15

<210> SEQ ID NO 25
<211> LENGTH: 15
<212> TYPE: DNA
<213> ORGANISM: Mus musculus

<400> SEQUENCE: 25
ttcctgccat tacta                                                          15

<210> SEQ ID NO 26
<211> LENGTH: 15
<212> TYPE: DNA
<213> ORGANISM: Mus musculus

<400> SEQUENCE: 26
ccgtacctca ttgtt                                                          15

<210> SEQ ID NO 27
<211> LENGTH: 15
<212> TYPE: DNA
<213> ORGANISM: Mus musculus

<400> SEQUENCE: 27
ggtagatgtc ctcag                                                          15

<210> SEQ ID NO 28
<211> LENGTH: 15
<212> TYPE: DNA
<213> ORGANISM: Mus musculus

<400> SEQUENCE: 28
tggtgtcatt cttga                                                          15

<210> SEQ ID NO 29
<211> LENGTH: 15
<212> TYPE: DNA
<213> ORGANISM: Mus musculus

<400> SEQUENCE: 29
atgatgaaca gccag                                                          15

<210> SEQ ID NO 30
<211> LENGTH: 15
<212> TYPE: DNA
<213> ORGANISM: Mus musculus

<400> SEQUENCE: 30

```
ctcgaacgct tatcg                                                   15

<210> SEQ ID NO 31
<211> LENGTH: 15
<212> TYPE: DNA
<213> ORGANISM: Mus musculus

<400> SEQUENCE: 31
cttatcaccg ctcaa                                                   15

<210> SEQ ID NO 32
<211> LENGTH: 15
<212> TYPE: DNA
<213> ORGANISM: Mus musculus

<400> SEQUENCE: 32
tgacgccgtt gttgt                                                   15

<210> SEQ ID NO 33
<211> LENGTH: 25
<212> TYPE: DNA
<213> ORGANISM: Artificial Sequence
<220> FEATURE:
<223> OTHER INFORMATION: Synthetic Primer

<400> SEQUENCE: 33
gtgactggag ttcagacgtg tgctc                                        25

<210> SEQ ID NO 34
<211> LENGTH: 55
<212> TYPE: DNA
<213> ORGANISM: Artificial Sequence
<220> FEATURE:
<223> OTHER INFORMATION: Synthetic Primer

<400> SEQUENCE: 34
caagcagaag acggcatacg agatcgagta atgtgactgg agttcagacg tgtgc       55

<210> SEQ ID NO 35
<211> LENGTH: 49
<212> TYPE: DNA
<213> ORGANISM: Artificial Sequence
<220> FEATURE:
<223> OTHER INFORMATION: Synthetic Primer

<400> SEQUENCE: 35
aatgatacgg cgaccaccga gatctacact ctttccctac acgacgctc              49
```

METHODS AND COMPOSITIONS FOR MULTIPLEXING SINGLE CELL AND SINGLE NUCLEI SEQUENCING

CROSS-REFERENCE TO RELATED APPLICATIONS

This application claims the benefit of U.S. Provisional Application Nos. 62/595,904, filed Dec. 7, 2017, 62/751,489, filed Oct. 26, 2018 and 62/770,580, filed Nov. 21, 2018. The entire contents of the above-identified applications are hereby fully incorporated herein by reference.

STATEMENT REGARDING FEDERALLY SPONSORED RESEARCH

This invention was made with government support under Grant No. MH114821 awarded by the National Institutes of Health. The government has certain rights in the invention.

REFERENCE TO AN ELECTRONIC SEQUENCE LISTING

The contents of the electronic sequence listing (BROD_3920_ST25.txt"; Size is 6 Kilobytes and it was created on Nov. 29, 2018) is herein incorporated by reference in its entirety.

TECHNICAL FIELD

The present invention provides methods and tools for analyzing genetic interactions. The subject matter disclosed herein is generally directed to single cell genomics and proteomics.

BACKGROUND

Regulatory circuits in cells process signals, trigger decisions, and orchestrate physiological responses under diverse conditions. Diseases, in turn, arise from circuit malfunctions: one or more components are missing or defective; a key component is over- or under-active. To understand mechanisms underlying disease and develop more effective treatments, it would be highly advantageous to be able to provide a comprehensive picture of all cellular components, to identify the circuits in which they function, and to delineate how these components and circuits are integrated to form cellular responses.

Genomic research on dissecting cellular circuitry has generally had distinct phases: genomic observations and perturbation of single components.

Early advances in functional genomics made it possible to observe molecular profiles in different cells. Such global analysis has been very powerful in drawing hypotheses that relate regulators to their targets from statistical correlations. However, it is also very limited: the hypotheses were mostly not tested, and because correlation is not causation, many hypotheses may be found partially or fully incorrect.

In recent years, efforts were implemented in order to determine causation. Genomic profiles were used to infer a molecular model, on an increasingly large scale, based on genetic manipulations. However, the approach of testing genes individually has limitations: because genes involved in biological circuits have non-linear interactions, one cannot predict how a cellular circuit functions simply by summing up the individual effects. Indeed, biological systems are not linear: the combined effect of multiple factors is not simply the sum of their individual effects. This is a direct outcome of the biochemistry underlying molecular biology, from allosteric protein changes to cooperative binding, and is essential for cells to process complex signals.

It has remained an insurmountable stumbling block to achieving a quantitative and predictive understanding of circuits on a genomic scale, with far-reaching implications for basic and translational science. For example, despite decades of work, one still cannot predict how the enhancer controlling the transcription of the interferon beta gene (IFNβ) behaves in response to viral and other stimuli. In another example, p38α, a serine/threonine kinase with key roles in inflammation, has been studied for two decades, and yet it remains unclear how it balances control of inflammatory and anti-inflammatory cytokines, and many therapeutics programs launched to target this protein were hampered by unwarranted and unexpected effects. Finally, in genomic studies ranging from yeast to mammals, many molecular events (e.g., transcription factor binding) appear 'functionally silent' upon factor perturbation, and only some expression variation is explained with available mechanistic data.

SUMMARY

In certain example embodiments, the present invention provides for nuclei hashing for multiplexing multiple tissue samples in single cell genomics and/or proteomics.

In one aspect, the present invention provides for a method of multiplexing samples for single cell sequencing comprising: labeling single cells from each of a plurality of samples with a sample barcode oligonucleotide unique to each sample; and constructing a multiplexed single cell sequencing library for the plurality of samples comprising cell of origin barcodes, wherein the sample barcode oligonucleotide on each labeled cell receives a cell of origin barcode. In certain embodiments, the method further comprises sequencing the library and demultiplexing in silico based on the cell of origin barcodes and the sample barcodes.

In certain embodiments, the single cells are labeled with one or more antibodies linked to the sample barcode oligonucleotide. In certain embodiments, the one or more antibodies are specific for one or more surface markers present on single cells in the plurality of samples.

In certain embodiments, the single cells are modified to accept covalent linkage of the sample barcode oligonucleotide and the cells are labeled by covalent linkage of the sample barcode oligonucleotide. In certain embodiments, the cells are modified with an acceptor molecule capable of being covalently linked to the sample barcode oligonucleotide by click chemistry and wherein the cells are labeled with sample barcode oligonucleotides modified for click chemistry. In certain embodiments, the cells are modified with a biotin moiety and the sample barcode oligonucleotide comprises avidin, whereby the cells are labeled by biotin-avidin binding.

In certain embodiments, constructing a single cell sequencing library comprises sorting or segregating cells into individual discrete volumes, each volume comprising cell of origin barcodes specific to the volume. In certain embodiments, the individual discrete volumes are droplets, microfluidic chambers, microwells, or wells. In certain embodiments, constructing a single cell sequencing library comprises split and pool barcoding.

In certain embodiments, the multiplexed single cell sequencing library is an RNA sequencing library. In certain embodiments, the multiplexed single cell sequencing library is an ATAC sequencing library. In certain embodiments, the multiplexed single cell sequencing library provides a proteomics readout. In certain embodiments, the multiplexed single cell sequencing library provides a targeted gene expression readout, wherein specific genes are targeted with a probe capable of being labeled with the sample barcode. In certain embodiments, the multiplexed single cell sequencing library provides a readout comprising transcriptome, ATAC, proteomic, targeted gene expression, or any combination thereof.

In another aspect, the present invention provides for a method of multiplexing samples for single nuclei sequencing comprising: labeling single nuclei from each of a plurality of samples with a sample barcode oligonucleotide unique to each sample; and constructing a multiplexed single nuclei sequencing library for the plurality of samples comprising cell of origin barcodes, wherein the sample barcode oligonucleotide on each labeled nuclei receives a cell of origin barcode. In certain embodiments, the single nuclei are obtained from a population of cells, fresh tissue, frozen tissue or fixed formalin paraffin embedded (FFPE) tissues. In certain embodiments, the method further comprises sequencing the library and demultiplexing in silico based on the cell of origin barcodes and the sample barcodes.

In certain embodiments, the single nuclei are labeled with one or more antibodies linked to the sample barcode oligonucleotide. In certain embodiments, the one or more antibodies are specific for one or more proteins present on the nuclear membrane of the single nuclei in the plurality of samples. In certain embodiments, the one or more antibodies are specific for one or more nuclear pore proteins. In certain embodiments, the one or more antibodies are selected from the group consisting of Lamin-A, Lamin-B, Lamin-C, NUP98, NUP153, and NUP214. In certain embodiments, nuclei are labeled in a buffer comprising 2% BSA, 0.02% Tween-20, 10 mM Tris, 146 mM NaCl, 1 mM $CaCl_2$, and 21 mM $MgCl_2$.

In certain embodiments, the single nuclei are modified to accept covalent linkage of the sample barcode oligonucleotide and the nuclei are labeled by covalent linkage of the sample barcode oligonucleotide. In certain embodiments, the nuclei are modified with an acceptor molecule capable of being covalently linked to the sample barcode oligonucleotide by click chemistry and wherein the nuclei are labeled with sample barcode oligonucleotides modified for click chemistry. In certain embodiments, the nuclei are modified with a biotin moiety and the sample barcode oligonucleotide comprises avidin, whereby the nuclei are labeled by biotin-avidin binding.

In certain embodiments, constructing a single cell sequencing library comprises sorting or segregating cells into individual discrete volumes, each volume comprising cell of origin barcodes specific to the volume. In certain embodiments, the individual discrete volumes are droplets, microfluidic chambers, microwells, or wells. In certain embodiments, constructing a single cell sequencing library comprises split and pool barcoding.

In certain embodiments, the multiplexed single cell sequencing library is an RNA sequencing library. In certain embodiments, the multiplexed single cell sequencing library is an ATAC sequencing library. In certain embodiments, the multiplexed single cell sequencing library provides a proteomics readout. In certain embodiments, the multiplexed single cell sequencing library provides a targeted gene expression readout, wherein specific genes are targeted with a probe capable of being labeled with the sample barcode. In certain embodiments, the multiplexed single cell sequencing library provides a readout comprising transcriptome, ATAC, proteomic, targeted gene expression, or any combination thereof.

In certain embodiments, the method further comprises sequencing the library and defining each cell barcode as a singlet, doublet, or unknown by applying an algorithm that calculates the probability that a sample barcode detected with a cell barcode was due to background or a sample, wherein if a cell barcode is associated with two sample barcodes and the probability of background is low the cell barcode is associated with a doublet. In certain embodiments, only singlets are analyzed.

In certain embodiments, the method further comprises enriching for nuclei expressing one or more genes of interest. In certain embodiments, nuclei are stained with fluorescent RNA probes specific for the one or more genes of interest and enriched by FACS.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 3—illustrates the demuxEM computational method for demultiplexing.

FIG. 14—Buffer optimization for multiplexing. a. tSNE of single nucleus profiles from non-hashed control, PBS-based (PBS-SB) and ST-based staining buffer (ST-SB) colored by either cell type (left) or protocol (right). Nuclei stained with ST-SB buffer (green) largely overlap with the non-hashing control nuclei (blue), whereas PBS-stained nuclei (orange) show some separation within the clusters. b,c. Decreased number of expressed genes detected when using PBS-SB. Distribution of number of expressed genes (y axis) across cell types (x axis) for nuclei stained with ST-SB (b, orange) or PBS-SB (c, orange) compared to the non-hashing control (blue).

Figure 1:
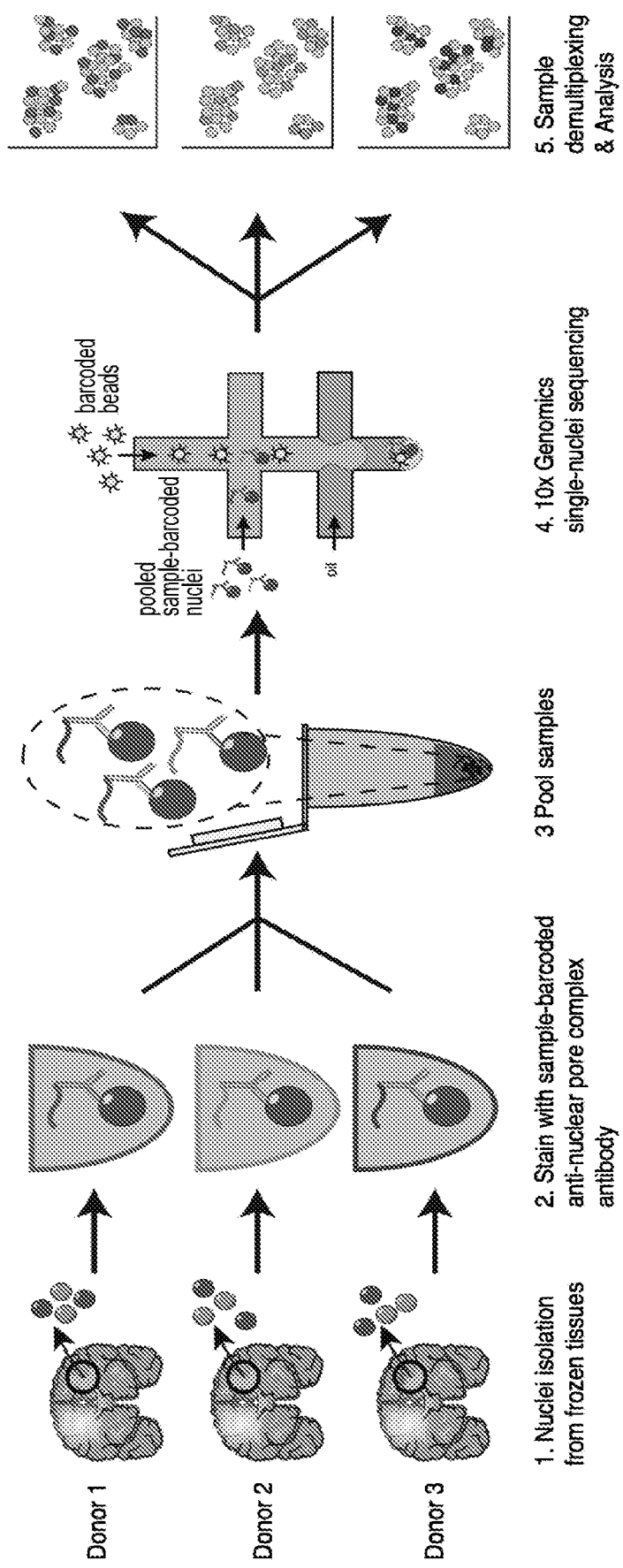
FIG. 1—illustrates a schematic of a nuclei-hashing protocol.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratry Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

Reference is made to provisional application 62/595,904, filed Dec. 7, 2017, PCT/US16/059233, filed Oct. 27, 2016, PCT/US2016/059195, filed Oct. 27, 2016, and PCT/US16/059230 filed Oct. 27, 2016. Reference is also made to U.S. provisional application Ser. Nos. 62/247,630 filed Oct. 28, 2015, 62/247,656 filed Oct. 28, 2015, 62/372,393 filed Aug. 9, 2016, 62/247,729 filed Oct. 28, 2015, 62/394,721 filed Sep. 14, 2016, 62/395,273 filed Sep. 15, 2016, and 62/500,784 filed May 3, 2017.

All publications, published patent documents, and patent applications cited herein are hereby incorporated by reference to the same extent as though each individual publication, published patent document, or patent application was specifically and individually indicated as being incorporated by reference.

Overview

A current phase of genomic research on dissecting cellular circuitry involves combinatorial probing of circuits. It would be desirable to provide a combinatorial approach: perturbing multiple components, at a large enough scale that will allow one to reliably reconstruct cellular circuits; for example, simultaneously or at or about the same time or in parallel. Such a combinatorial genomics approach has generally been considered intractable, because it required: (1) the ability to perturb many genes simultaneously (or at or about the same time or in parallel) in the same cell; (2) the ability to readout genomic profiles in individual cells, so that the effect of many perturbations can be assessed in parallel in a pool of cells; and (3) the development of mathematics and computational tools, because even millions of experiments are very few compared to the staggering size of the possible combinatorial space.

The invention involves Massively Parallel Combinatorial Perturbation Profiling (MCPP) to address or identify genetic interactions. Biological systems are not linear: the combined effect of multiple factors is not simply the sum of their individual effects. This is a direct outcome of the biochemistry underlying molecular biology, from allosteric protein changes to cooperative binding, and is essential for cells to process complex signals. However, heretofore, it has remained an insurmountable stumbling block to quantitative and predictive biology on a genomic scale, with far-reaching implications e.g., from basic research to clinical translation. The invention provides a combinatorial approach: perturbing multiple components simultaneously. Yet, even recent experimental advances in genetics and genomics heretofore have not been enough; for instance, studying all 2-way, 3-way and 4-way interactions would, prior to the instant invention, require performing ~$10^8$, ~$10^{12}$, and ~$10^{16}$ combinations of perturbations, respectively; and, beyond the technological and cost issues, the sheer number of mammalian cells required becomes infeasible because, for example, even if one focused on 100 genes, exhaustive analysis of 5-way interactions would require 70 million perturbations.

It would be desirable to provide tools and methods for the systematic analysis of genetic interactions, including higher order interactions.

It would be desirable to provide tools and/or methods for combinatorial probing of cellular circuits, for instance, for dissecting cellular circuitry, for delineating molecular pathways and/or interactions (e.g., intercellular and/or intracellular pathways or interactions), for identifying relevant targets and/or for identifying impact or effect of perturbations or stimuli or mutation; for instance for therapeutics development and/or cellular engineering and/or any cellular manipulation and/or ascertaining internal cell function and/or for bioproduction (e.g., production of antibodies from new sources, expression of products from organisms or cells that previously did not naturally express such products, increasing or decreasing expression of endogenous products, and the like), new plants or animal models.

The present invention involves cellular circuits (both intracellular and extracellular circuits). For instance, a cellular, e.g., regulatory circuit combines trans inputs (such as the levels and activities of factors, e.g., transcription factors, non-coding RNAs, e.g., regulatory RNAs and signaling molecules) and cis inputs (such as sequences, e.g., regulatory sequences in the promoter and enhancer of a gene); for instance, to determine the level of mRNA produced from a gene.

Reconstruction of a cellular, e.g., regulatory circuit is to identify inputs, e.g., all identifiable inputs (for example, proteins, non-coding RNAs and cis-regulatory elements), their physical 'wirings' (or connections) and the transcriptional functions that they implement; for instance, as to regulation of the level of mRNA.

A model should address (advantageously simultaneously or in parallel) providing a functional description of the input-output relationships (for example, if regulator A is induced, then target gene B is repressed to a particular extent), and providing a physical description of the circuit (for example, regulator A binds to the promoter of gene B in sequence Y, modifies its chromatin and leads to repression). Networks, e.g., regulatory networks, control complex downstream cellular phenotypes (such as cell death, proliferation and migration).

Reconstructing the connectivity of a network can be through the monitoring of hundreds to thousands of cellular parameters (massively parallel monitoring or hundreds to thousands of cellular parameters), such as the levels of mRNAs. Hence "massively parallel" can mean undertaking a particular activity hundreds to thousands to millions, e.g., from 100 to 1000 or to 10,000 or to 100,000 or to 1,000,000 or up to 1,000,000,000 times (or as otherwise indicated herein or in figures herewith), in parallel, e.g., simultaneously or at or about the same time. See, e.g., Amit et al., "Strategies to discover regulatory circuits of the mammalian immune system," Nature Reviews (Immunology) 11: 873-880 (December 2011).

The present invention relates to methods of measuring or determining or inferring RNA levels, e.g., massively parallel measuring or determining or inferring of RNA levels in a single cell or a cellular network or circuit in response to at least one perturbation parameter or advantageously a plurality of perturbation parameters or massively parallel perturbation parameters involving sequencing DNA of a perturbed cell, whereby RNA level and optionally protein level may be determined in the single cell in response to the at least one perturbation parameter or advantageously a plurality of perturbation parameters or massively parallel perturbation parameters.

The invention thus may involve a method of inferring or determining or measuring RNA in a single cell or a cellular network or circuit, e.g., massively parallel inferring or determining or measuring of RNA level in a single cell or a cellular network or circuit in response to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 or massively parallel perturbation parameter(s) comprising optionally so perturbing the cell or the cells or each cell of the cellular network or circuit with the perturbation parameter(s) and sequencing of the perturbed cell(s), whereby RNA level(s) and optionally protein level(s) is/are determined in the cell(s) in response to the perturbation parameter(s).

Genetic screens are used to infer gene function in mammalian cells, but it has remained difficult to assay complex phenotypes—such as genome-wide transcriptional profiles—in large-scale screens. Moreover, it has been traditionally difficult to assay the transcriptional phenotype of genetic perturbations at scale. Preferably, a genomewide scale transcriptome phenotype associated with a perturbation would be possible.

Embodiments disclosed herein also provide methods of multiplexing more than one sample for single cell genomics and proteomics (e.g., single cell RNA sequencing and CITE-seq). Embodiments disclosed herein also provide methods of performing genomewide CRISPR perturbation screens.

Embodiments disclosed herein also provide methods of multiplexing more than one sample for single nucleus genomics. Single-nucleus RNA-Seq (snRNA-seq) enables the interrogation of cellular states in complex tissues that are challenging to dissociate, including frozen clinical samples. This opens the way to large studies, such as those required for human genetics, clinical trials, or precise cell atlases of large organs. However, such applications are currently limited by batch effects, sequential processing, and costs. To address these challenges, Applicants present an approach for multiplexing snRNA-seq, using sample-barcoded antibodies against the nuclear pore complex to uniquely label nuclei from distinct samples. Comparing human brain cortex samples profiled in multiplex with or without hashing antibodies, Applicants demonstrate that nucleus hashing does not significantly alter the recovered transcriptome profiles. Applicants further developed demuxEM, a novel computational tool that robustly detects inter-sample nucleus multiplets and assigns singlets to their samples of origin by antibody barcodes, and validated its accuracy using gender-specific gene expression, species-mixing and natural genetic variation. Nucleus hashing significantly reduces cost per nucleus, recovering up to about 5 times as many single nuclei per microfluidic channel. The approach provides a robust technique for diverse studies including tissue atlases of isogenic model organisms or from a single larger human organ, multiple biopsies or longitudinal samples of one donor, and large-scale perturbation screens.

Multiplexing Single Cell RNA-Sequencing Using DNA Sample Barcodes

In certain embodiments, different samples of single cells are multiplexed to generate a multiplexed single sequencing library. The samples may be from different subjects, different tissues, different time points in an experiment, from different samples treated under different conditions in an experiment, or from different perturb-seq experiments (e.g., replicates). In certain embodiments, the sequencing library is sequenced and demultiplexed in silico.

Recently, droplet-based (see, e.g., Macosko, et al., Highly parallel genome-wide expression profiling of individual cells using nanoliter droplets. Cell, 161(5):1202-1214, 2015; and Dixit, et al., Perturb-seq: dissecting molecular circuits with scalable single-cell RNA profiling of pooled genetic screens. Cell, 167(7):1853-1866, 2016) and combinatorial split-pool methods (see, e.g., Vitak, et al., Sequencing thousands of single-cell genomes with combinatorial indexing. Nature Methods, 14(3):302-308, 2017; Cao, et al., Comprehensive single-cell transcriptional profiling of a multicellular organism. Science, 357(6352):661-667, 2017; and Rosenberg et al., Scaling single cell transcriptomics through split pool barcoding. bioRxiv preprint first posted online Feb. 2, 2017, doi:dx.doi.org/10.1101/105163) have significantly increased the throughput of single-cell assays and, enabled sequencing based quantification of transcriptional, proteomic and epigenetic states of thousands of cells from one microfluidic reaction.

Multiplexing samples would significantly reduce cost and technical variability associated with sample processing and library generation, improving the statistical power to resolve biological from technical effects.

Recently, sample multiplexing over different human donor samples in silico was performed by demultiplexing over a set of single nucleotide polymorphisms (SNPs) in the RNA-seq reads that provide a donor specific signature (Kanget et al., Multiplexing droplet-based single cell RNA-sequencing using natural genetic barcodes. bioRxiv, page 118778, 2017).

Here, Applicants provide a method that allows pooling of samples in a single microfluidic (e.g., droplet based single cell sequencing, such as Drop-seq, InDrop, 10×) or split-pool reaction by labeling cells with DNA sample-barcodes, irrespective of their genomic profiles. As used herein, "sample barcode" may also be referred to as a sample hash and the method may be referred to as cell hashing and/or nuclei hashing. By doing so, Applicants enable pooling multiple samples from a single patient, for instance isolated from different tissues, or analyzing different cell types. Or samples from a patient that have received different ex vivo treatments (for instance, responses to different drugs, or other perturbations). Similarly, one can pool samples from other organisms such as mice with isogenic backgrounds, that for instance, are sampled at different time points.

The term "barcode" as used herein refers to a short sequence of nucleotides (for example, DNA or RNA) that is used as an identifier for an associated molecule, such as a target molecule and/or target nucleic acid, or as an identifier of the source of an associated molecule, such as a cell-of-origin. A barcode may also refer to any unique, non-naturally occurring, nucleic acid sequence that may be used to identify the originating source of a nucleic acid fragment. Although it is not necessary to understand the mechanism of an invention, it is believed that the barcode sequence provides a high-quality individual read of a barcode associated with a single cell, a viral vector, labeling ligand (e.g., an aptamer), protein, shRNA, sgRNA or cDNA such that multiple species can be sequenced together.

Barcoding may be performed based on any of the compositions or methods disclosed in patent publication WO 2014047561 A1, Compositions and methods for labeling of agents, incorporated herein in its entirety. In certain embodiments barcoding uses an error correcting scheme (T. K. Moon, Error Correction Coding: Mathematical Methods and Algorithms (Wiley, New York, ed. 1, 2005)). Not being bound by a theory, amplified sequences from single cells can be sequenced together and resolved based on the barcode associated with each cell.

Attaching barcode sequences to nucleic acids is shown in U.S. Pub. 2008/0081330 and PCT/US09/64001, the content of each of which is incorporated by reference herein in its entirety. Methods for designing sets of barcode sequences and other methods for attaching barcode sequences are shown in U.S. Pat. Nos. 6,138,077; 6,352,828; 5,636,400; 6,172,214; 6235,475; 7,393,665; 7,544,473; 5,846,719; 5,695,934; 5,604,097; 6,150,516; RE39,793; 7,537,897; 6172,218; and 5,863,722, the content of each of which is incorporated by reference herein in its entirety The term "barcode" as used herein refers to a short sequence of nucleotides (for example, DNA or RNA) that is used as an identifier for an associated molecule, such as a target molecule and/or target nucleic acid, or as an identifier of the source of an associated molecule, such as a cell-of-origin. A barcode may also refer to any unique, non-naturally occurring, nucleic acid sequence that may be used to identify the originating source of a nucleic acid fragment. Although it is not necessary to understand the mechanism of an invention, it is believed that the barcode sequence provides a high-quality individual read of a barcode associated with a single cell, a viral vector, labeling ligand (e.g., an aptamer), protein, shRNA, sgRNA or cDNA such that multiple species can be sequenced together.

In one application, Applicants can stain cells with a sample specific barcoded antibody using methods and oligo linked antibodies similar to those described previously that target an epitope accessible from staining buffer (Stoeckius et al., Simultaneous epitope and transcriptome measurement in single cells. Nat Methods. 2017 September; 14(9):865-868). In certain embodiments, the epitope is selected such that it is expressed on all samples to be pooled. For each separate sample, the antibody barcoding the sample gets a different sample barcode, such that samples can be demultiplexed in silico. This approach only adds a short (5-10 minutes) antibody staining step to existing single-cell methods. In certain embodiments, cells are stained for less than 1 minute, 1 minute, 5 minutes, 10 minutes or more depending on the amount of antibody used or depending on the specific antibody. In certain embodiments, the antibody staining step uses a washing step to remove unbound antibodies that may crossreact across samples when the samples are multiplexed. One skilled in the art understands optimization of conditions for specific antibodies, such as for binding and washing steps.

In certain embodiments, more than one barcoded antibody is used to ensure every cell type in a sample is labeled with a sample barcode. In certain embodiments, panels of antibodies (e.g., 2 or 3 or more) are used to label cells in a sample. Not being bound by a theory a panel of two or three antibodies to common surface markers will label every cell type in a sample. In certain embodiments, the antibodies in the panel of antibodies are labeled with the same sample barcode oligonucleotide for each separate sample.

In certain embodiments, the antibody is selected from a group of generic antibodies specific for common antigens expressed by the cells in a sample. For example, if immune cells are analyzed an antibody against a common immune marker may be used.

In certain embodiments, common surface proteins applicable to the present invention include, but are not limited to human CD antigens selected from CD1a, CD1b, CD1c, CD1d, CD1e, CD2, CD2R, CD3 gamma, CD3 delta, CD3 epsilon, CD4, CD5, CD6, CD7, CD8a, CD8b, CD9, CD10, CD11a, CD11b, CD11c, CD12, CD13, CD14, CD15, CD15s, CD15u, CD16a, CD16b, CD17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD44v, CD45, CD45RA, CD45RB, CD45RO, CD46, CD47, CD47R, CD48, CD49a, CD49b, CD49c, CD49d, CD49e, CD49f, CD50, CD51, CD52, CD53, CD54, CD55, CD56, CD57, CD58, CD59, CD60a, CD60b, CD60c, CD61, CD62E, CD62L, CD62P, CD63, CD64, CD65, CD65s, CD66a, CD66b, CD66c, CD66d, CD66e, CD66f, CD68, CD69, CD70, CD71, CD72, CD73, CD74, CD75, CD75s, CD77, CD79a, CD79b, CD80, CD81, CD82, CD83, CDw84, CD85, CD86, CD87, CD88, CD89, CD90, CD91, CD92, CD93, CD94, CD95, CD96, CD97, CD98, CD99, CD99R, CD100, CD101, CD102, CD103, CD104, CD105, CD106, CD107a, CD107b, CD108, CD109, CD110, CD111, CD112, CD113, CD114, CD115, CD116, CD117, CD118, CD119, CD120a, CD120b, CD121a, CD121b, CD122, CD123, CD124, CD125, CD126, CD127, CD128, CD130, CD131, CD132, CD133, CD134, CD135, CD136, CD137, CD138, CD139, CD140a, CD140b, CD141, CD142, CD143, CD144, CD145, CD146, CD147, CD148, CD150, CD151, CD152, CD153, CD154, CD155, CD156a, CD156b, CD156c, CD157, CD158a, CD158b, CD159a, CD159c, CD160, CD161, CD162, CD162R, CD163, CD164, CD165, CD166, CD167a, CD168, CD169, CD170, CD171, CD172a, CD172b, CD172g, CD173, CD174, CD175, CD175s, CD176, CD177, CD178, CD179a, CD179b, CD180, CD181, CD182, CD183, CD184, CD185, CD186, CD191, CD192, CD193, CD195, CD196, CD197, CD198, CD199, CD200, CD201, CD202b, CD203c, CD204, CD205, CD206, CD207, CD208, CD209, CD210, CD212, CD213a1, CD213a2, CD217, CD218a, CD218b, CD220, CD221, CD222, CD223, CD224, CD225, CD226, CD227, CD228, CD229, CD230, CD231, CD232, CD233, CD234, CD235a, CD235ab, CD235b, CD236, CD236R, CD238, CD239, CD240CE, CD240D, CD241, CD242, CD243, CD244, CD245, CD246, CD247, CD248, CD249, CD252, CD253, CD254, CD256, CD257, CD258, CD261, CD262, CD263, CD264, CD265, CD266, CD267, CD268, CD269, CD271, CD272, CD273, CD274, CD275, CD276, CD277, CD278, CD279, CD280, CD281, CD282, CD283, CD284, CD289, CD292, CD293, CD294, CD295, CD296, CD297, CD298, CD299, CD300a, CD300c, CD300e, CD301, CD302, CD303, CD304, CD305, CD306, CD307, CD309, CD312, CD314, CD315, CD316, CD317, CD318, CD319, CD320, CD321, CD322, CD324, CD325, CD326, CD327, CD328, CD329, CD331, CD332, CD333, CD334, CD335, CD336, CD337, CD338 or CD339; other human non-CD cellular antigens selected from 4-1BB Ligand, AID, AITR, AITRL, B7 family, B7-H4, BAMBI, BCMA, BLyS, BR3, BTLA, CCR7, c-Met, CMKLR1, DcR3, DEC-205, DR3, DR6, Fc epsilonRI alpha, Foxp3, Granzyme B, HLA-ABC, HLA-DR, HVEM, ICOS, ICOSL, IL-15R alpha, Integrin beta5, MD-2, MICA/MICB, Nanog, NKG2D, NOD2, Notch-1, OPG, OX-40, OX-40 Ligand, p38, PD-1, PD-L1, PD-L2, Perforin, RP105, RANK, RANKL, SAP, SLP-76, SSEA-1, SSEA-3, SSEA-4, Stro-1, TACI, T-bet, TCL1, TCR alpha beta, TCR gamma delta, TLR1-TLR4, TLR5, TLR6, TLR7, TLR8, TLR9, TLR10, TNFRI, TRAIL, TSLPR, TWEAK, TWEAK Receptor, ULBPs, ZAP-70; mouse CD antigens selected from CD1d, CD2, CD3d, CD3e, CD3g, CD4, CD5, CD6, CD7, CD8a, CD8b, CD9, CD10, CD11a, CD11b, CD11c, CD13, CD14, CD15, CD16, CD18, CD19, CD20, CD21, CD22, CD23, CD24a, CD25, CD26, CD27, CD28, CD29, CD30, CD31, CD32, CD33, CD34, CD35, CD36, CD37, CD38, CD39, CD40, CD41, CD42, CD43, CD44, CD44R, CD45, CD45.1, CD45.2, CD45R/CT1, CD45R, CD45RA, CD45RB, CD45RC, CD45RO, CD46, CD47, CD48, CD49a, CD49b, CD49c, CD49d, CD49e, CD49f, CD50, CD51, CD52, CD53, CD54, CD55, CD56, CD57, CD58 (H), CD59, CD60 (H), CD61, CD62E, CD62L, CD62P, CD63, CD64, CD65 (H), CD66a, CD68, CD69, CD70, CD71, CD72, CD73, CD74, CD75, CD77 (H), CD79a, CD79b, CD80, CD81, CD82, CD83, CD84, CD85, CD86, CD87, CD88, CD89, CD90, CD90.1, CD90.2, CD91, CD92 (H), CD93, CD94, CD95, CD96, CD97, CD98, CD99, CD100, CD101, CD102, CD103, CD104, CD105, CD106, CD107a, CD107b, CD108, CD109, CD110, CD111, CD112, CD113, CD114, CD115, CD116, CD117, CD118, CD119, CD120a, CD120b, CD121a, CD121b, CD122, CD123, CD124, CD125, CD126, CD127, CD128, CD130, CD131, CD132, CD133, CD134, CD135, CD136, CD137, CD138, CD139 (H), CD140a, CD140b, CD141, CD142, CD143, CD144, CD146, CD147, CD148, CD150, CD151, CD152, CD153, CD154, CD155, CD156a, CD156b, CD156c, CD157, CD158 (H), CD159a, CD159c, CD160, CD161c, CD162, CD162R (H), CD163, CD164, CD165, CD166, CD167a, CD168, CD169, CD170 (H), CD171, CD172a, CD172b, CD172g (H), CD173-CD175 (H), CD176, CD177, CD178, CD179a, CD179b, CD180, CD181, CD182, CD183, CD184, CD185, CD186, CD191, CD192, CD193, CD195, CD196, CD197, CD198, CD199, CD200, CD201, CD202b, CD203c, CD204, CD205, CD206, CD207, CD208 (H), CD209, CD210, CD212, CD213a1, CD213a2, CD217, CD218a, CD218b, CD220, CD221, CD222, CD223, CD224, CD225, CD226, CD227, CD228, CD229, CD230, CD231, CD232, CD233, CD234, CD235a, CD236R, CD238, CD239 (H), CD240CE (H), CD241, CD242 (H), CD243, CD244, CD246, CD247, CD248, CD249 (H), CD252, CD253, CD254, CD256, CD257, CD258, CD261 (H), CD262, CD263 (H), CD264 (H), CD265, CD266, CD267, CD268, CD269, CD271, CD272, CD273, CD274, CD275, CD276, CD277 (H), CD278, CD279, CD280, CD281, CD282, CD283, CD284, CD289, CD292, CD293, CD294, CD295, CD296, CD297, CD298, CD299 (H), CD301-302 (H), CD303, CD304, neuropilin 1-Nrp, NP-1, CD305, CD306-307 (H), CD309, CD312 (H), CD314, CD315, CD316, CD317, CD318, CD319, CD320, CD321, CD322, CD324, CD325, CD326, CD327 (H), CD328 (H), CD329, CD331, CD332, CD333, CD334, CD335, CD336 (H), CD337 (H), CD338 or CD339; or mouse non-CD cellular antigen selected from 4-1BBL, 33D1 antigen, AA4.1 antigen, ABCG2, AC133, AID, B7-DC, B7-H1, B7-H2, B7-H3, B7-H4, BP-1, BTLA, CCR7, CIRE, c-Met, CMKLR1, DC maturation marker, DR5, DX5, F4/80 antigen, FIRE, Flk-1, Flt-4, Foxp3, GITR, GITRL, Granzyme B, HVEM, ICOS, IgD, IgE Receptor high affinity, IgM, IL-15R alpha, IL-21R, Jagged-1, JAML, KLRG1, Lymphotoxin beta Receptor, Ly-6A/E, Ly-6B, Ly-6C, Ly-6D, Ly-6F, Ly-6G, Ly-49A, Ly-49B, Ly-49C, Ly-49D, Ly-49E, Ly-49F, Ly-49G, Ly-49H, Ly-49I, Mac-3, MAdCAM-1, MCP-1, MD-1, Nanog, NKG2A, NKG2A B6, NKG2B, NKG2C, NKG2D, NKG2E, Notch-1, OX40 Ligand, PD-1, Perforin, Plexin B2, Prominin-1, RAE-1 gamma, RANK, ROR gamma (t), ROR gamma(t) Products, SAP, Sca-1, Sema4A, SLP-76, SSEA-1, T-bet, TCR alpha beta, TCR gamma delta, TCR-HY, Ter-119, TIE2, TIM-1, TIM-2, TIM-3, TLR1-TLR4, TLR5, TLR6, TLR7, TLR8, TLR9, TLR11, TLR13, TRAIL, TRANCE, TWEAK, TWEAK Receptor or ZAP-70 (see also, CD Marker Handbook, available at www.bdbiosciences.com/documents/cd_marker_handbook.pdf). In a preferred embodiment, CD47 antibodies are used. Antibodies to any of the antigens described herein may be purchased (see, e.g., BD Biosciences, San Jose, Calif.; Biolegend, San Diego, Calif.; or ThermoFisher, Waltham, Mass.). In certain embodiments, the generic antibody may be linked to the sample barcode oligonucleotide in pools, such that each pool includes an oligonucleotide with a different barcode sequence. Any method of attaching oligonucleotides to an antibody may be used herein. In certain embodiments, a streptavidin-biotin interaction may be used to link oligonucleotides to antibodies. In certain embodiments, the antibody-oligonucleotide includes a disulfide link at the 5' end of the oligonucleotide which allows the oligo to be released from the antibody with reducing agents. In certain embodiments, highly specific, FACS optimized monoclonal or polyclonal antibodies are selected.

Antibodies may be conjugated to oligonucleotides containing sample barcode sequences and a polyA tail. Oligonucleotides may be conjugated to antibodies by streptavidin-biotin conjugation using the LYNX Rapid Streptavidin Antibody Conjugation Kit (Bio-Rad, USA), according to manufacturer's instructions with modifications. Specifically, Applicants can label 15 μg of antibody with 10 μg of streptavidin. At this ratio, up to two streptavidin tetramers can theoretically be conjugated to one antibody, which results in 4-8 binding sites for biotin on each antibody. DNA-oligonucleotides can be purchased and/or synthesized with a 5' biotin modification or with a 5' amine modification and biotinylated using NETS-chemistry according to manufacturer's instructions (EZ Biotin S-S NHS, Thermo Fisher Scientific, USA). The disulfide bond allows separation of the oligo from the antibody with reducing agents. Separation of the oligo from the antibody may not be needed for all applications. Excess Biotin-NHS can be removed by gel filtration (Micro Biospin 6, Bio-Rad) and ethanol precipitation. Streptavidin-labelled antibodies can be incubated with biotinylated oligonucleotides in excess (1.5× theoretically available free streptavidin) overnight at 4° C. in PBS containing 0.5M NaCl and 0.02% Tween. Unbound oligo can be removed from antibodies using centrifugal filters with a 100 KDa MW cutoff (Millipore, USA). Removal of excess oligo can be verified by 4% agarose gel electrophoresis. Antibody-oligo conjugates can be stored at 4° C. supplemented with sodium azide and BSA.

Cells can be labeled with oligonucleotide linked antibodies by resuspending cells in cold PBS containing 2% BSA and 0.01% Tween (PBT) and filtering through 40 μm cell strainers (Falcon, USA) to remove potential clumps and large particles. Cells can be incubated for 10 minutes with Fc receptor block (TruStain FcX, BioLegend, USA) to block non-specific antibody binding. Subsequently cells can be incubated in with mixtures of barcoded antibodies for 5-30 minutes at 4° C. Cells can be washed 1-3× by resuspension in PBS containing 2% BSA and 0.01% Tween, followed by centrifugation (~480×g 5 minutes) and supernatant exchange. After the final wash cells can be resuspended at appropriate cell concentration for library construction applications (e.g., Drop-seq, 10× Genomics, or split-pool applications).

In alternative embodiments, cells can be non-specifically labeled with DNA sample barcodes. For instance, primary amines or thiols of extracellular domains of membrane proteins can be labeled with click chemistry moieties (see, e.g., Niki'c et al., Labeling proteins on live mammalian cells using click chemistry. Nature protocols, 10(5):780-791, 2015; Chang, et al., Copper-free click chemistry in living animals. PNAS 2010 107 (5) 1821-1826; published ahead of print Jan. 14, 2010; Hong et al., Labeling Live Cells by Copper-Catalyzed Alkyne-Azide Click Chemistry. Bioconjug Chem. 2010 Oct. 20; 21(10): 1912-1916; Kolb, H. C., Finn, M. G. and Sharpless, K. B. (2001), Click Chemistry: Diverse Chemical Function from a Few Good Reactions. Angewandte Chemie International Edition, 40: 2004-2021; and Hoyle, Charles E. and Bowman, Christopher N. (2010), Thiol-Ene Click Chemistry. Angewandte Chemie International Edition, 49: 1540-1573), and in a staining step, oligonucleotides functionalized with compatible click chemistry groups can be covalently attached. In certain embodiments, copper-less click chemistry reagents may be used to label the surface of cells (e.g., Click-iT® DIBO-maleimide can be used to label thiols and Click-iT® DIBO-succinimidyl ester can be used to label primary amines).

In additional embodiments, one could biotinylate primary amines of extracellular domains of membrane proteins, and stain samples with monomeric avidin (see, e.g., Jeong Min Lee, et al., A rhizavidin monomer with nearly multimeric avidin-like binding stability against biotin conjugates. Angewandte Chemie International Edition, 55(10):3393-3397, 2016), or antibodies that recognize biotin (see, e.g., Udeshi, et al., Antibodies to biotin enable large-scale detection of biotinylation sites on proteins. Nature Methods, 2017) that are conjugated to DNA sample barcodes. This reaction would be non-specific, and efficient.

In certain embodiments, the surface of the cells is labeled with a biotin ester. Biotin-XX sulfosuccinimidyl ester is a cell-impermeant, amine-reactive compound that can be used to label proteins exposed on the surface of live cells (see, e.g., Cell-Surface Biotinylation Kit, ThermoFisher Scientific). The sulfosuccinidimidyl ester forms an extremely stable conjugate (Bioconjugate Chem 6, 447 (1995)) with cell-surface proteins, and the biotin provides a convenient hapten for subsequent analysis or binding with an avidin-based protein (e.g., linked to a sample barcode oligonucleotide), including streptavidin, NeutrAvidin or CaptAvidin biotin-binding proteins (Cell Biology: A Laboratory Handbook 2nd Edition, J. Celis, Ed., pp. 341-350, Academic Press (1998)) Cell-surface biotinylation techniques have been employed to differentially label proteins in the apical and basolateral plasma membranes of epithelial cells (J Neurochem 77, 1301 (2001); J Cell Sci 109, 3025 (1996)). The technique is also suited to the study of internalization of membrane proteins and cell-surface targeting of proteins (J Cell Biol 153, 957 (2001); J Virol 75, 4744 (2001); J Biol Chem 274, 36801 (1999)).

In certain embodiments, the sample barcode oligonucleotides are compatible with oligo dT-based RNA-sequencing library preparations so that they can be captured and sequenced together with mRNAs. In certain embodiments, the sample barcode oligonucleotide includes a poly A tail. In certain embodiments, a poly T oligo is used to capture mRNA and polyadenylated sample barcode oligonucleotides and prime a reverse transcription reaction to obtain cDNA molecules. Commonly used reverse transcriptases have DNA-dependent DNA polymerase activity. This activity allows DNA sample barcoding oligonucleotides to be copied into cDNA during reverse transcription. In certain embodiments, the sample barcode oligonucleotides comprise a PCR handle compatible with single cell sequencing methods as described herein (e.g., Drop-seq, InDrop, 10× Genomics). Depending on the application, the PCR-amplification handle in the sample barcode oligonucleotides can be changed depending on which sequence read is used for RNA readout (e.g. Drop-seq uses read 2, 10× v1 uses read 1). In certain embodiments, the sample barcode oligonucleotides comprise a PCR handle for amplification and next-generation sequencing library preparation, a barcode sequence specific for each sample, and a polyA stretch at the 3' end designed to anneal to polyT stretches on primers used to initiate reverse transcription. In certain embodiments, the sample barcode oligonucleotide comprises an UMI. In certain embodiments, random priming may be used for reverse transcription. The sample barcode oligonucleotides may be RNA or DNA. The sample barcode oligonucleotides may incorporate any modified nucleotides known in the art. In certain embodiments, the sample barcode oligonucleotides include a 3-20 nucleotide barcode sequence.

In certain embodiments, the multiplexing strategy can be applied to any membrane enclosed biological entity, such as membrane enclosed organelles, isolated nuclei, single-cells, and the like. In certain embodiments, organelle specific antibodies may be used.

In certain embodiments, the invention involves single cell RNA sequencing (see, e.g., Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA-Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq: Single-Cell RNA-Seq by Multiplexed Linear Amplification. Cell Reports, Cell Reports, Volume 2, Issue 3, p666-6'73, 2012).

In certain embodiments, the invention involves plate based single cell RNA sequencing (see, e.g., Picelli, S. et al., 2014, "Full-length RNA-seq from single cells using Smart-seq2" Nature protocols 9, 171-181, doi:10.1038/nprot.2014.006).

In certain embodiments, the invention involves high-throughput single-cell RNA-seq. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Rosenberg et al., "Single-cell profiling of the developing mouse brain and spinal cord with split-pool barcoding" Science 15 Mar. 2018; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

The multiplexing strategy described herein is also applicable to samples obtained by single nucleus sequencing and/or Div-seq (see, e.g., Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; and International patent application number PCT/US2016/059239, published as WO2017164936 on Sep. 28, 2017). In certain embodiments, nuclei are labeled chemically (e.g., Click chemistry, biotin) or with an antibody specific for a nuclear membrane protein (e.g., nuclear pore protein). Nuclear membrane proteins common to all nuclei include, but are not limited to Lamin-A, B or C, NUP98, NUP153, or NUP214.

In certain embodiments, the sample barcode is configured for addition of a handle compatible with split pool barcoding. In certain embodiments, reverse transcription is used to add an index barcode handle to the sample barcode oligonucleotide and to mRNA. Thus, the same cell of origin barcode sequence can be added to both mRNA and the sample barcode oligonucleotide using a split and pool method.

In certain embodiments, tagmentation is used to introduce adaptor sequences to genomic DNA in regions of accessible chromatin (e.g., between individual nucleosomes) (see, e.g., US20160208323A1; US20160060691A1; WO2017156336A1; J. D. Buenrostro et al., Single-cell chromatin accessibility reveals principles of regulatory variation. Nature 523, 486-490 (2015); and Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. Science. 2015 May 22;348 (6237):910-4. doi: 10.1126/science.aab1601. Epub 2015 May 7). The term "tagmentation" refers to a step in the Assay for Transposase Accessible Chromatin using sequencing (ATAC-seq) as described. (See, Buenrostro, J. D., Giresi, P. G., Zaba, L. C., Chang, H. Y., Greenleaf, W. J., Transposition of native chromatin for fast and sensitive epigenomic profiling of open chromatin, DNA-binding proteins and nucleosome position. Nature methods 2013; 10 (12): 1213-1218). Specifically, a hyperactive Tn5 transposase loaded in vitro with adapters for high-throughput DNA sequencing, can simultaneously fragment and tag a genome with sequencing adapters. In one embodiment the adapters are compatible with the methods described herein.

The multiplexing strategy described herein is also applicable to single-cell profiling of chromatin accessibility (see, e.g., Cusanovich, et al., 2015; and www.10xgenomics.com/solutions/single-cell-atac/). In certain embodiments, a handle is attached to the adapters, such that the tagmented DNA acts as an artificial mRNA (e.g., poly A tail) and can be captured by a cell of origin barcode poly dT capture sequence. In certain embodiments, the sample barcode oligonucleotides are adapted for tagmentation with the adapters used in the first step of generating cell of origin barcodes.

The multiplexing strategy described herein is also applicable to single-cell profiling of surface proteins and gene expression. For example, CITE-seq (Stoeckius et al., 2017) can be used, such that barcoded surface protein specific antibodies receive a cell of origin barcode as described herein. In certain embodiments, antibodies specific to nuclear proteins not on the surface are used to determine nuclear protein expression.

In certain embodiments, targeted gene expression is determined using fluorescence in situ hybridization (FISH) probes that are capable of being labeled with the cell of origin barcode. In certain embodiments, the probes are amplified by PCR to add the cell of origin barcode (e.g., primers having a cell of origin barcode or a handle for generating a barcode for split pool). The primers can be provided by a bead. The bead can be provided to a droplet, microwell, microfluidic chamber, or a well. The sample barcode can be configured for amplification in the same way as the probe to add the cell of origin barcode. FISH probes may be as described for Flow FISH, but modified to be amplified by PCR with primers comprising a cell of origin barcode.

Flow FISH provides for detecting marker genes using gene specific probes and sorting the cells. In certain embodiments, multiple markers are used to increase specificity. Selecting for multiple reporter genes at the same time can narrow down target cell types because usually one gene is not specific enough depending on the target cell type. Additionally, the assay is versatile in that reporter genes can be added or changed by applying different probes. Flow FISH combines FISH to fluorescently label mRNA of reporter genes and flow cytometry (see, e.g., Arrigucci et al., FISH-Flow, a protocol for the concurrent detection of mRNA and protein in single cells using fluorescence in situ hybridization and flow cytometry, Nat Protoc. 2017 June; 12(6):1245-1260. doi:10.1038/nprot.2017.039). In certain embodiments, specific nuclei are enriched for using fluorescent probes. The probes can be as described for Flow FISH. Specifically, Applicants fluorescently label mRNA of reporter genes and select for target cell types by flow cytometry. In certain embodiments, the marker genes are selected, such that they are specifically expressed only in the target cell. In this way, false positive selection or background is avoided. The assay is also optimized to remove background fluorescence and to select for true positive cells.

In certain embodiments, multiplexing may be used in single cell proteomics as discussed herein or in other protocols (see e.g., WO2012106385A2). In certain embodiments, cells or fixed cells are labeled (e.g., antibody, click chemistry, biotin-avidin) with a sample barcode oligonucleotide compatible (e.g., handle) with a cell of origin barcoding strategy as described herein (e.g., split and pool).

In one exemplary embodiment, samples for use in droplet based single sequencing as described herein are multiplexed. Cells belonging to different samples are labeled with sample barcode oligonucleotides as described herein. The single cells from multiple samples may then be loaded into a microfluidic device. The labeled cells are encapsulated with reagents and cell of origin barcode containing beads in emulsion droplets. The sample barcode oligonucleotide may then be released from the cell in the droplet (e.g., by lysis of the cell or reducing conditions in the droplet) and processed to generate a cDNA molecule comprising the sample barcode and cell of origin barcode. Since every cDNA molecule (i.e., derived from mRNA and sample barcode oligonucleotide) from a single cell includes the same cell of origin barcode, the sequencing data can be demultiplexed to determine the cell and sample of origin.

In another exemplary embodiment, single cell analysis uses split and pool barcoding. In certain embodiments, split and pool barcoding requires the cells or nuclei to be fixed. In certain embodiments, the label needs to remain bound to the cells during the split and pool steps. In certain embodiments, cells are labeled with sample barcode oligonucleotides (e.g., oligo-linked antibodies, chemical means or biotin-avidin binding). In certain embodiments, the cells in different samples are fixed and permeabilized. The cells are then labeled with a sample barcode oligonucleotide as described herein. Fixation may be by methanol fixation or aldehyde fixation (e.g., formaldehyde, paraformaldehyde, glutaraldehyde). In certain embodiments, the labeled cells are pooled and in situ reverse transcription is performed, thus cDNA is obtained for mRNA and the sample barcode oligonucleotides. The cells from all samples are split into pools for labeling with a first barcode. The split and pool process may be repeated any number of "n" times to ensure each cell has a unique barcode sequence. The last barcode may include an UMI and a PCR handle.

In certain embodiments, the cells in different samples are fixed and permeabilized. The cells are then labeled with a sample barcode oligonucleotide as described herein. The cells from all samples are split into pools. In situ reverse transcription is then performed in the pools to introduce a first barcode sequence to the mRNA and sample barcode oligonucleotides. The cells may be pooled again and split into second pools. Second strand synthesis, tagmentation and PCR may be performed to add a second barcode sequence to the cDNA.

In certain embodiments, quantitative real time PCR is utilized. Detection of the gene expression level can be conducted in real time in an amplification assay. In one aspect, the amplified products can be directly visualized with fluorescent DNA-binding agents including but not limited to DNA intercalators and DNA groove binders. Because the amount of the intercalators incorporated into the double-stranded DNA molecules is typically proportional to the amount of the amplified DNA products, one can conveniently determine the amount of the amplified products by quantifying the fluorescence of the intercalated dye using conventional optical systems in the art. DNA-binding dye suitable for this application include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, and the like.

In another aspect, other fluorescent labels such as sequence specific probes can be employed in the amplification reaction to facilitate the detection and quantification of the amplified products. Probe-based quantitative amplification relies on the sequence-specific detection of a desired amplified product. It utilizes fluorescent, target-specific probes (e.g., TaqMan® probes) resulting in increased specificity and sensitivity. Methods for performing probe-based quantitative amplification are well established in the art and are taught in U.S. Pat. No. 5,210,015.

Perturb-seq and Flow Enrichment
Perturb-seq

Methods and tools for genome-scale screening of perturbations in single cells using CRISPR-Cas9 have been described, herein referred to as perturb-seq (see e.g., Dixit et al., "Perturb-Seq: Dissecting Molecular Circuits with Scalable Single-Cell RNA Profiling of Pooled Genetic Screens" 2016, Cell 167, 1853-1866; Adamson et al., "A Multiplexed Single-Cell CRISPR Screening Platform Enables Systematic Dissection of the Unfolded Protein Response" 2016, Cell 167, 1867-1882; Feldman et al., Lentiviral co-packaging mitigates the effects of intermolecular recombination and multiple integrations in pooled genetic screens, bioRxiv 262121, doi: doi.org/10.1101/262121; Datlinger, et al., 2017, Pooled CRISPR screening with single-cell transcriptome readout. Nature Methods. Vol. 14 No. 3 DOI: 10.1038/nmeth.4177; Hill et al., On the design of CRISPR-based single cell molecular screens, Nat Methods. 2018 April; 15(4): 271-274; and International publication serial number WO/2017/075294).

Figure 16:
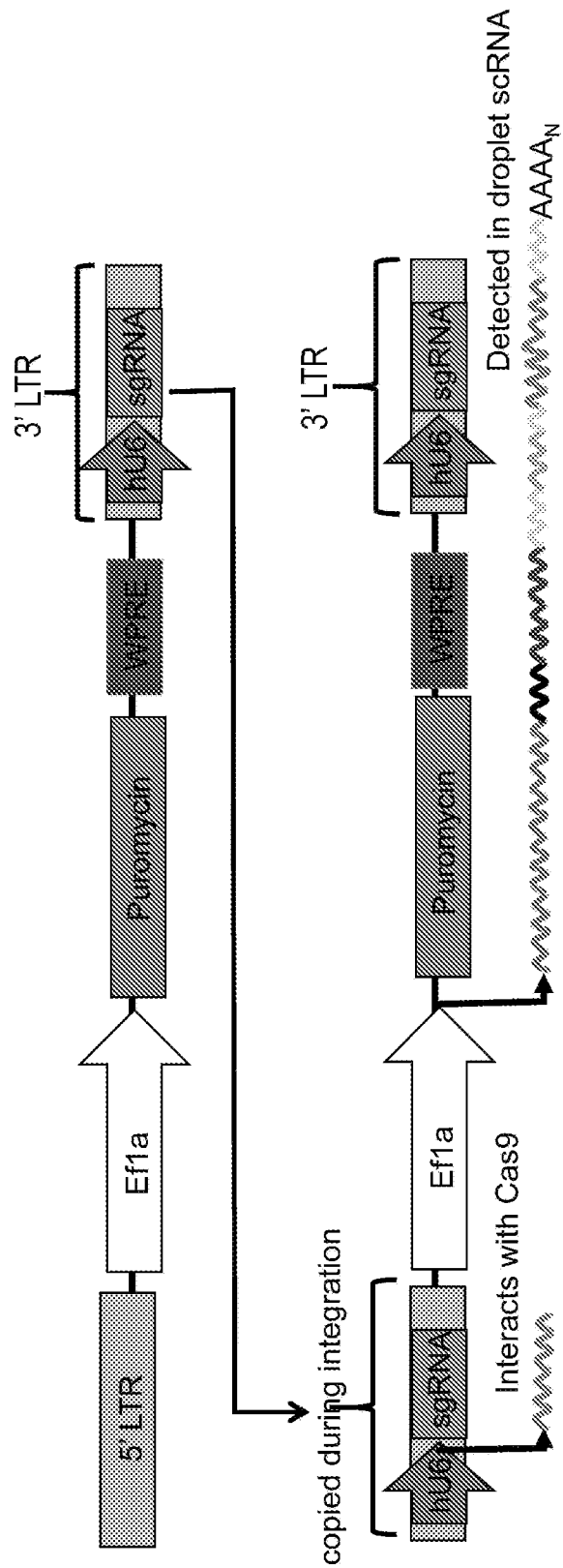
FIG. 16—Illustrates scRNA-seq and perturb-seq using the CROP-seq vector.

The perturbation methods and tools allow reconstructing of a cellular network or circuit. In one embodiment, the method comprises (1) introducing single-order or combinatorial perturbations to a population of cells, (2) measuring genomic, genetic, proteomic, epigenetic and/or phenotypic differences in single cells and (3) assigning a perturbation(s) to the single cells. Not being bound by a theory, a perturbation may be linked to a phenotypic change, preferably changes in gene or protein expression. In preferred embodiments, measured differences that are relevant to the perturbations are determined by applying a model accounting for co-variates to the measured differences. The model may include the capture rate of measured signals, whether the perturbation actually perturbed the cell (phenotypic impact), the presence of subpopulations of either different cells or cell states, and/or analysis of matched cells without any perturbation. In certain embodiments, the measuring of phenotypic differences and assigning a perturbation to a single cell is determined by performing single cell RNA sequencing (RNA-seq). In preferred embodiments, the single cell RNA-seq is performed by any method as described herein (e.g., Drop-seq, InDrop, 10× genomics). In certain embodiments, unique barcodes are used to perform Perturb-seq. In certain embodiments, a guide RNA is detected by RNA-seq using a transcript expressed from a vector encoding the guide RNA. The transcript may include a unique barcode specific to the guide RNA. The transcript may include the guide RNA sequence (see, e.g., FIG. 16, CROP-seq, Datlinger, et al., 2017). In certain embodiments, a guide RNA and guide RNA barcode is expressed from the same vector and the barcode may be detected by RNA-seq. Not being bound by a theory, detection of a guide RNA barcode is more reliable than detecting a guide RNA sequence, reduces the chance of false guide RNA assignment and reduces the sequencing cost associated with executing these screens. Thus, a perturbation may be assigned to a single cell by detection of a guide RNA barcode in the cell. In certain embodiments, a cell barcode is added to the RNA in single cells, such that the RNA may be assigned to a single cell. Generating cell barcodes is described herein for single cell sequencing methods. In certain embodiments, a Unique Molecular Identifier (UMI) is added to each individual transcript and protein capture oligonucleotide. Not being bound by a theory, the UMI allows for determining the capture rate of measured signals, or preferably the binding events or the number of transcripts captured. Not being bound by a theory, the data is more significant if the signal observed is derived from more than one protein binding event or transcript. In preferred embodiments, Perturb-seq is performed using a guide RNA barcode expressed as a polyadenylated transcript, a cell barcode, and a UMI.

Perturb-seq combines emerging technologies in the field of genome engineering, single-cell analysis and immunology, in particular the CRISPR-Cas9 system and droplet single-cell sequencing analysis. In certain embodiments, a CRISPR system is used to create an INDEL at a target gene. In other embodiments, epigenetic screening is performed by applying CRISPRa/i/x technology (see, e.g., Konermann et al. "Genome-scale transcriptional activation by an engineered CRISPR-Cas9 complex" Nature. 2014 Dec. 10. doi: 10.1038/nature14136; Qi, L. S., et al. (2013). "Repurposing CRISPR as an RNA-guided platform for sequence-specific control of gene expression". Cell. 152 (5): 1173-83; Gilbert, L. A., et al., (2013). "CRISPR-mediated modular RNA-guided regulation of transcription in eukaryotes". Cell. 154 (2): 442-51; Komor et al., 2016, Programmable editing of a target base in genomic DNA without double-stranded DNA cleavage, Nature 533, 420-424; Nishida et al., 2016, Targeted nucleotide editing using hybrid prokaryotic and vertebrate adaptive immune systems, Science 353(6305); Yang et al., 2016, Engineering and optimising deaminase fusions for genome editing, Nat Commun. 7:13330; Hess et al., 2016, Directed evolution using dCas9-targeted somatic hypermutation in mammalian cells, Nature Methods 13, 1036-1042; and Ma et al., 2016, Targeted AID-mediated mutagenesis (TAM) enables efficient genomic diversification in mammalian cells, Nature Methods 13, 1029-1035). Numerous genetic variants associated with disease phenotypes are found to be in non-coding region of the genome, and frequently coincide with transcription factor (TF) binding sites and non-coding RNA genes. Not being bound by a theory, CRISPRa/i/x approaches may be used to achieve a more thorough and precise understanding of the implication of epigenetic regulation. In one embodiment, a CRISPR system may be used to activate gene transcription. A nuclease-dead RNA-guided DNA binding domain, dCas9, tethered to transcriptional repressor domains that promote epigenetic silencing (e.g., KRAB) may be used for "CRISPRi" that represses transcription. To use dCas9 as an activator (CRISPRa), a guide RNA is engineered to carry RNA binding motifs (e.g., MS2) that recruit effector domains fused to RNA-motif binding proteins, increasing transcription. A key dendritic cell molecule, p65, may be used as a signal amplifier, but is not required.

In certain embodiments, other CRISPR-based perturbations are readily compatible with Perturb-seq, including alternative editors such as CRISPR/Cpf1. In certain embodiments, Perturb-seq uses Cpf1 as the CRISPR enzyme for introducing perturbations. Not being bound by a theory, Cpf1 does not require Tracr RNA and is a smaller enzyme, thus allowing higher combinatorial perturbations to be tested.

The cell(s) may comprise a cell in a model non-human organism, a model non-human mammal that expresses a Cas protein, a mouse that expresses a Cas protein, a mouse that expresses Cpf1, a cell in vivo or a cell ex vivo or a cell in vitro (see e.g., WO 2014/093622 (PCT/US13/074667); US Patent Publication Nos. 20120017290 and 20110265198 assigned to Sangamo BioSciences, Inc.; US Patent Publication No. 20130236946 assigned to Cellectis; Platt et al., "CRISPR-Cas9 Knockin Mice for Genome Editing and Cancer Modeling" Cell (2014), 159(2): 440-455; "Oncogenic models based on delivery and use of the crispr-cas systems, vectors and compositions" WO2014204723A1 "Delivery and use of the crispr-cas systems, vectors and compositions for hepatic targeting and therapy" WO2014204726A1; "Delivery, use and therapeutic applications of the crispr-cas systems and compositions for modeling mutations in leukocytes" WO2016049251; and Chen et al., "Genome-wide CRISPR Screen in a Mouse Model of Tumor Growth and Metastasis" 2015, Cell 160, 1246-1260). The cell(s) may also comprise a human cell. Mouse cell lines may include, but are not limited to neuro-2a cells and EL4 cell lines (ATCC TIB-39). Primary mouse T cells may be isolated from C57/BL6 mice. Primary mouse T cells may be isolated from Cas9-expressing mice.

In one embodiment, CRISPR/Cas9 may be used to perturb protein-coding genes or non-protein-coding DNA. CRISPR/Cas9 may be used to knockout protein-coding genes by frameshifts, point mutations, inserts, or deletions. An extensive toolbox may be used for efficient and specific CRISPR/Cas9 mediated knockout as described herein, including a double-nicking CRISPR to efficiently modify both alleles of a target gene or multiple target loci and a smaller Cas9 protein for delivery on smaller vectors (Ran, F. A., et al., In vivo genome editing using *Staphylococcus aureus* Cas9. Nature. 520, 186-191 (2015)). A genome-wide sgRNA mouse library (~10 sgRNAs/gene) may also be used in a mouse that expresses a Cas9 protein (see, e.g., WO2014204727A1).

In one embodiment, perturbation is by deletion of regulatory elements. Non-coding elements may be targeted by using pairs of guide RNAs to delete regions of a defined size, and by tiling deletions covering sets of regions in pools.

In one embodiment, perturbation of genes is by RNAi. The RNAi may be shRNA's targeting genes. The shRNA's may be delivered by any methods known in the art. In one embodiment, the shRNA's may be delivered by a viral vector. The viral vector may be a lentivirus, adenovirus, or adeno associated virus (AAV).

A CRISPR system may be delivered to primary mouse T-cells. Over 80% transduction efficiency may be achieved with Lenti-CRISPR constructs in CD4 and CD8 T-cells. Despite success with lentiviral delivery, recent work by Hendel et al, (Nature Biotechnology 33, 985-989 (2015) doi:10.1038/nbt.3290) showed the efficiency of editing human T-cells with chemically modified RNA, and direct RNA delivery to T-cells via electroporation. In certain embodiments, perturbation in mouse primary T-cells may use these methods.

In certain embodiments, whole genome screens can be used for understanding the phenotypic readout of perturbing potential target genes. In preferred embodiments, perturbations target expressed genes as defined by a gene signature using a focused sgRNA library. Libraries may be focused on expressed genes in specific networks or pathways. In other preferred embodiments, regulatory drivers are perturbed. In certain embodiments, Applicants perform systematic perturbation of key genes that regulate T-cell function in a high-throughput fashion. In certain embodiments, Applicants perform systematic perturbation of key genes that regulate cancer cell function in a high-throughput fashion (e.g., immune resistance or immunotherapy resistance). Applicants can use gene expression profiling data to define the target of interest and perform follow-up single-cell and population RNA-seq analysis. Not being bound by a theory, this approach will accelerate the development of therapeutics for human disorders, in particular cancer. Not being bound by a theory, this approach will enhance the understanding of the biology of T-cells and tumor immunity, and accelerate the development of therapeutics for human disorders, in particular cancer, as described herein.

Not being bound by a theory, perturbation studies targeting the genes and gene signatures described herein could (1) generate new insights regarding regulation and interaction of molecules within the system that contribute to suppression of an immune response, such as in the case within the tumor microenvironment, and (2) establish potential therapeutic targets or pathways that could be translated into clinical application.

In certain embodiments, after determining Perturb-seq effects in cancer cells and/or primary T-cells, the cells are infused back to the tumor xenograft models (melanoma, such as B16F10 and colon cancer, such as CT26) to observe the phenotypic effects of genome editing. Not being bound by a theory, detailed characterization can be performed based on (1) the phenotypes related to tumor progression, tumor growth, immune response, etc. (2) the TILs that have been genetically perturbed by CRISPR-Cas9 can be isolated from tumor samples, subject to cytokine profiling, qPCR/RNA-seq, and single-cell analysis to understand the biological effects of perturbing the key driver genes within the tumor-immune cell contexts. Not being bound by a theory, this will lead to validation of TILs biology as well as lead to therapeutic targets.

In one aspect, the present invention provides for a method of reconstructing a cellular network or circuit, comprising introducing at least 1, 2, 3, 4 or more single-order or combinatorial perturbations to a plurality of cells in a population of cells, wherein each cell in the plurality of the cells receives at least 1 perturbation; measuring comprising: detecting genomic, genetic, proteomic, epigenetic and/or phenotypic differences in single cells compared to one or more cells that did not receive any perturbation, and detecting the perturbation(s) in single cells; and determining measured differences relevant to the perturbations by applying a model accounting for co-variates to the measured differences, whereby intercellular and/or intracellular networks or circuits are inferred. The measuring in single cells may comprise single cell sequencing. The single cell sequencing may comprise cell barcodes, whereby the cell-of-origin of each RNA is recorded. The single cell sequencing may comprise unique molecular identifiers (UMI), whereby the capture rate of the measured signals, such as transcript copy number or probe binding events, in a single cell is determined. The model may comprise accounting for the capture rate of measured signals, whether the perturbation actually perturbed the cell (phenotypic impact), the presence of subpopulations of either different cells or cell states, and/or analysis of matched cells without any perturbation.

The single-order or combinatorial perturbations may comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 perturbations. The perturbation(s) may target genes in a pathway or intracellular network.

The measuring may comprise detecting the transcriptome of each of the single cells. The perturbation(s) may comprise one or more genetic perturbation(s). The perturbation(s) may comprise one or more epigenetic or epigenomic perturbation(s). At least one perturbation may be introduced with RNAi- or a CRISPR-Cas system. At least one perturbation may be introduced via a chemical agent, biological agent, an intracellular spatial relationship between two or more cells, an increase or decrease of temperature, addition or subtraction of energy, electromagnetic energy, or ultrasound.

The cell(s) may comprise a cell in a model non-human organism, a model non-human mammal that expresses a Cas protein, a mouse that expresses a Cas protein, a mouse that expresses Cpf1, a cell in vivo or a cell ex vivo or a cell in vitro. The cell(s) may also comprise a human cell.

The measuring or measured differences may comprise measuring or measured differences of DNA, RNA, protein or post translational modification; or measuring or measured differences of protein or post translational modification correlated to RNA and/or DNA level(s).

The perturbing or perturbation(s) may comprise(s) genetic perturbing. The perturbing or perturbation(s) may comprise(s) single-order perturbations. The perturbing or perturbation(s) may comprise(s) combinatorial perturbations. The perturbing or perturbation(s) may comprise gene knock-down, gene knock-out, gene activation, gene insertion, or regulatory element deletion. The perturbing or perturbation(s) may comprise genome-wide perturbation. The perturbing or perturbation(s) may comprise performing CRISPR-Cas-based perturbation. The perturbing or perturbation(s) may comprise performing pooled single or combinatorial CRISPR-Cas-based perturbation with a genomewide library of sgRNAs. The perturbations may be of a selected group of targets based on similar pathways or network of targets.

The perturbing or perturbation(s) may comprises performing pooled combinatorial CRISPR-Cas-based perturbation with a genome-wide library of sgRNAs. Each sgRNA may be associated with a unique perturbation barcode. Each sgRNA may be co-delivered with a reporter mRNA comprising the unique perturbation barcode (or sgRNA perturbation barcode).

The perturbing or perturbation(s) may comprise subjecting the cell to an increase or decrease in temperature. The perturbing or perturbation(s) may comprise subjecting the cell to a chemical agent. The perturbing or perturbation(s) may comprise subjecting the cell to a biological agent. The biological agent may be a toll like receptor agonist or cytokine. The perturbing or perturbation(s) may comprise subjecting the cell to a chemical agent, biological agent and/or temperature increase or decrease across a gradient.

The cell may be in a microfluidic system. The cell may be in a droplet. The population of cells may be sequenced by using microfluidics to partition each individual cell into a droplet containing a unique barcode, thus allowing a cell barcode to be introduced.

The perturbing or perturbation(s) may comprise transforming or transducing the cell or a population that includes and from which the cell is isolated with one or more genomic sequence-perturbation constructs that perturbs a genomic sequence in the cell. The sequence-perturbation construct may be a viral vector, preferably a lentivirus vector. The perturbing or perturbation(s) may comprise multiplex transformation or transduction with a plurality of genomic sequence-perturbation constructs.

Sorting Cells or Nuclei

In certain embodiments, single cells or nuclei are enriched by FACS or magnetic-activated cell sorting (MACS). The nuclei or cells of any method described herein may further be detectable by a fluorescent signal, whereby individual nuclei or cells may be further sorted. The single nuclei or cells may be immunostained with an antibody with specific affinity for an intranuclear protein or cell surface protein. The antibody may be specific for NeuN. The nuclei may be stained with a nuclear stain. The nuclear stain may comprise DAPI, Ruby red, trypan blue, Hoechst or propidium iodine. In certain embodiments, nuclei can be labeled with ruby dye (Thermo Fisher Scientific, Vybrant DyeCycle Ruby Stain, #V-10309).

The term "protein" as used throughout this specification generally encompasses macromolecules comprising one or more polypeptide chains, i.e., polymeric chains of amino acid residues linked by peptide bonds. The term may encompass naturally, recombinantly, semi-synthetically or synthetically produced proteins. The term also encompasses proteins that carry one or more co- or post-expression-type modifications of the polypeptide chain(s), such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes protein variants or mutants which carry amino acid sequence variations vis-à-vis a corresponding native protein, such as, e.g., amino acid deletions, additions and/or substitutions. The term contemplates both full-length proteins and protein parts or fragments, e.g., naturally-occurring protein parts that ensue from processing of such full-length proteins.

The reference to any marker, including any peptide, polypeptide, protein, or nucleic acid, corresponds to the marker commonly known under the respective designations in the art. The terms encompass such markers of any organism where found, and particularly of animals, preferably warm-blooded animals, more preferably vertebrates, yet more preferably mammals, including humans and non-human mammals, still more preferably of humans.

The terms particularly encompass such markers, including any peptides, polypeptides, proteins, or nucleic acids, with a native sequence, i.e., ones of which the primary sequence is the same as that of the markers found in or derived from nature. A skilled person understands that native sequences may differ between different species due to genetic divergence between such species. Moreover, native sequences may differ between or within different individuals of the same species due to normal genetic diversity (variation) within a given species. Also, native sequences may differ between or even within different individuals of the same species due to somatic mutations, or post-transcriptional or post-translational modifications. Any such variants or isoforms of markers are intended herein. Accordingly, all sequences of markers found in or derived from nature are considered "native". The terms encompass the markers when forming a part of a living organism, organ, tissue or cell, when forming a part of a biological sample, as well as when at least partly isolated from such sources. The terms also encompass markers when produced by recombinant or synthetic means.

In certain embodiments, markers, including any peptides, polypeptides, proteins, or nucleic acids, may be human, i.e., their primary sequence may be the same as a corresponding primary sequence of or present in a naturally occurring human markers. Hence, the qualifier "human" in this connection relates to the primary sequence of the respective markers, rather than to their origin or source. For example, such markers may be present in or isolated from samples of human subjects or may be obtained by other means (e.g., by recombinant expression, cell-free transcription or translation, or non-biological nucleic acid or peptide synthesis).

The reference herein to any marker, including any peptide, polypeptide, protein, or nucleic acid, also encompasses fragments thereof. Hence, the reference herein to measuring (or measuring the quantity of) any one marker may encompass measuring the marker and/or measuring one or more fragments thereof.

For example, any marker and/or one or more fragments thereof may be measured collectively, such that the measured quantity corresponds to the sum amounts of the collectively measured species. In another example, any marker and/or one or more fragments thereof may be measured each individually. The terms encompass fragments arising by any mechanism, in vivo and/or in vitro, such as, without limitation, by alternative transcription or translation, exo- and/or endo-proteolysis, exo- and/or endo-nucleolysis, or degradation of the peptide, polypeptide, protein, or nucleic acid, such as, for example, by physical, chemical and/or enzymatic proteolysis or nucleolysis.

The term "fragment" as used throughout this specification with reference to a peptide, polypeptide, or protein generally denotes a portion of the peptide, polypeptide, or protein, such as typically an N- and/or C-terminally truncated form of the peptide, polypeptide, or protein. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the amino acid sequence length of said peptide, polypeptide, or protein. For example, insofar not exceeding the length of the full-length peptide, polypeptide, or protein, a fragment may include a sequence of ≥5 consecutive amino acids, or ≥10 consecutive amino acids, or ≥20 consecutive amino acids, or ≥30 consecutive amino acids, e.g., ≥40 consecutive amino acids, such as for example ≥50 consecutive amino acids, e.g., ≥60, ≥70, ≥80, ≥90, ≥100, ≥200, ≥300, ≥400, ≥500 or ≥600 consecutive amino acids of the corresponding full-length peptide, polypeptide, or protein.

The term "fragment" as used throughout this specification with reference to a nucleic acid (polynucleotide) generally denotes a 5'- and/or 3'-truncated form of a nucleic acid. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the nucleic acid sequence length of said nucleic acid. For example, insofar not exceeding the length of the full-length nucleic acid, a fragment may include a sequence of ≥5 consecutive nucleotides, or ≥10 consecutive nucleotides, or ≥20 consecutive nucleotides, or ≥30 consecutive nucleotides, e.g., ≥40 consecutive nucleotides, such as for example ≥50 consecutive nucleotides, e.g., ≥60, ≥70, ≥80, ≥90, ≥100, ≥200, ≥300, ≥400, ≥500 or ≥600 consecutive nucleotides of the corresponding full-length nucleic acid.

Cells such as immune cells as disclosed herein may in the context of the present specification be said to "comprise the expression" or conversely to "not express" one or more markers, such as one or more genes or gene products; or be described as "positive" or conversely as "negative" for one or more markers, such as one or more genes or gene products; or be said to "comprise" a defined "gene or gene product signature".

Such terms are commonplace and well-understood by the skilled person when characterizing cell phenotypes. By means of additional guidance, when a cell is said to be positive for or to express or comprise expression of a given marker, such as a given gene or gene product, a skilled person would conclude the presence or evidence of a distinct signal for the marker when carrying out a measurement capable of detecting or quantifying the marker in or on the cell. Suitably, the presence or evidence of the distinct signal for the marker would be concluded based on a comparison of the measurement result obtained for the cell to a result of the same measurement carried out for a negative control (for example, a cell known to not express the marker) and/or a positive control (for example, a cell known to express the marker). Where the measurement method allows for a quantitative assessment of the marker, a positive cell may generate a signal for the marker that is at least 1.5-fold higher than a signal generated for the marker by a negative control cell or than an average signal generated for the marker by a population of negative control cells, e.g., at least 2-fold, at least 4-fold, at least 10-fold, at least 20-fold, at least 30-fold, at least 40-fold, at least 50-fold higher or even higher. Further, a positive cell may generate a signal for the marker that is 3.0 or more standard deviations, e.g., 3.5 or more, 4.0 or more, 4.5 or more, or 5.0 or more standard deviations, higher than an average signal generated for the marker by a population of negative control cells.

Binding Agents

In certain embodiments, any binding agent can be used to bind a target protein for labeling cells with a hashtag or sample barcode (e.g., antibodies, aptamers).

Antibodies

The term "antibody" is used interchangeably with the term "immunoglobulin" herein, and includes intact antibodies, fragments of antibodies, e.g., Fab, F(ab')2 fragments, and intact antibodies and fragments that have been mutated either in their constant and/or variable region (e.g., mutations to produce chimeric, partially humanized, or fully humanized antibodies, as well as to produce antibodies with a desired trait, e.g., enhanced binding and/or reduced FcR binding). The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc, Fd, dAb, $V_{HH}$ and scFv and/or Fv fragments.

As used herein, a preparation of antibody protein having less than about 50% of non-antibody protein (also referred to herein as a "contaminating protein"), or of chemical precursors, is considered to be "substantially free." 40%, 30%, 20%, 10% and more preferably 5% (by dry weight), of non-antibody protein, or of chemical precursors is considered to be substantially free. When the antibody protein or biologically active portion thereof is recombinantly produced, it is also preferably substantially free of culture medium, i.e., culture medium represents less than about 30%, preferably less than about 20%, more preferably less than about 10%, and most preferably less than about 5% of the volume or mass of the protein preparation.

The term "antigen-binding fragment" refers to a polypeptide fragment of an immunoglobulin or antibody that binds antigen or competes with intact antibody (i.e., with the intact antibody from which they were derived) for antigen binding (i.e., specific binding). As such these antibodies or fragments thereof are included in the scope of the invention, provided that the antibody or fragment binds specifically to a target molecule.

It is intended that the term "antibody" encompass any Ig class or any Ig subclass (e.g. the IgG1, IgG2, IgG3, and IgG4 subclassess of IgG) obtained from any source (e.g., humans and non-human primates, and in rodents, lagomorphs, caprines, bovines, equines, ovines, etc.).

The term "Ig class" or "immunoglobulin class", as used herein, refers to the five classes of immunoglobulin that have been identified in humans and higher mammals, IgG, IgM, IgA, IgD, and IgE. The term "Ig subclass" refers to the two subclasses of IgM (H and L), three subclasses of IgA (IgA1, IgA2, and secretory IgA), and four subclasses of IgG (IgG1, IgG2, IgG3, and IgG4) that have been identified in humans and higher mammals. The antibodies can exist in monomeric or polymeric form; for example, 1 gM antibodies exist in pentameric form, and IgA antibodies exist in monomeric, dimeric or multimeric form.

The term "IgG subclass" refers to the four subclasses of immunoglobulin class IgG-IgG1, IgG2, IgG3, and IgG4 that have been identified in humans and higher mammals by the heavy chains of the immunoglobulins, V1-γ4, respectively. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains). The "variable" domains of an antibody light chain are referred to interchangeably as "light chain variable regions", "light chain variable domains", "VL" regions or "VL" domains). The "variable" domains of an antibody heavy chain are referred to interchangeably as "heavy chain constant regions", "heavy chain constant domains", "VH" regions or "VH" domains).

The term "region" can also refer to a part or portion of an antibody chain or antibody chain domain (e.g., a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein.

The term "conformation" refers to the tertiary structure of a protein or polypeptide (e.g., an antibody, antibody chain, domain or region thereof). For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof.

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from nonimmunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (10Fn3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins—harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

"Specific binding" of an antibody means that the antibody exhibits appreciable affinity for a particular antigen or epitope and, generally, does not exhibit significant cross reactivity. "Appreciable" binding includes binding with an affinity of at least 25 µM. Antibodies with affinities greater than $1 \times 10^7$ $M^{-1}$ (or a dissociation coefficient of 1 µM or less or a dissociation coefficient of 1 nm or less) typically bind with correspondingly greater specificity. Values intermediate of those set forth herein are also intended to be within the scope of the present invention and antibodies of the invention bind with a range of affinities, for example, 100 nM or less, 75 nM or less, 50 nM or less, 25 nM or less, for example 10 nM or less, 5 nM or less, 1 nM or less, or in embodiments 500 pM or less, 100 pM or less, 50 pM or less or 25 pM or less. An antibody that "does not exhibit significant crossreactivity" is one that will not appreciably bind to an entity other than its target (e.g., a different epitope or a different molecule). For example, an antibody that specifically binds to a target molecule will appreciably bind the target molecule but will not significantly react with non-target molecules or peptides. An antibody specific for a particular epitope will, for example, not significantly cross-react with remote epitopes on the same protein or peptide. Specific binding can be determined according to any art-recognized means for determining such binding. Preferably, specific binding is determined according to Scatchard analysis and/or competitive binding assays.

As used herein, the term "affinity" refers to the strength of the binding of a single antigen-combining site with an antigenic determinant. Affinity depends on the closeness of stereochemical fit between antibody combining sites and antigen determinants, on the size of the area of contact between them, on the distribution of charged and hydrophobic groups, etc. Antibody affinity can be measured by equilibrium dialysis or by the kinetic BIACORE™ method. The dissociation constant, Kd, and the association constant, Ka, are quantitative measures of affinity.

As used herein, the term "monoclonal antibody" refers to an antibody derived from a clonal population of antibody-producing cells (e.g., B lymphocytes or B cells) which is homogeneous in structure and antigen specificity. The term "polyclonal antibody" refers to a plurality of antibodies originating from different clonal populations of antibody-producing cells which are heterogeneous in their structure and epitope specificity but which recognize a common antigen. Monoclonal and polyclonal antibodies may exist within bodily fluids, as crude preparations, or may be purified, as described herein.

The term "binding portion" of an antibody (or "antibody portion") includes one or more complete domains, e.g., a pair of complete domains, as well as fragments of an antibody that retain the ability to specifically bind to a target molecule. It has been shown that the binding function of an antibody can be performed by fragments of a full-length antibody. Binding fragments are produced by recombinant DNA techniques, or by enzymatic or chemical cleavage of intact immunoglobulins. Binding fragments include Fab, Fab', F(ab')2, Fabc, Fd, dAb, Fv, single chains, single-chain antibodies, e.g., scFv, and single domain antibodies.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

Examples of portions of antibodies or epitope-binding proteins encompassed by the present definition include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the $C_H1$ domain; (v) the Fv fragment having the $V_L$ and $V_H$ domains of a single arm of an antibody; (vi) the dAb fragment (Ward et al., 341 Nature 544 (1989)) which consists of a $V_H$ domain or a $V_L$ domain that binds antigen; (vii) isolated CDR regions or isolated CDR regions presented in a functional framework; (viii) F(ab')$_2$ fragments which are bivalent fragments including two Fab' fragments linked by a disulphide bridge at the hinge region; (ix) single chain antibody molecules (e.g., single chain Fv; scFv) (Bird et al., 242 Science 423 (1988); and Huston et al., 85 PNAS 5879 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; Hollinger et al., 90 PNAS 6444 (1993)); (xi) "linear antibodies" comprising a pair of tandem Fd segments ($V_H$-$C_h1$-$V_H$-$C_h1$) which, together with complementary light chain polypeptides, form a pair of antigen binding regions (Zapata et al., Protein Eng. 8(10): 1057-62 (1995); and U.S. Pat. No. 5,641,870).

The antibodies as defined for the present invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Simple binding assays can be used to screen for or detect agents that bind to a target protein, or disrupt the interaction between proteins (e.g., a receptor and a ligand). Because certain targets of the present invention are transmembrane proteins, assays that use the soluble forms of these proteins rather than full-length protein can be used, in some embodiments. Soluble forms include, for example, those lacking the transmembrane domain and/or those comprising the IgV domain or fragments thereof which retain their ability to bind their cognate binding partners. Further, agents that inhibit or enhance protein interactions for use in the compositions and methods described herein, can include recombinant peptido-mimetics.

Detection methods useful in screening assays include antibody-based methods, detection of a reporter moiety, detection of cytokines as described herein, and detection of a gene signature as described herein.

Another variation of assays to determine binding of a receptor protein to a ligand protein is through the use of affinity biosensor methods. Such methods may be based on the piezoelectric effect, electrochemistry, or optical methods, such as ellipsometry, optical wave guidance, and surface plasmon resonance (SPR).

Aptamers

Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, cells, tissues and organisms. Nucleic acid aptamers have specific binding affinity to molecules through interactions other than classic Watson-Crick base pairing. Aptamers are useful in biotechnological and therapeutic applications as they offer molecular recognition properties similar to antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. In certain embodiments, RNA aptamers may be expressed from a DNA construct. In other embodiments, a nucleic acid aptamer may be linked to another polynucleotide sequence. The polynucleotide sequence may be a double stranded DNA polynucleotide sequence. The aptamer may be covalently linked to one strand of the polynucleotide sequence. The aptamer may be ligated to the polynucleotide sequence. The polynucleotide sequence may be configured, such that the polynucleotide sequence may be linked to a solid support or ligated to another polynucleotide sequence.

Aptamers, like peptides generated by phage display or monoclonal antibodies ("mAbs"), are capable of specifically binding to selected targets and modulating the target's activity, e.g., through binding, aptamers may block their target's ability to function. A typical aptamer is 10-15 kDa in size (30-45 nucleotides), binds its target with sub-nanomolar affinity, and discriminates against closely related targets (e.g., aptamers will typically not bind other proteins from the same gene family). Structural studies have shown that aptamers are capable of using the same types of binding interactions (e.g., hydrogen bonding, electrostatic complementarity, hydrophobic contacts, steric exclusion) that drives affinity and specificity in antibody-antigen complexes.

Aptamers have a number of desirable characteristics for use in research and as therapeutics and diagnostics including high specificity and affinity, biological efficacy, and excellent pharmacokinetic properties. In addition, they offer specific competitive advantages over antibodies and other protein biologics. Aptamers are chemically synthesized and are readily scaled as needed to meet production demand for research, diagnostic or therapeutic applications. Aptamers are chemically robust. They are intrinsically adapted to regain activity following exposure to factors such as heat and denaturants and can be stored for extended periods (>1 yr) at room temperature as lyophilized powders. Not being bound by a theory, aptamers bound to a solid support or beads may be stored for extended periods.

Oligonucleotides in their phosphodiester form may be quickly degraded by intracellular and extracellular enzymes such as endonucleases and exonucleases. Aptamers can include modified nucleotides conferring improved characteristics on the ligand, such as improved in vivo stability or improved delivery characteristics. Examples of such modifications include chemical substitutions at the ribose and/or phosphate and/or base positions. SILEX identified nucleic acid ligands containing modified nucleotides are described, e.g., in U.S. Pat. No. 5,660,985, which describes oligonucleotides containing nucleotide derivatives chemically modified at the 2' position of ribose, 5 position of pyrimidines, and 8 position of purines, U.S. Pat. No. 5,756,703 which describes oligonucleotide; containing various 2'-modified pyrimidines, and U.S. Pat. No. 5,580,737 which describes highly specific nucleic acid ligands containing one or more nucleotides modified with 2'-amino (2'-$NH_2$), 2'-fluoro (2'-F), and/or 2'-O-methyl (2'-OMe) substituents. Modifications of aptamers may also include, modifications at exocyclic amines, substitution of 4-thiouridine, substitution of 5-bromo or 5-iodo-uracil; backbone modifications, phosphorothioate or allyl phosphate modifications, methylations, and unusual base-pairing combinations such as the isobases isocytidine and isoguanosine. Modifications can also include 3' and 5' modifications such as capping. As used herein, the term phosphorothioate encompasses one or more non-bridging oxygen atoms in a phosphodiester bond replaced by one or more sulfur atoms. In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, S-alkyl, or halo group. Methods of synthesis of 2'-modified sugars are described, e.g., in Sproat, et al., Nucl. Acid Res. 19:733-738 (1991); Cotten, et al, Nucl. Acid Res. 19:2629-2635 (1991); and Hobbs, et al, Biochemistry 12:5138-5145 (1973). Other modifications are known to one of ordinary skill in the art. In certain embodiments, aptamers include aptamers with improved off-rates as described in International Patent Publication No. WO 2009012418, "Method for generating aptamers with improved off-rates," incorporated herein by reference in its entirety. In certain embodiments aptamers are chosen from a library of aptamers. Such libraries include, but are not limited to those described in Rohloff et al., "Nucleic Acid Ligands With Protein-like Side Chains: Modified Aptamers and Their Use as Diagnostic and Therapeutic Agents," Molecular Therapy Nucleic Acids (2014) 3, e201. Aptamers are also commercially available (see, e.g., SomaLogic, Inc., Boulder, Colo.). In certain embodiments, the present invention may utilize any aptamer containing any modification as described herein.

Signature Genes

In certain embodiments, signature genes may be perturbed in single cells and gene expression analyzed. Not being bound by a theory, networks of genes that are disrupted due to perturbation of a signature gene may be determined. Understanding the network of genes effected by a perturbation may allow for a gene to be linked to a specific pathway that may be targeted to modulate the signature and treat a cancer. Thus, in certain embodiments, perturb-seq is used to discover novel drug targets to allow treatment of specific cancer patients having the gene signature of the present invention. Cells or nuclei may be enriched for a target protein after transducing with a perturb-seq library. The target protein may be a signature gene (e.g, a tumor or immune cell signature gene. As used herein a "signature" may encompass any gene or genes, protein or proteins, or epigenetic element(s) whose expression profile or whose occurrence is associated with a specific cell type, subtype, or cell state of a specific cell type or subtype within a population of cells (e.g., immune evading tumor cells, immunotherapy resistant tumor cells, tumor infiltrating lymphocytes, macrophages). In certain embodiments, the expression of the immunotherapy resistant, T cell signature and/or macrophage signature is dependent on epigenetic modification of the genes or regulatory elements associated with the genes. Thus, in certain embodiments, use of signature genes includes epigenetic modifications that may be detected or modulated. For ease of discussion, when discussing gene expression, any of gene or genes, protein or proteins, or epigenetic element(s) may be substituted. As used herein, the terms "signature", "expression profile", or "expression program" may be used interchangeably. It is to be understood that also when referring to proteins (e.g. differentially expressed proteins), such may fall within the definition of "gene" signature. Levels of expression or activity may be compared between different cells in order to characterize or identify for instance signatures specific for cell (sub)populations. Increased or decreased expression or activity or prevalence of signature genes may be compared between different cells in order to characterize or identify for instance specific cell (sub)populations. The detection of a signature in single cells may be used to identify and quantitate for instance specific cell (sub)populations. A signature may include a gene or genes, protein or proteins, or epigenetic element(s) whose expression or occurrence is specific to a cell (sub)population, such that expression or occurrence is exclusive to the cell (sub)population. A gene signature as used herein, may thus refer to any set of up- and/or down-regulated genes that are representative of a cell type or subtype. A gene signature as used herein, may also refer to any set of up- and/or down-regulated genes between different cells or cell (sub)populations derived from a gene-expression profile. For example, a gene signature may comprise a list of genes differentially expressed in a distinction of interest.

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. tumor samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory the signatures of the present invention may be microenvironment specific, such as their expression in a particular spatio-temporal context. Not being bound by a theory, signatures as discussed herein are specific to a particular pathological context. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type. In one embodiment, the novel signatures are used to detect multiple cell states or hierarchies that occur in subpopulations of cells that are linked to particular pathological condition, or linked to a particular outcome or progression of the disease, or linked to a particular response to treatment of the disease (e.g. resistance to immunotherapy).

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular cell or cell (sub)population if it is upregulated or only present, detected or detectable in that particular cell or cell (sub)population, or alternatively is downregulated or only absent, or undetectable in that particular cell or cell (sub)population. In this context, a signature consists of one or more differentially expressed genes/proteins or differential epigenetic elements when comparing different cells or cell (sub)populations, including comparing different immune cells or immune cell (sub)populations (e.g., T cells), as well as comparing immune cells or immune cell (sub)populations with other immune cells or immune cell (sub)populations. It is to be understood that "differentially expressed" genes/proteins include genes/proteins which are up- or down-regulated as well as genes/proteins which are turned on or off. When referring to up-or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of cells. As referred to herein, a "subpopulation" of cells preferably refers to a particular subset of cells of a particular cell type (e.g., resistant) which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively reducing or suppression of a particular signature, preferable is meant induction or alternatively reduction or suppression (or upregulation or downregulation) of at least one gene/protein and/or epigenetic element of the signature, such as for instance at least two, at least three, at least four, at least five, at least six, or all genes/proteins and/or epigenetic elements of the signature.

Various aspects and embodiments of the invention may involve analyzing gene signatures, protein signature, and/or other genetic or epigenetic signature based on single cell analyses (e.g. single cell RNA sequencing) or alternatively based on cell population analyses, as is defined herein elsewhere.

The invention further relates to various uses of the gene signatures, protein signature, and/or other genetic or epigenetic signature as defined herein, as well as various uses of the immune cells or immune cell (sub)populations as defined herein. Particular advantageous uses include methods for identifying agents capable of inducing or suppressing particular immune cell (sub)populations based on the gene signatures, protein signature, and/or other genetic or epigenetic signature as defined herein. The invention further relates to agents capable of inducing or suppressing particular immune cell (sub)populations based on the gene signatures, protein signature, and/or other genetic or epigenetic signature as defined herein, as well as their use for modulating, such as inducing or repressing, a particular gene signature, protein signature, and/or other genetic or epigenetic signature. In one embodiment, genes in one population of cells may be activated or suppressed in order to affect the cells of another population. In related aspects, modulating, such as inducing or repressing, a particular gene signature, protein signature, and/or other genetic or epigenetic signature may modify overall immune composition, such as immune cell composition, such as immune cell subpopulation composition or distribution, or functionality.

The signature genes of the present invention were discovered by analysis of expression profiles of single-cells within a population of tumor cells, thus allowing the discovery of novel cell subtypes that were previously invisible in a population of cells within a tumor. The presence of subtypes may be determined by subtype specific signature genes. The presence of these specific cell types may be determined by applying the signature genes to bulk sequencing data in a patient. Not being bound by a theory, many cells that make up a microenvironment, whereby the cells communicate and affect each other in specific ways. As such, specific cell types within this microenvironment may express signature genes specific for this microenvironment. Not being bound by a theory the signature genes of the present invention may be microenvironment specific, such as their expression in a tumor. The signature genes may indicate the presence of one particular cell type. In one embodiment, the expression may indicate the presence of immunotherapy resistant cell types. Not being bound by a theory, a combination of cell subtypes in a subject may indicate an outcome (e.g., resistant cells, cytotoxic T cells, Tregs).

In certain embodiments, the present invention provides for gene signature screening. The concept of signature screening was introduced by Stegmaier et al. (Gene expression-based high-throughput screening (GE-HTS) and application to leukemia differentiation. Nature Genet. 36, 257-263 (2004)), who realized that if a gene-expression signature was the proxy for a phenotype of interest, it could be used to find small molecules that effect that phenotype without knowledge of a validated drug target. The signature of the present may be used to screen for drugs that reduce the signature in cancer cells or cell lines having a resistant signature as described herein. The signature may be used for GE-HTS. In certain embodiments, pharmacological screens may be used to identify drugs that are selectively toxic to cancer cells having an immunotherapy resistant signature. In certain embodiments, drugs selectively toxic to cancer cells having an immunotherapy resistant signature are used for treatment of a cancer patient. In certain embodiments, cells having an immunotherapy resistant signature as described herein are treated with a plurality of drug candidates not toxic to non-tumor cells and toxicity is assayed.

The Connectivity Map (cmap) is a collection of genome-wide transcriptional expression data from cultured human cells treated with bioactive small molecules and simple pattern-matching algorithms that together enable the discovery of functional connections between drugs, genes and diseases through the transitory feature of common gene-expression changes (see, Lamb et al., The Connectivity Map: Using Gene-Expression Signatures to Connect Small Molecules, Genes, and Disease. Science 29 Sep. 2006: Vol. 313, Issue 5795, pp. 1929-1935, DOI: 10.1126/science.1132939; and Lamb, J., The Connectivity Map: a new tool for biomedical research. Nature Reviews Cancer January 2007: Vol. 7, pp. 54-60). Cmap can be used to screen for a signature in silico.

Perturb-Seq and CITE-Seq

In another aspect, or in alternative embodiments of aspects described herein, the present invention provides for a method wherein proteins or transcripts expressed in single cells are determined in response to a perturbation. Applicants also perform a genome-wide perturb-seq screen combined with CITE-seq-based enrichment to find regulators of a gene signature program. Applicants deliver a barcoded genome-wide library to a cell line, use FACS to bin the population based on expression of a signature gene (e.g., a surface protein), and perform CITE-seq on different binned populations to find positive and negative regulators of the signature. In certain embodiments, a tumor signature is used to bin the cells. In certain embodiments, cancer cell lines are screened. In certain embodiments, signatures associated with resistance or sensitivity to a therapy is screened. In certain embodiments MHCI expression is used to bin the cells as MHCI is a marker from a tumor signature. In certain embodiments, antibodies are used to sort for cells or nuclei expressing a specific marker. In certain embodiments, cells or nuclei are co-stained with CITE-seq antibodies (Stoeckius et al., 2017). In certain embodiments, the CITE-seq antibodies may be labeled with a detectable marker, such that the stained cells can be used to enrich for cells or nuclei of interest and the oligonucleotide tag on the antibodies can be used to capture a cell of origin barcode. In certain embodiments, cells or nuclei that are the highest expressing and lowest expressing are enriched. In certain embodiments, control cells obtained from an unenriched sample are analyzed. In certain embodiments, the top and bottom 20%, 15%, 10%, 5%, 1%, 0.5%, or less than 0.1% are enriched.

Compressed Sensing

Mammalian genomes contain approximately 20,000 genes, and mammalian expression profiles are frequently studied as vectors with 20,000 entries corresponding to the abundance of each gene. It is often assumed that studying gene expression profiles requires measuring and analyzing these 20,000 dimensional vectors, but some mathematical results show that it is often possible to study high-dimensional data in low dimensional space without losing much of the pertinent information. In one embodiment of the present invention, less than 20,000 aptamers are used to detect protein expression in single cells. Not being bound by a theory, working in low dimensional space offers several advantages with respect to computation, data acquisition and fundamental insights about biological systems.

In one embodiment, aptamers are chosen for protein targets that are generally part of gene modules or programs, whereby detection of a protein allows for the ability to infer expression of other proteins present in a module or gene program. Samples are directly compared based only on the measurements of these signature genes.

In alternative embodiments, sparse coding or compressed sensing methods can be used to infer large amounts of data with a limited set of target proteins. Not being bound by a theory, the abundance of each of the 20,000 genes can be recovered from random composite measurements. In this regard, reference is made to Cleary et al., "Composite measurements and molecular compressed sensing for highly efficient transcriptomics" posted on Jan. 2, 2017 at biorxiv.org/content/early/2017/01/02/091926, doi. org/ 10.1101/091926, incorporated herein by reference in its entirety.

Additional Labeling Methods

Methods of international patent publication no. WO2014047561 and US patent publication no. 2015/0259674 are contemplated in the present invention.

The invention also contemplates a labeling ligand which may comprise a unique perturbation identifier (UPI) sequence attached to a perturbation-sequence-capture sequence, and sequencing includes isolating via microbeads comprising a perturbation-sequence-capture-binding-sequence having specific binding affinity for the perturbation-sequence-capture sequence attached to the UPI sequence.

The UPI sequence may be attached to a universal ligation handle sequence, whereby a unique source identifier USI may be generated by split-pool ligation. The labeling ligand may comprise an oligonucleotide label which may comprise a regulatory sequence configured for amplification by T7 polymerase. The labeling ligands may comprise oligonucleotide sequences configured to hybridize to a transcript specific region. The labeling ligand may comprise an oligonucleotide label, wherein the oligonucleotide label may further comprise a photocleavable linker.

The oligonucleotide label may further comprise a restriction enzyme site between the labeling ligand and unique constituent identifier (UCI).

The method may comprise forming discrete unique-identifier-transfer compositions, each of which may comprise the cell and a transfer particle, wherein: (a) an oligonucleotide label further may comprise a capture sequence, and unique constituent identifier (UCI) and capture sequence are together releasably attached to the labeling ligand; the labelling ligand is bound to the target cellular constituent; and, (ca transfer particle may comprise: (i) a capture-binding-sequence having specific binding affinity for the capture sequence attached to the UCI, and, (ii) a unique source identifier (USI) sequence that is unique to each transfer particle.

In one embodiment, the USI may comprise 4-15 nucleotides.

In another embodiment, the invention may further comprise releasing the UCI from the labeled ligand, under conditions within the unique-identifier-transfer composition so that the released capture sequence binds to the capture-binding-sequence on the transfer particle, thereby transferring the UCI to the transfer particle.

In another embodiment, the ligation handle may comprise a restriction site for producing an overhang complementary with a first index sequence overhang, and wherein the method further comprises digestion with a restriction enzyme. In another embodiment, the ligation handle may comprise a nucleotide sequence complementary with a ligation primer sequence and wherein the overhang complementary with a first index sequence overhang is produced by hybridization of the ligation primer to the ligation handle.

In another embodiment, the invention may further comprise quantitating relative amount of UCI sequence associated with a first cell to the amount of the same UCI sequence associated with a second cell, whereby the relative differences of a cellular constituent between cell(s) are determined.

In another embodiment, the labeling ligand may comprise an antibody or an antibody fragment, such as but not limited to, a nanobody, Fab, Fab', (Fab')2, Fv, ScFv, diabody, triabody, tetrabody, Bis-scFv, minibody, Fab2, or Fab3 fragment.

In another embodiment, the labeling ligand may comprise an aptamer.

In another embodiment, the labeling ligand may comprise a nucleotide sequence complementary to a target sequence.

In another embodiment, the cell or a population includes wherein the cell(s) are a member of a cell population, and the method further comprises transforming or transducing the cell population with one or more genomic sequence-perturbation constructs that perturb a genomic sequence in the cells, wherein each distinct genomic sequence-perturbation construct comprises a unique-perturbation-identified (UPI) sequence unique to that construct. The genomic sequence-perturbation construct may comprises sequence encoding a guide RNA sequence of a CRISPR-Cas targeting system. The method may further comprise multiplex transformation of the population of cells with a plurality of genomic sequence-perturbation constructs. The method may further comprise a UPI sequence attached to a perturbation-sequence-capture sequence, and the transfer particle may comprise a perturbation-sequence-capture-binding-sequence having specific binding affinity for the perturbation-sequence-capture sequence attached to the UPI sequence. The UPI sequence is attached to a universal ligation handle sequence, whereby a USI is generated by split-pool ligation.

In an advantageous embodiment, agents may be uniquely labeled in a dynamic manner (see, e.g., US provisional patent application Ser. No. 61/703,884 filed Sep. 21, 2012). The unique labels are, at least in part, nucleic acid in nature, and may be generated by sequentially attaching two or more detectable oligonucleotide tags to each other and each unique label may be associated with a separate agent. A detectable oligonucleotide tag may be an oligonucleotide that may be detected by sequencing of its nucleotide sequence and/or by detecting non-nucleic acid detectable moieties to which it may be attached.

The oligonucleotide tags may be detectable by virtue of their nucleotide sequence, or by virtue of a non-nucleic acid detectable moiety that is attached to the oligonucleotide such as but not limited to a fluorophore, or by virtue of a combination of their nucleotide sequence and the nonnucleic acid detectable moiety.

In some embodiments, a detectable oligonucleotide tag may comprise one or more nonoligonucleotide detectable moieties. Examples of detectable moieties may include, but are not limited to, fluorophores, microparticles including quantum dots (Empodocles, et al., Nature 399:126-130, 1999), gold nanoparticles (Reichert et al., Anal. Chem. 72:6025-6029, 2000), microbeads (Lacoste et al., Proc. Natl. Acad. Sci. USA 97(17):9461-9466, 2000), biotin, DNP (dinitrophenyl), fucose, digoxigenin, haptens, and other detectable moieties known to those skilled in the art. In some embodiments, the detectable moieties may be quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique label may be produced by sequentially attaching two or more detectable oligonucleotide tags to each other. The detectable tags may be present or provided in a plurality of detectable tags. The same or a different plurality of tags may be used as the source of each detectable tag may be part of a unique label. In other words, a plurality of tags may be subdivided into subsets and single subsets may be used as the source for each tag.

In some embodiments, one or more other species may be associated with the tags. In particular, nucleic acids released by a lysed cell may be ligated to one or more tags. These may include, for example, chromosomal DNA, RNA transcripts, tRNA, mRNA, mitochondrial DNA, or the like. Such nucleic acids may be sequenced, in addition to sequencing the tags themselves, which may yield information about the nucleic acid profile of the cells, which can be associated with the tags, or the conditions that the corresponding droplet or cell was exposed to.

For a convenient detection of the probe-target complexes formed during the hybridization assay, the nucleotide probes are conjugated to a detectable label. Detectable labels suitable for use in the present invention include any composition detectable by photochemical, biochemical, spectroscopic, immunochemical, electrical, optical or chemical means. A wide variety of appropriate detectable labels are known in the art, which include fluorescent or chemiluminescent labels, radioactive isotope labels, enzymatic or other ligands. In preferred embodiments, one will likely desire to employ a fluorescent label or an enzyme tag, such as digoxigenin, ß-galactosidase, urease, alkaline phosphatase or peroxidase, avidin/biotin complex.

The detection methods used to detect or quantify the hybridization intensity will typically depend upon the label selected above. For example, radiolabels may be detected using photographic film or a phosphoimager. Fluorescent markers may be detected and quantified using a photodetector to detect emitted light. Enzymatic labels are typically detected by providing the enzyme with a substrate and measuring the reaction product produced by the action of the enzyme on the substrate; and finally colorimetric labels are detected by simply visualizing the colored label.

Examples of the labeling substance which may be employed include labeling substances known to those skilled in the art, such as fluorescent dyes, enzymes, coenzymes, chemiluminescent substances, and radioactive substances. Specific examples include radioisotopes (e.g., $^{32}$P, $^{14}$C, $^{125}$I, $^{3}$H, and $^{131}$I) fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

Advantageously, the label is a fluorescent label. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAN/IRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine The fluorescent label may be a fluorescent protein, such as blue fluorescent protein, cyan fluorescent protein, green fluorescent protein, red fluorescent protein, yellow fluorescent protein or any photoconvertible protein. Colormetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terrylen. In the alternative, the fluorescent label may be a fluorescent bar code.

In an advantageous embodiment, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation.

In an advantageous embodiment, agents may be uniquely labeled in a dynamic manner (see, e.g., international patent application serial no. PCT/US2013/61182 filed Sep. 23, 2012). The unique labels are, at least in part, nucleic acid in nature, and may be generated by sequentially attaching two or more detectable oligonucleotide tags to each other and each unique label may be associated with a separate agent. A detectable oligonucleotide tag may be an oligonucleotide that may be detected by sequencing of its nucleotide sequence and/or by detecting non-nucleic acid detectable moieties to which it may be attached.

The oligonucleotide tags may be detectable by virtue of their nucleotide sequence, or by virtue of a non-nucleic acid detectable moiety that is attached to the oligonucleotide such as but not limited to a fluorophore, or by virtue of a combination of their nucleotide sequence and the nonnucleic acid detectable moiety.

In some embodiments, a detectable oligonucleotide tag may comprise one or more nonoligonucleotide detectable moieties. Examples of detectable moieties may include, but are not limited to, fluorophores, microparticles including quantum dots (Empodocles, et al., Nature 399:126-130, 1999), gold nanoparticles (Reichert et al., Anal. Chem. 72:6025-6029, 2000), biotin, DNP (dinitrophenyl), fucose, digoxigenin, haptens, and other detectable moieties known to those skilled in the art. In some embodiments, the detectable moieties may be quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique label may be produced by sequentially attaching two or more detectable oligonucleotide tags to each other. The detectable tags may be present or provided in a plurality of detectable tags. The same or a different plurality of tags may be used as the source of each detectable tag may be part of a unique label. In other words, a plurality of tags may be subdivided into subsets and single subsets may be used as the source for each tag.

In some embodiments, a detectable oligonucleotide tag may comprise one or more non-oligonucleotide detectable moieties. Examples of detectable moieties include, but are not limited to, fluorophores, microparticles including quantum dots (Empodocles, et al., Nature 399:126-130, 1999), gold nanoparticles (Reichert et al., Anal. Chem. 72:6025-6029, 2000), biotin, DNP (dinitrophenyl), fucose, digoxigenin, haptens, and other detectable moieties known to those skilled in the art. In some embodiments, the detectable moieties are quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique nucleotide sequence may be a nucleotide sequence that is different (and thus distinguishable) from the sequence of each detectable oligonucleotide tag in a plurality of detectable oligonucleotide tags. A unique nucleotide sequence may also be a nucleotide sequence that is different (and thus distinguishable) from the sequence of each detectable oligonucleotide tag in a first plurality of detectable oligonucleotide tags but identical to the sequence of at least one detectable oligonucleotide tag in a second plurality of detectable oligonucleotide tags. A unique sequence may differ from other sequences by multiple bases (or base pairs). The multiple bases may be contiguous or non-contiguous. Methods for obtaining nucleotide sequences (e.g., sequencing methods) are described herein and/or are known in the art.

In some embodiments, detectable oligonucleotide tags comprise one or more of a ligation sequence, a priming sequence, a capture sequence, and a unique sequence (optionally referred to herein as an index sequence). A ligation sequence is a sequence complementary to a second nucleotide sequence which allows for ligation of the detectable oligonucleotide tag to another entity which may comprise the second nucleotide sequence, e.g., another detectable oligonucleotide tag or an oligonucleotide adapter. A priming sequence is a sequence complementary to a primer, e.g., an oligonucleotide primer used for an amplification reaction such as but not limited to PCR. A capture sequence is a sequence capable of being bound by a capture entity. A capture entity may be an oligonucleotide which may comprise a nucleotide sequence complementary to a capture sequence, e.g. a second detectable oligonucleotide tag. A capture entity may also be any other entity capable of binding to the capture sequence, e.g. an antibody, hapten or peptide. An index sequence is a sequence which may comprise a unique nucleotide sequence and/or a detectable moiety as described above.

Computing Systems

The present invention also relates to a computer system involved in carrying out the methods of the invention relating to both computations and sequencing.

A computer system (or digital device) may be used to receive, transmit, display and/or store results, analyze the results, and/or produce a report of the results and analysis. A computer system may be understood as a logical apparatus that can read instructions from media (e.g. software) and/or network port (e.g. from the internet), which can optionally be connected to a server having fixed media. A computer system may comprise one or more of a CPU, disk drives, input devices such as keyboard and/or mouse, and a display (e.g. a monitor). Data communication, such as transmission of instructions or reports, can be achieved through a communication medium to a server at a local or a remote location. The communication medium can include any means of transmitting and/or receiving data. For example, the communication medium can be a network connection, a wireless connection, or an internet connection. Such a connection can provide for communication over the World Wide Web. It is envisioned that data relating to the present invention can be transmitted over such networks or connections (or any other suitable means for transmitting information, including but not limited to mailing a physical report, such as a print-out) for reception and/or for review by a receiver. The receiver can be but is not limited to an individual, or electronic system (e.g. one or more computers, and/or one or more servers).

In some embodiments, the computer system may comprise one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other suitable storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

A client-server, relational database architecture can be used in embodiments of the invention. A client-server architecture is a network architecture in which each computer or process on the network is either a client or a server. Server computers are typically powerful computers dedicated to managing disk drives (file servers), printers (print servers), or network traffic (network servers). Client computers include PCs (personal computers) or workstations on which users run applications, as well as example output devices as disclosed herein. Client computers rely on server computers for resources, such as files, devices, and even processing power. In some embodiments of the invention, the server computer handles all of the database functionality. The client computer can have software that handles all the front-end data management and can also receive data input from users.

A machine readable medium which may comprise computer-executable code may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The subject computer-executable code can be executed on any suitable device which may comprise a processor, including a server, a PC, or a mobile device such as a smartphone or tablet. Any controller or computer optionally includes a monitor, which can be a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard, mouse, or touch-sensitive screen, optionally provide for input from a user. The computer can include appropriate software for receiving user instructions, either in the form of user input into a set of parameter fields, e.g., in a GUI, or in the form of preprogrammed instructions, e.g., preprogrammed for a variety of different specific operations.

Screening Methods

The present invention also envisions screening methods involving the herein described embodiments.

In one embodiment, the screening involves a pooled, loss-of-function genetic screening approach suitable for both positive and negative selection that uses a genome-scale lentiviral single-guide RNA (sgRNA) library (see, e.g., Wang et al., Science. 2014 Jan. 3; 343(6166):80-4. doi: 10.1126/science.1246981. Epub 2013 Dec. 12). Briefly, sgRNA expression cassettes were stably integrated into the genome, which enabled a complex mutant pool to be tracked by massively parallel sequencing. A library containing 73,000 sgRNAs was used to generate knockout collections and performed screens in two human cell lines. A screen for resistance to the nucleotide analog 6-thioguanine identified all expected members of the DNA mismatch repair pathway, whereas another for the DNA topoisomerase II (TOP2A) poison etoposide identified TOP2A, as expected, and also cyclin-dependent kinase 6, CDK6. A negative selection screen for essential genes identified numerous gene sets corresponding to fundamental processes. sgRNA efficiency is associated with specific sequence motifs, enabling the prediction of more effective sgRNAs. See also Chen et al., Genome-wide CRISPR Screen in a Mouse Model of Tumor Growth and Metastasis, Cell (2015). DOI: 10.1016/j.cell.2015.02.038.

The activator screen method of Konermann et al., Nature (2014) doi:10.1038/nature14136 may be applied to the present invention. Systematic interrogation of gene function requires the ability to perturb gene expression in a robust and generalizable manner. Konermann et al. describes structure-guided engineering of a CRISPR-Cas9 complex to mediate efficient transcriptional activation at endogenous genomic loci. Konermann et al. used these engineered Cas9 activation complexes to investigate single-guide RNA (sgRNA) targeting rules for effective transcriptional activation, to demonstrate multiplexed activation of ten genes simultaneously, and to upregulate long intergenic non-coding RNA (lincRNA) transcripts. Konermann et al. also synthesized a library consisting of 70,290 guides targeting all human RefSeq coding isoforms to screen for genes that, upon activation, confer resistance to a BRAF inhibitor. The top hits included genes previously shown to be able to confer resistance, and novel candidates were validated using individual sgRNA and complementary DNA overexpression. A gene signature based on the top screening hits correlated with a gene expression signature of BRAF inhibitor resistance in cell lines and patient-derived samples. These results collectively demonstrate the potential of Cas9-based activators as a powerful genetic perturbation technology.

The mouse of Platt et al., Cell. 2014 Oct. 9;159(2):440-55. doi: 10.1016/j.cell.2014.09.014. Epub 2014 Sep. 25 may also be contemplated in the present invention. Platt et al. established a Cre-dependent Cas9 knockin mouse and demonstrated in vivo as well as ex vivo genome editing using adeno-associated virus (AAV)-, lentivirus-, or particle-mediated delivery of guide RNA in neurons, immune cells, and endothelial cells. Using these mice, Platt et al. simultaneously modeled the dynamics of KRAS, p53, and LKB1, the top three significantly mutated genes in lung adenocarcinoma. Delivery of a single AAV vector in the lung generated loss-of-function mutations in p53 and Lkb 1, as well as homology-directed repair-mediated Kras(G12D) mutations, leading to macroscopic tumors of adenocarcinoma pathology. In certain embodiments, Cre-dependent Cas9 knockin mice or any Cre-dependent CRISPR enzyme mouse (e.g., Cpf1) may be crossed with tissue-specific Cre transgenic mice as described herein.

The present invention may be further illustrated and extended based on aspects of CRISPR-Cas development and use as set forth in the following articles and particularly as relates to delivery of a CRISPR protein complex and uses of an RNA guided endonuclease in cells and organisms:

Multiplex genome engineering using CRISPR-Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121): 819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR-Cas-Mediated Genome Engineering. Wang H., Yang H., Shivalila C S., Dawlaty M M., Cheng A W., Zhang F., Jaenisch R. Cell May 9; 153(4):910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463):472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, FA., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science Dec. 12, 2013;

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR-Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520 (7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR-Cas9 cleavage of viral DNA efficiently suppresses hepatitis B virus," Scientific Reports 5:10833. doi: 10.1038/srep10833 (Jun. 2, 2015)

Nishimasu et al., Crystal Structure of *Staphylococcus aureus* Cas9," Cell 162, 1113-1126 (Aug. 27, 2015)

BCL11A enhancer dissection by Cas9-mediated in situ saturating mutagenesis, Canver et al., Nature 527 (7577):192-7 (Nov. 12, 2015) doi: 10.1038/nature15521. Epub 2015 Sep. 16.

*Cpf1 Is a Single RNA-Guided Endonuclease of a Class* 2 *CRISPR-Cas System*, Zetsche et al., Cell 163, 759-71 (Sep. 25, 2015).

*Discovery and Functional Characterization of Diverse Class* 2 *CRISPR-Cas Systems*, Shmakov et al., Molecular Cell, 60(3), 385-397 doi: 10.1016/j.molcel.2015.10.008 Epub Oct. 22, 2015.

Rationally engineered Cas9 nucleases with improved specificity, Slaymaker et al., Science 2016 Jan. 1 351 (6268): 84-88 doi: 10.1126/science.aad5227. Epub 2015 Dec. 1.

Gao et al, "Engineered Cpf1 Enzymes with Altered PAM Specificities," bioRxiv 091611; doi: http://dx.doi.org/10.1101/091611 (Dec. 4, 2016).

Cox et al., "RNA editing with CRISPR-Cas13," Science. 2017 Nov. 24; 358(6366):1019-1027. doi: 10.1126/science.aaq0180. Epub 2017 Oct. 25.

Gaudelli et al. "Programmable base editing of A-T to G-C in genomic DNA without DNA cleavage" Nature 464 (551); 464-471 (2017).

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA: Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and guide RNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knock-out (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR-Cas9 knockout and nucleotide preference at the cleavage site. The authors also found that the sequence preference for CRISPRi/a is substantially different from that for CRISPR-Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2016) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

Cox et al., (2017) reported the use of catalytically inactive Cas13 (dCas13) to direct adenosine-to-inosine deaminase activity by ADAR2 (adenosine deaminase acting on RNA type 2) to transcripts in mammalian cells. The system, referred to as RNA Editing for Programmable A to I Replacement (REPAIR), has no strict sequence constraints and can be used to edit full-length transcripts. The authors further engineered the system to create a high-specificity variant and minimized the system to facilitate viral delivery.

The methods and tools provided herein are may be designed for use with or Cas13, a type II nuclease that does not make use of tracrRNA. Orthologs of Cas13 have been identified in different bacterial species as described herein. Further type II nucleases with similar properties can be identified using methods described in the art (Shmakov et al. 2015, 60:385-397; Abudayeh et al. 2016, Science, 5;353 (6299)). In particular embodiments, such methods for identifying novel CRISPR effector proteins may comprise the steps of selecting sequences from the database encoding a seed which identifies the presence of a CRISPR Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided Fold Nucleases that recognize extended sequences and can edit endogenous genes with high efficiencies in human cells.

With respect to general information on CRISPR/Cas Systems, components thereof, and delivery of such components, including methods, materials, delivery vehicles, vectors, particles, and making and using thereof, including as to amounts and formulations, as well as CRISPR-Cas-expressing eukaryotic cells, CRISPR-Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, and 8,945,839; US Patent Publications US 2014-0310830 (U.S. application Ser. No. 14/105, 031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256, 912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); U.S. Ser. No. 14/054,414 European Patent Applications EP 2 771 468 (EP13818570.7), EP 2 764 103 (EP13824232.6), and EP 2 784 162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/074691), WO2014/093655 (PCT/US2013/074736), WO2014/093712 (PCT/US2013/074819), WO2014/093701 (PCT/US2013/074800), WO2014/018423 (PCT/US2013/051418), WO2014/204723 (PCT/US2014/041790), WO2014/204724 (PCT/US2014/041800), WO2014/204725 (PCT/US2014/041803), WO2014/204726 (PCT/US2014/041804), WO2014/204727 (PCT/US2014/041806), WO2014/204728 (PCT/US2014/041808), WO2014/204729 (PCT/US2014/041809), WO2015/089351 (PCT/US2014/069897), WO2015/089354 (PCT/US2014/069902), WO2015/089364 (PCT/US2014/069925), WO2015/089427 (PCT/US2014/070068), WO2015/089462 (PCT/US2014/070127), WO2015/089419 (PCT/US2014/070057), WO2015/089465 (PCT/US2014/070135), WO2015/089486 (PCT/US2014/070175), WO2015/058052 (PCT/US2014/061077), WO2015/070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO2016/049258 (PCT/US2015/051830), WO2016/094867 (PCT/US2015/065385), WO2016/094872 (PCT/US2015/065393), WO2016/094874 (PCT/US2015/065396), WO2016/106244 (PCT/US2015/067177).

Mention is also made of US application 62/180,709, 17 Jun. 2015, PROTECTED GUIDE RNAS (PGRNAS); US application 62/091,455, filed, 12 Dec. 2014, PROTECTED GUIDE RNAS (PGRNAS); US application 62/096,708, 24 Dec. 2014, PROTECTED GUIDE RNAS (PGRNAS); US applications 62/091,462, 12 Dec. 2014, 62/096,324, 23 Dec. 2014, 62/180,681, 17 Jun. 2015, and 62/237,496, 5 Oct. 2015, DEAD GUIDES FOR CRISPR TRANSCRIPTION FACTORS; US application 62/091,456, 12 Dec. 2014 and 62/180,692, 17 Jun. 2015, ESCORTED AND FUNCTIONALIZED GUIDES FOR CRISPR-CAS SYSTEMS; US application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOETIC STEM CELLS (HSCs); US application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; US application 62/096,761, 24 Dec. 2014, ENGINEERING OF SYSTEMS, METHODS AND OPTIMIZED ENZYME AND GUIDE SCAFFOLDS FOR SEQUENCE MANIPULATION; US application 62/098,059, 30 Dec. 2014, 62/181,641, 18 Jun. 2015, and 62/181,667, 18 Jun. 2015, RNA-TARGETING SYSTEM; US application 62/096,656, 24 Dec. 2014 and 62/181,151, 17 Jun. 2015, CRISPR HAVING OR ASSOCIATED WITH DESTABILIZATION DOMAINS; US application 62/096,697, 24 Dec. 2014, CRISPR HAVING OR ASSOCIATED WITH AAV; US application 62/098,158, 30 Dec. 2014, ENGINEERED CRISPR COMPLEX INSERTIONAL TARGETING SYSTEMS; US application 62/151,052, 22 Apr. 2015, CELLULAR TARGETING FOR EXTRACELLULAR EXOSOMAL REPORTING; US application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; US application 61/939,154, 12 Feb. 2014, SYSTEMS, METHODS AND COMPOSITIONS FOR SEQUENCE MANIPULATION WITH OPTIMIZED FUNCTIONAL CRISPR-CAS SYSTEMS; US application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; US application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; US application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; US application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; US applications 62/054,675, 24 Sep. 2014 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; US application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; US application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); US application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; US application 62/087,475, 4 Dec. 2014 and 62/181,690, 18 Jun. 2015, FUNCTIONAL SCREENING WITH OPTIMIZED FUNCTIONAL CRISPR-CAS SYSTEMS; US application 62/055,487, 25 Sep. 2014, FUNCTIONAL SCREENING WITH OPTIMIZED FUNCTIONAL CRISPR-CAS SYSTEMS; US application 62/087,546, 4 Dec. 2014 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and US application 62/098,285, 30 Dec. 2014, CRISPR MEDIATED IN VIVO MODELING AND GENETIC SCREENING OF TUMOR GROWTH AND METASTASIS.

Mention is made of US applications 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of US applications 62/181,663, 18 Jun. 2015 and 62/245,264, 22 Oct. 2015, NOVEL CRISPR ENZYMES AND SYSTEMS, US applications 62/181,675, 18 Jun. 2015, 62/285,349, 22 Oct. 2015, 62/296,522, 17 Feb. 2016, and 62/320,231, 8 Apr. 2016, NOVEL CRISPR ENZYMES AND SYSTEMS, US application 62/232,067, 24 Sep. 2015, U.S. application Ser. No. 14/975,085, 18 Dec. 2015, European application No. 16150428.7, US application 62/205,733, 16 Aug. 2015, US application 62/201,542, 5 Aug. 2015, US application 62/193,507, 16 Jul. 2015, and US application 62/181,739, 18 Jun. 2015, each entitled NOVEL CRISPR ENZYMES AND SYSTEMS and of US application 62/245,270, 22 Oct. 2015, NOVEL CRISPR ENZYMES AND SYSTEMS. Mention is also made of US application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, US application 62/180,699, 17 Jun. 2015, and US application 62/038,358, 17 Aug. 2014, each entitled GENOME EDITING USING CAS9 NICKASES.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

In particular embodiments, pre-complexed guide RNA and CRISPR effector protein, (optionally, adenosine deaminase fused to a CRISPR protein or an adaptor) are delivered as a ribonucleoprotein (RNP). RNPs have the advantage that they lead to rapid editing effects even more so than the RNA method because this process avoids the need for transcription. An important advantage is that both RNP delivery is transient, reducing off-target effects and toxicity issues. Efficient genome editing in different cell types has been observed by Kim et al. (2014, Genome Res. 24(6):1012-9), Paix et al. (2015, Genetics 204(1):47-54), Chu et al. (2016, BMC Biotechnol. 16:4), and Wang et al. (2013, Cell. 9;153 (4):910-8).

In particular embodiments, the ribonucleoprotein is delivered by way of a polypeptide-based shuttle agent as described in WO2016161516. WO2016161516 describes efficient transduction of polypeptide cargos using synthetic peptides comprising an endosome leakage domain (ELD) operably linked to a cell penetrating domain (CPD), to a histidine-rich domain and a CPD. Similarly these polypeptides can be used for the delivery of CRISPR-effector based RNPs in eukaryotic cells.

The invention is further described in the following examples, which do not limit the scope of the invention described in the claims.

EXAMPLES

Example 1

Nuclei Multiplexing with Barcoded Antibodies for Single-Nucleus Genomics

Single-nucleus RNA-seq (snRNA-Seq) has become an instrumental method for interrogating cell types, states, and function in complex tissues that cannot be dissociated (N. Habib et al., Massively parallel single-nucleus RNA-seq with DroNc-seq. Nat Methods 14, 955-958 (2017); and C. Nagy et al., Single-nucleus RNA sequencing shows convergent evidence from different cell types for altered synaptic plasticity in major depressive disorder. BioRxiv, (2018)). This includes tissues rich in cell types such as neurons, adipocytes and skeletal muscle cells, archived frozen clinical materials, and tissues that must be frozen to register into specific coordinates. In principle, the ability to handle minute frozen specimens (N. Habib et al., Div-Seq: Single-nucleus RNA-Seq reveals dynamics of rare adult newborn neurons. Science 353, 925-928 (2016)), has made snRNA-seq a compelling option for large scale studies from tissue atlases (S. M. Sunkin et al., Allen Brain Atlas: an integrated spatio-temporal portal for exploring the central nervous system. Nucleic Acids Res 41, D996-D1008 (2013); and Regev, et al., Human Cell Atlas Organizing Committee, The Human Cell Atlas White Paper. arXiv 1810.05192, (2018)), to longitudinal clinical trials, to human genetics. However, to maximize the success of such studies there is a crucial need to minimize batch effects, reduce costs, and streamline the preparation of large numbers of samples.

For single cell analysis, these goals have recently been elegantly achieved by multiplexing samples prior to cellular processing, which are barcoded either through natural genetic variation (H. M. Kang et al., Multiplexed droplet single-cell RNA-sequencing using natural genetic variation. Nat Biotechnol 36, 89-94 (2018)), chemical labeling (J. Gehring, J. H. Park, S. Chen, M. Thomson, L. Pachter, Highly Multiplexed Single-Cell RNA-seq for Defining Cell Population and Transcriptional Spaces. BioRxiv, (2018)) or DNA-tagged antibodies (M. Stoeckius et al., Cell "hashing" with barcoded antibodies enables multiplexing and doublet detection for single cell genomics. BioRxiv, (2018)) ("cell-hashing"). These methods have improved technical inter-sample variability by early pooling, lower the cost per sample by overloading cells per microfluidic run—due to an increased ability to detect and discard co-encapsulated "cell multiplets" sharing the same bead barcode—and reduce the number of parallel processing steps in large studies.

Here, Applicants follow on these studies by developing a sample multiplexing method for nuclei ("nucleus hashing"), using DNA-barcoded antibodies targeting the nuclear pore complex. Unlike methods leveraging natural genetic variation (Kang et al., 2018), barcoded antibodies allow pooling of isogenic samples, such as from isogenic mouse models, multiple specimens from the same human donor, or tissues sampled and preserved from a given donor over time.

Figure 2:
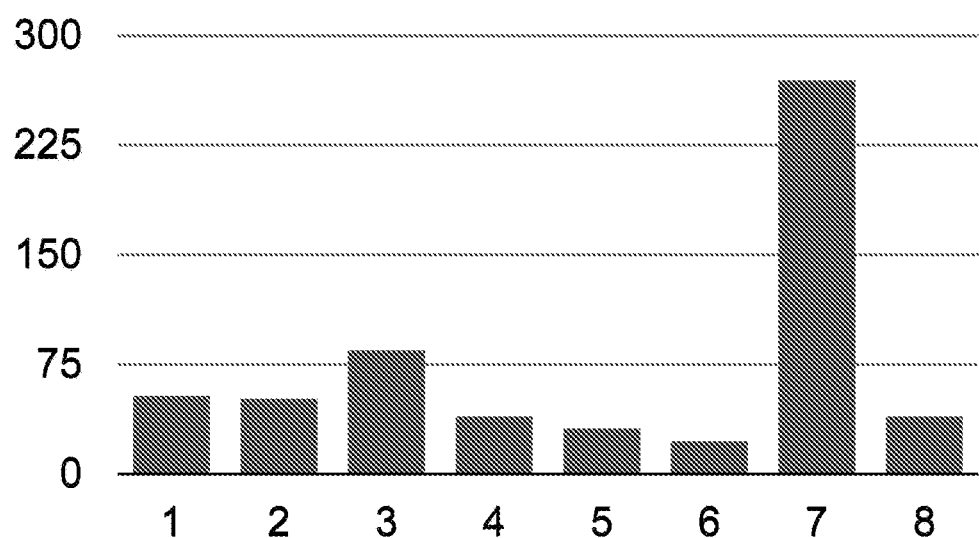
FIG. 2—illustrates a bar graph illustrating singlets and doublets in single cell sequencing.
Figure 4:
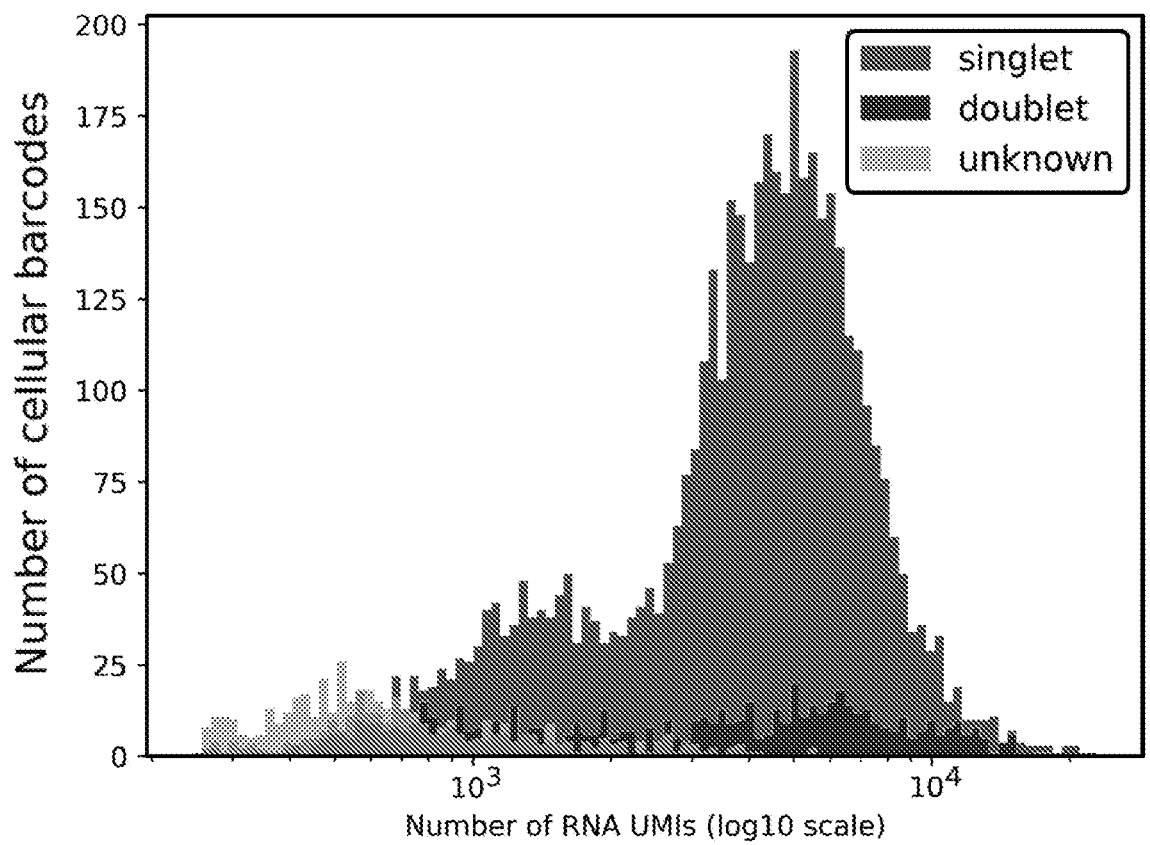
FIG. 4—illustrates the demuxEM computational criteria for calling singlets, doublets and unknown. The histogram shows the number of RNA UMIs colored by singlet, doublet, and unknown.

Single-nucleus RNA-Seq is important for developing a cell atlas, especially for the brain because of the difficulty in dissociating brain tissues. Applicants developed nuclei-hashing, a novel nuclei pooling protocol that can reduce batch effects, reduce experimental cost, and enable pooling of isogenic samples (FIG. 1). The nuclei hashing protocol reduces batch effects, reduces cost per nucleus by overloading, and allows for combining isogenic samples (e.g., mouse models, different tissues from the same donor). In this protocol, Applicants isolate nuclei from frozen tissues, stain them with sample-barcoded anti-nuclear pore complex antibodies, pool samples and sequence them using 10× platform, and finally demultiplex nuclei computationally. Demultiplexing singlets and multilets The program uses the single sequencing data with sample barcodes to demultiplex singlets from doublets, triplets etc. The following is a description of the data input. Suppose there are n samples pooled together, each sample having a sample barcode. Ideally, one hashtag count vector is obtained, $(c_1, \ldots, c_n)$, per cellular barcode. The output provides for singlets and doublets (FIG. 2). There is a need to infer if a droplet is a singlet or doublet and if it is a singlet, determine which sample was the origin. Applicants provide a computational method to overcome background noise. FIG. 3 illustrates demuxEM, which is an algorithm that provides a solution for demultiplexing singlets and multiplets. To handle background noise, Applicants developed demuxEM to estimate Theta from hashtag count vectors. Theta_0 is the fraction of hashtags from background. Theta_1 to Theta_n are the fractions of hashtags from each sample. FIG. 4 illustrates the demultiplexing criteria. If there is over 80% of hashtags from background, there is not enough data to demultiplex and assigned as unknown. Otherwise, Applicants count the number of samples with at least 10% hashtags among non-background hashtags. If this number is 1, it is a singlet. Otherwise, it is a doublet. FIG. 4 shows a histogram on the number of RNA UMIs colored by singlet, doublet, and unknown. The unknown group has less UMIs, which suggest low quality.

Figure 5:
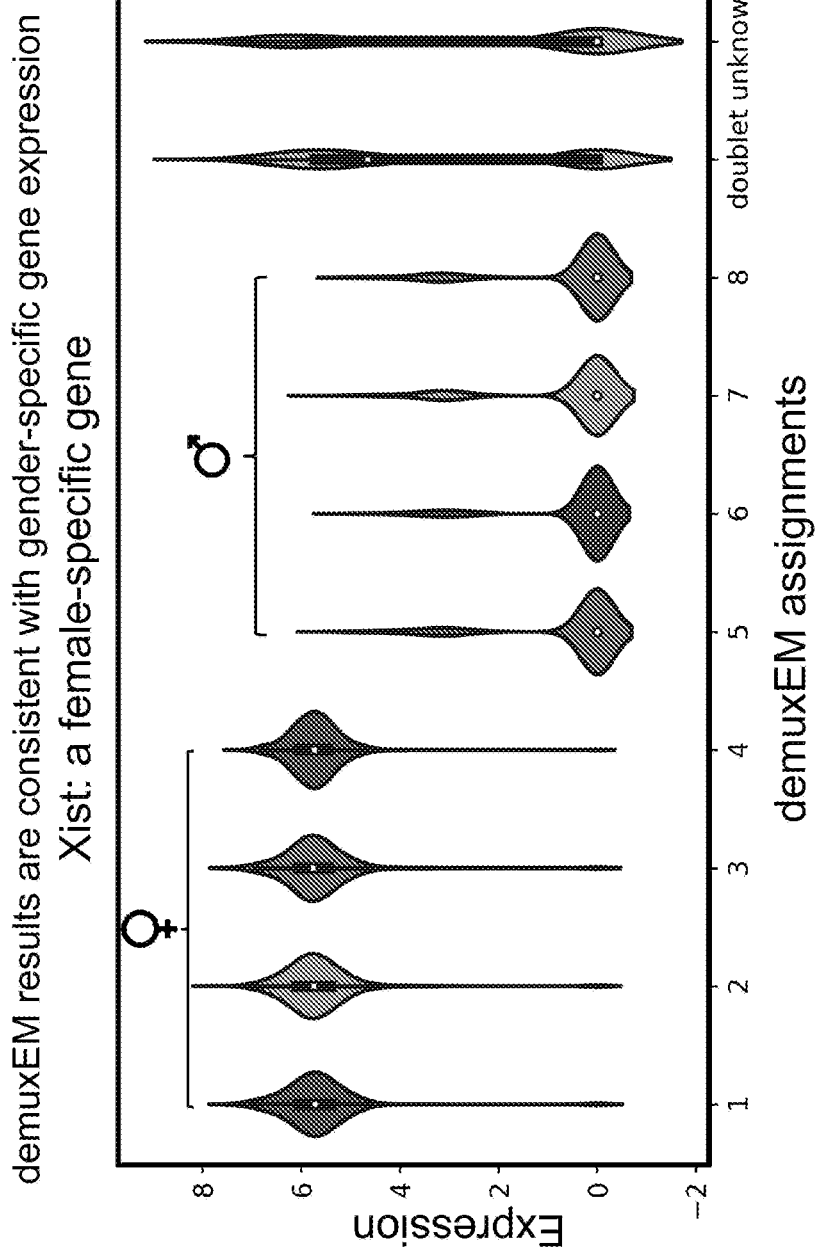
FIG. 5—illustrates validation of demuxEM results using gender-specific gene expression.
Figure 9:
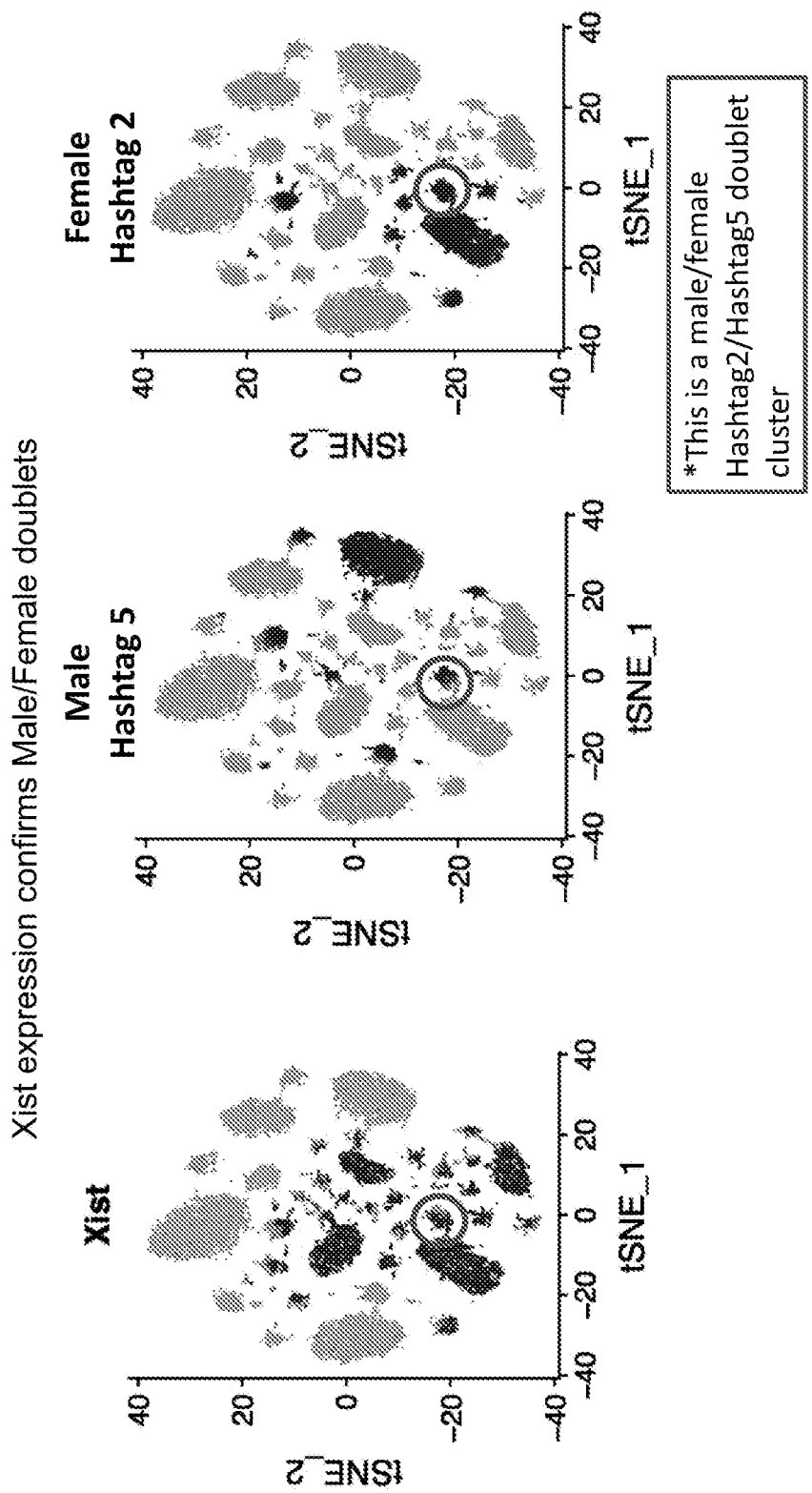
FIG. 9—illustrates tSNE plots of Xist using hashtag expression in male and female mice.

FIG. 5 illustrates validation of the demuxEM results with gender-specific gene expression. In this experiment, Applicants pooled 8 mouse cortex nuclei samples. The first 4 are technical replicates from a female mouse, and the last 4 are technical replicates from a male mouse. The expression of Xist, which is specifically expressed in females, is used to show that demuxEM results successfully distinguish females from males. FIG. 9 is an experiment showing that Xist expression confirms Male/Female doublets.

Figure 6:
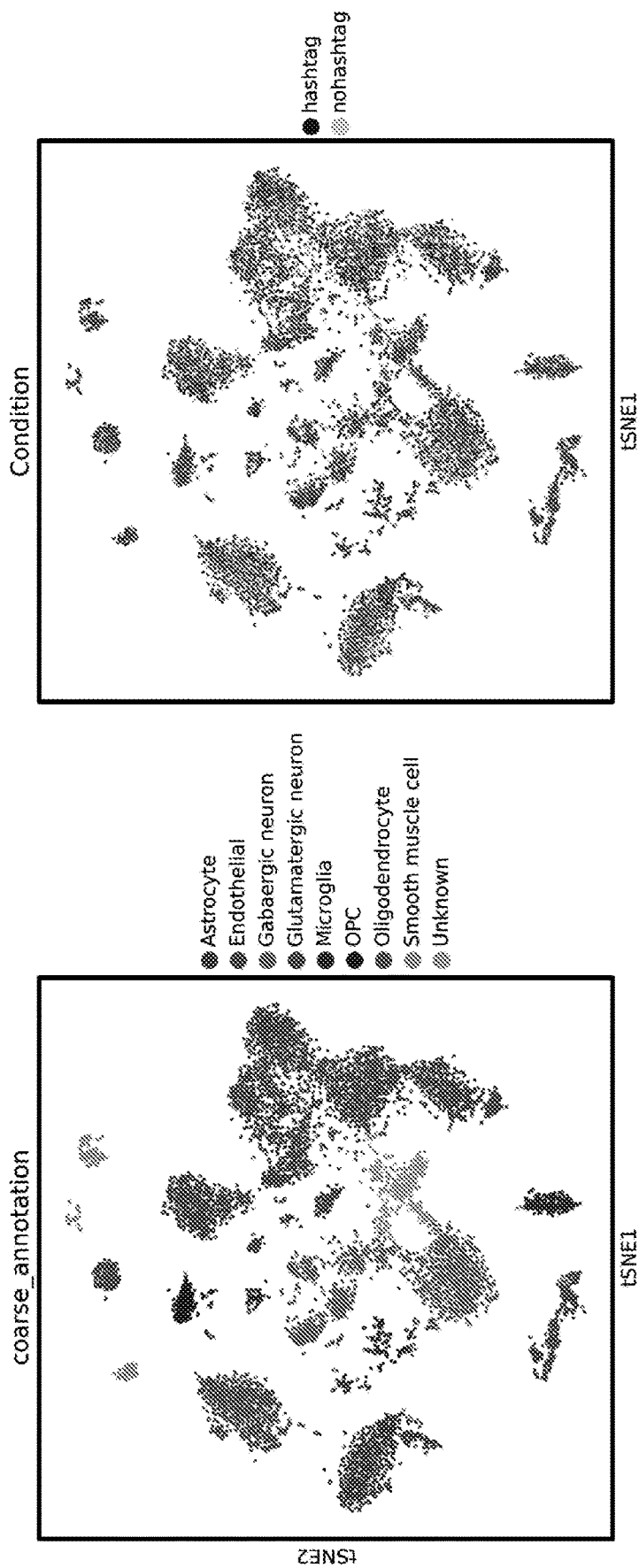
FIG. 6—illustrates tSNE plots showing clustering of single cells from the brain by cell type and by hashtag (sample barcode).

FIG. 6 illustrates that nuclei-hashing does not change cell type distribution. Applicants generated a control of eight pooled samples without the staining step and at the same time produced the nuclei-hashing data. Applicants analyzed these two data together. The left panel shows identified cell types. The right panel is colored by nuclei-hashing and control. The hashing data and control data are clustered together within each cell type.

Figure 7:
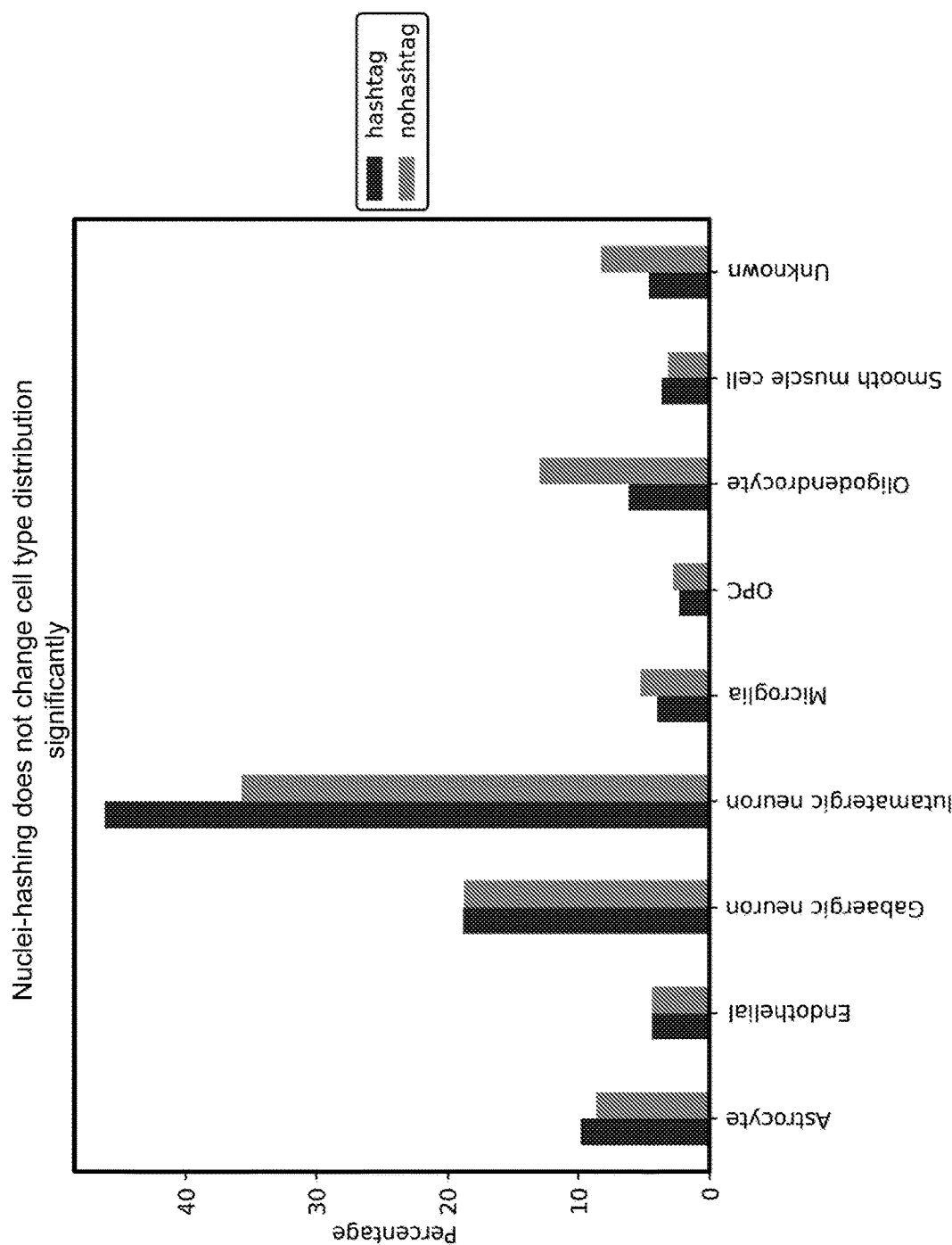
FIG. 7—illustrates a bar plot of the percentages of nuclei that belong to every cell type for each condition.
Figure 8:
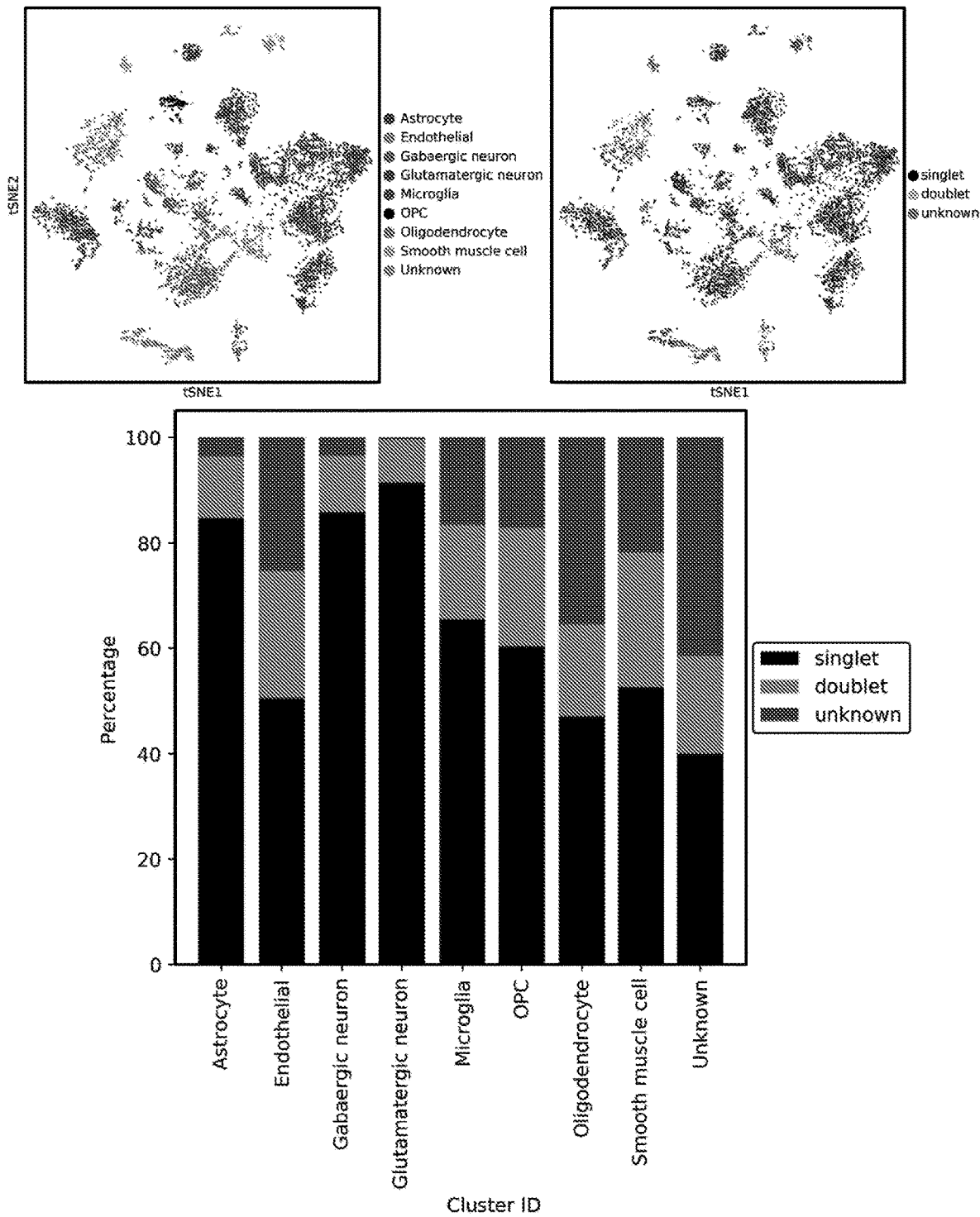
FIG. 8—illustrates a bar plot of the percentages of singlets, doublets and unknown for each cell type.

FIG. 7 is a bar plot showing the percentages of nuclei that belong to every cell type for each condition. Nuclei-hashing does not change cell type distribution significantly. FIG. 8 illustrates that the doublet/unknown rates are biased towards certain cell types in the brain.

Figure 12A:
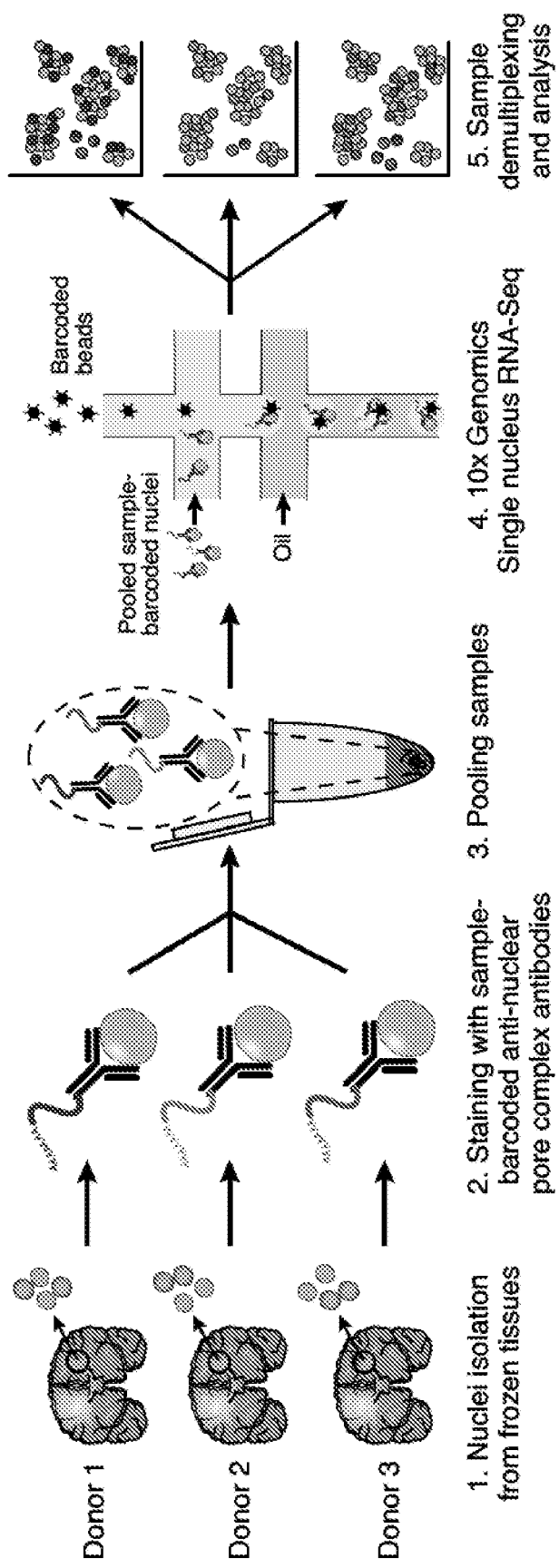
FIG. 12—Nuclei multiplexing using DNA-barcoded antibodies targeting the nuclear pore complex. a. Experimental workflow. Nuclei are isolated from frozen tissues and stained with DNA-barcoded antibodies targeting the nuclear pore complex (MAb414, Biolegend). The DNA barcode encodes a unique sequence representing each tissue sample, enabling sequence-based identification of each nucleus after pooling and profiling the different samples. b-e. Multiplexed and non-multiplexed samples of human cortex from 8 post-mortem donors yield comparable results. b. t-stochastic neighborhood embedding (tSNE) of single nucleus profiles (dots) colored by either cell type (b) or by type of protocol (c). Non-hashed control sample (blue) and hashed sample (orange) show similar patterns. d. Cell type frequencies observed for hashed (orange) and non-hashed control (blue) samples. The adjusted mutual information (AMI) is shown in the top left. e. Distributions of the number of expressed genes (y axis, left) in each cell type (x axis) in b, for nuclei from hashed (orange) and non-hashed control (blue) samples. f-g. Hashed single nuclei from all donors are similarly represented across cell type clusters. f. tSNE as in b colored by donor. g. Observed frequencies (y axis) of each cell type (x axis) per donor (color). The adjusted mutual information (AMI) is shown in the top left.

Applicants isolated nuclei from fresh-frozen murine or human cortex tissues, stained them with antibodies carrying a sample-specific DNA barcode, and pooled samples prior to droplet encapsulation for single-nucleus RNA-Seq (snRNA-Seq) (FIG. 12a). The DNA barcodes contain a polyA tail, thus acting as artificial transcripts that register the same bead barcode as nuclear transcripts, coupling the transcription profile to the sample of origin.

The additional antibody labeling step in the protocol did not alter the quality of transcriptional profiling compared to non-hashed snRNA-seq, in a side-by-side comparison of a hashed (antibody labeled) vs. non-hashed pool of cortex nuclei derived from eight human donors (Table 1). Applicants combined the expression profiles from both hashed and non-hashed datasets, followed by clustering and posthoc annotation with legacy cell type-specific signatures (FIG. 12b), recovering all cell types previously reported for such samples (Habib et al., 2017) (Methods). Both hashed and non-hashed nuclei were similarly represented across the recovered clusters (FIG. 12c), with an adjusted mutual information score of 0.0048 between cell types and experimental conditions (FIG. 12d, Methods), with only slight differences, such as a weak enrichment of glutamatergic neurons in the hashed samples, and similar cell type-specific numbers of recovered genes (FIG. 12e). Each cell type cluster had nuclei from all 8 donors (FIG. 12f) with only slightly differing frequencies (FIG. 12g), as expected for a diverse donor cohort (Habib et al., 2017) (Table 1). Notably, modifying the staining and washing buffers for nucleus hashing (Methods) compared to those used in cell-hashing (Stoeckius et al., 2018) improved the transcriptional similarity with the non-hashed control (FIG. 14a), and achieved a similar number of genes expressed per nucleus as the non-hashed control (FIG. 14b), whereas a PBS based buffer (used in cell-hashing(8)) had poorer performance (FIG. 14c). Applicants thus performed all experiments with these novel staining and washing buffers, except those with mouse samples. Collectively, these findings indicate that hashing preserves library quality and cell type distributions.

Figure 13B:
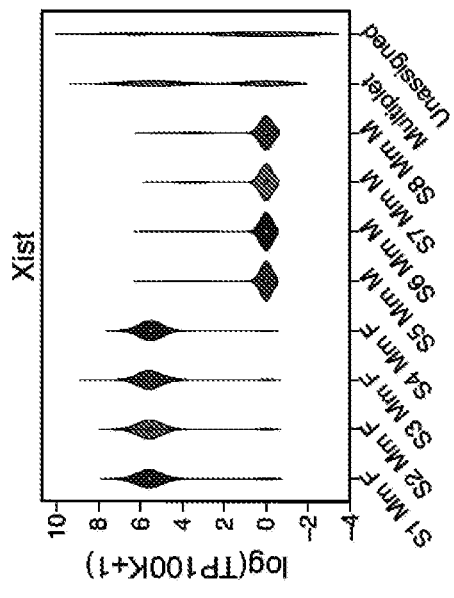
FIG. 13—Accurate sample assignment by DemuxEM allows efficient overloading of hashed samples. a. Sample assignment by DemuxEM. DemuxEM takes as input for each nucleus a count vector of hashtag UMIs (left) and estimates them as a sum of a background hashtag vector in that nucleus (right, grey histograms) and a signal sample assignment hashtag vector (right, color histograms). Shown are schematic examples: singlet assignment (top), multiplet detection (middle), and unassigned (bottom). b. Validation of DemuxEM assignment by gender mixing in isogenic mice. Distribution of Xist expression (y axis, log(TP100K+1)) from 8 mouse-derived cortex samples (samples 1-4 female, samples 5-8 male) that were pooled and demultiplexed. There is 94.8% agreement between DemuxEM-assigned sample hashtag identities and Xist expression among DemuxEM-detected singlets. c,d. DemuxEM assignments in species mixing of human and mouse cortex nuclei. c. Species mixing plot. Each nucleus (dot) is plotted by the number of RNA UMIs aligned to pre-mRNA mouse mm10 (x axis) and human GRCh38 (y axis) references, and colored by its DemuxEM-predicted hashtag sample identities for singlet human (red), singlet mouse (blue) or different multiplets (intra-species: green (mouse) and purple (human); inter-species: fuchsia). Donor 8 singlets (chartreuse) and multiplets (orange) are colored separately due to its large contribution to ambient hashtags d. Distribution of ambient hashtags matching the sample DNA barcode (x-axis) in the pool of 8 samples. DemuxEM identified sample8HuM as a disproportionate contributor to the hashtag background distribution. e,f. Validation of hashtag-based assignment of nuclei by natural genetic variation. Shown is the number of nuclei classified as sample singlet, multiplets or unassigned (rows, columns) by either natural genetic variation (columns) with Demuxlet(6), or based on hashtag UMIs (rows), with DemuxEM (e) or Seurat (f). 98.1% of nuclei identified by Demuxlet as singlets from a given donor are similarly identified by DemuxEM, and hashtag-based classification recovers more singlets than by natural variation. g-j. Nucleus hashing allows over-loading to reduce experimental costs. g. tSNE of combined data of 8 hashed human cortex samples profiled by snRNA-Seq at loading concentrations of 500, 1,500, 3,000 or 4,500 nuclei/µl. Single nucleus profiles (dots) are colored by cell type. h. Comparable distributions of the number of expressed genes (y axis) in each cell type (x axis) in g, for nuclei from each loading density. i. tSNE of single nucleus profiles (dots) as in g, colored by loading concentration. j. Comparable frequencies (y axis) across cell types in g (x axis) observed for different loading concentrations.
Figure 13C:
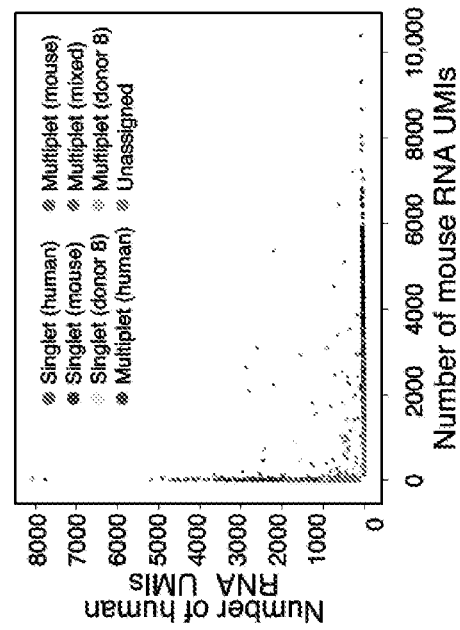
Figure 13A:
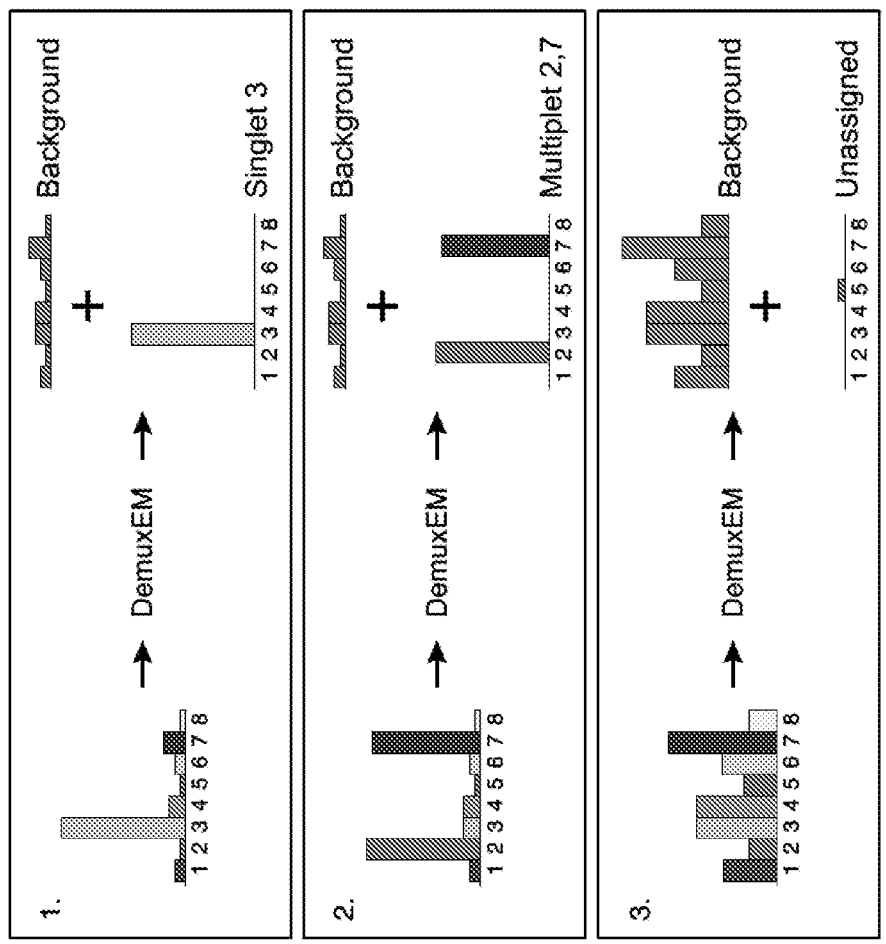

To probabilistically assign each nucleus to its sample barcode, Applicants developed DemuxEM, an Expectation-Maximization-based tool (FIG. 13a). For each nucleus, DemuxEM takes as input a vector of hashtag Unique Molecular Identifiers (UMIs) from that nucleus (FIG. 13a, left). The input vector is a mixture of signal hashtags, which reflect the nucleus' sample of origin, and background hashtags, which likely reflect ambient sample barcodes. Hashtags from the background have different probabilities of matching each of the sample barcodes. DemuxEM estimates this background distribution of sample barcode matching based on hashtags in empty droplets, which are likely to only contain background hashtags. With this background distribution as a reference, DemuxEM uses an Expectation-Maximization (EM) algorithm to estimate the fraction of hashtags from the background and then infer the signal hashtags by deducting the estimated background from the count vector. Once the signal has been identified, DemuxEM determines if this droplet encapsulated a single nucleus or a multiplet. For nuclei with low signal hashtags (e.g., <10 hashtags are from the signal), DemuxEM cannot determine the origin of the nucleus and marks it as 'unassigned' (Methods).

To assess confidence in calling the sample origin of hashed nuclei by their sample barcodes, Applicants next applied DemuxEM to pooled nuclei of male and female isogenic mice or of human and mouse, such that the single nucleus transcriptomes provided an orthogonal measure of the sample of origin. First, Applicants multiplexed nuclei isolated from two isogenic C57BL/6J mouse cortices, 4 technical replicates from each of a female and male mouse (Methods). For DemuxEM-identified singlets, there was a 94.8% agreement between DemuxEM-assigned sample hashtag identities and the expression level of Xist, a transcript predominantly expressed in females (FIG. 13b). Next, Applicants multiplexed 8 cortex samples, 4 from mouse and 4 from human (Table 1), comparing DemuxEM assignment as human or mouse singlets to their position in a "species-mixing plot" based on their number of RNA UMIs mapping to the human or mouse transcriptome (FIG. 13c). Overall, nuclei assigned by DemuxEM as human or mouse singlets (FIG. 13c, red and blue, respectively) express predominantly human or mouse reads, respectively (FIG. 13c, alignment along the Y and X axis). DemuxEM-predicted multiplets occur both on the species-specific axes for intra-species multiplets (FIG. 13c, green (mouse) and purple (human)) and off-axes for inter-species multiplets (FIG. 13c, fuchsia).

Applicants further leveraged the hashtags to address the sources of ambient hashtags in a pool of samples. In general, nuclei dissociated from tissue samples may be at risk of having higher levels of ambient hashtags compared to single-cell hashing, because the cytoplasm is broken up during lysis and nonspecific antibody binding to cytosolic content could contribute to the background. For example, in the species mixing experiment (FIG. 13c), there is a slant for the mouse nuclei, suggesting that there is more ambient mRNA from human than from mouse in this experiment, possibly reflecting the fact that human postmortem samples are obtained under less controlled conditions than mouse samples. Inspection of sample-specific contribution to the hashtag background signal showed that one of the human samples (donor 8) contributed disproportionally to the background signal (FIG. 13d), suggesting that this sample might have been of lower quality. The ability to identify which samples contribute to the background signal is an additional benefit of sample hashing.

Figures 13D, 13E, 13F:
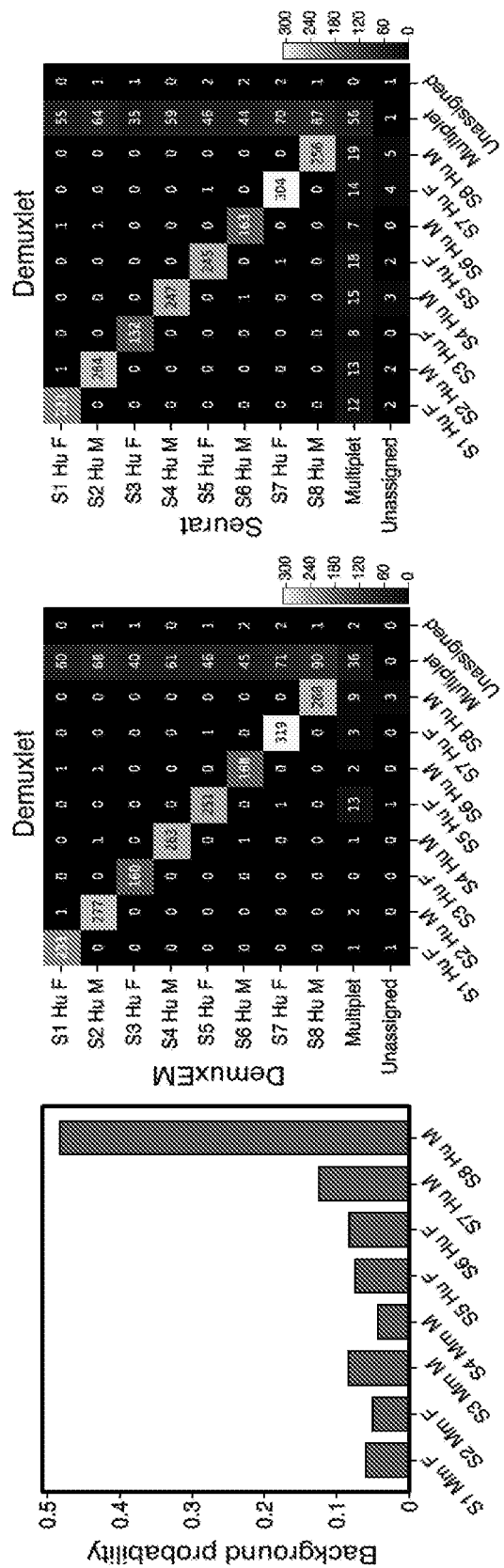
Figure 13H:
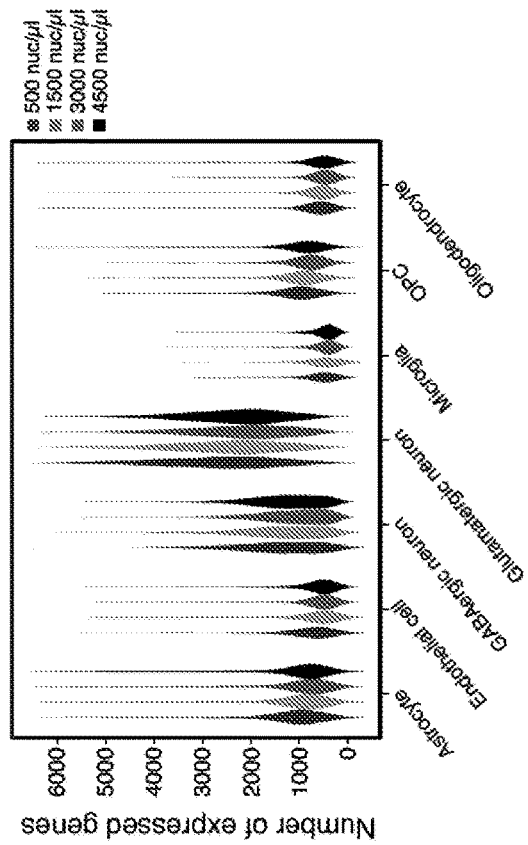
Figure 13J:
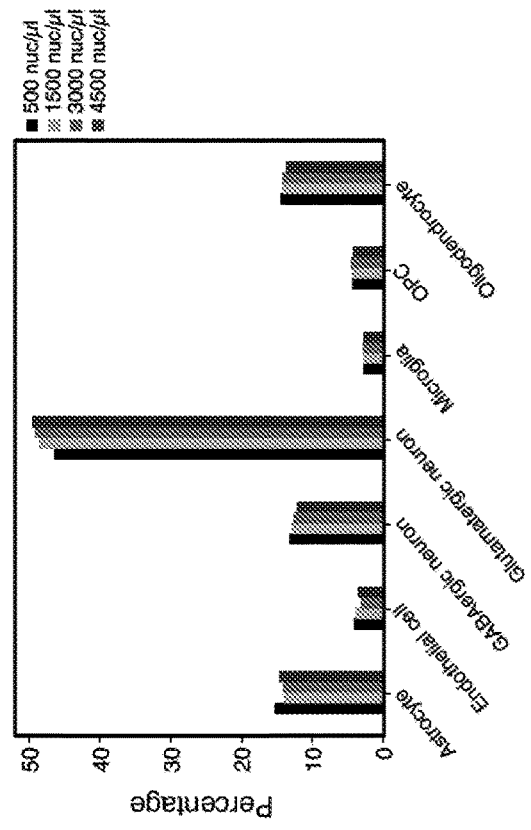

Next, Applicants validated the hashtag based demultiplexing with Demuxlet (Kang et al., 2018), an approach based on natural genetic variation. Applicants observed excellent agreement between the two methods for the 8 human cortex samples (FIG. 13e): on average, 98.1% of the nuclei identified by Demuxlet as single nuclei from a given donor are similarly identified by DemuxEM (FIG. 13e). Moreover, demultiplexing based on the hashtag data enables the identification of more singlets per donor when using either DemuxEM or Seurat, a package that includes single-cell hashing analysis (A. Butler, P. Hoffman, P. Smibert, E. Papalexi, R. Satija, Integrating single-cell transcriptomic data across different conditions, technologies, and species. Nat Biotechnol 36, 411-420 (2018)) (FIG. 13e,f, Table 2).

DemuxEM also offers a better estimation of the multiplet rate. The expected multiplet rate with the droplet-based scRNA-Seq when loading 7,000 cells is expected to be around 3.1% (X. Genomics, Chromium Single Cell 3' Reagent Kits User Guide. (2018)). When pooling 8 samples with equal proportions, there are 56 possible inter-sample doublet configurations and 8 possible intra-sample ones (the proportion of higher order multiplets is much lower), such that 87.5% (56/64) of the doublets are expected to contain nuclei from multiple samples, which can be identified by the hashing strategy. Since Applicants loaded 7,000 nuclei, Applicants expect a detectable multiplet rate of at least 2.7% (3.1*87.5%). DemuxEM, Seurat, and Demuxlet predicted multiplet rates of 2.8%, 6.5%, and 20.6%, respectively (Table 2).

Figure 13G:
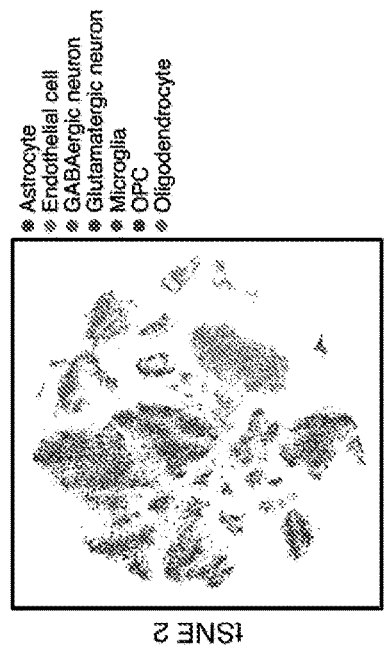
Figure 13I:
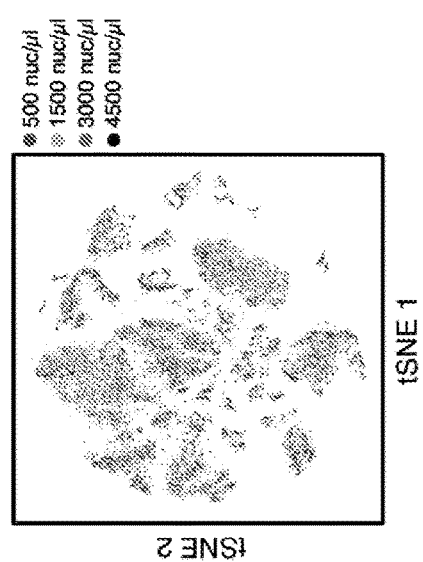

This ability to more accurately detect droplets that encapsulated multiple inter-sample nuclei allowed Applicants to load a higher concentration of nuclei for a given undetectable multiplet rate, thereby significantly lowering the cost per nucleus. To assess how 'over-loading' a higher concentration of nuclei affects library quality and cell type distributions, Applicants hashed and pooled another 8 human cortex samples (Table 1) and loaded a 10× channel with 14 μl of either ~500 nuclei/μl, 1,500 nuclei/μl, 3,000 nuclei/μl or 4,500 nuclei/μl. When sequencing these libraries at similar depth per nucleus, Applicants recovered similar numbers of expressed genes per nucleus for the different cell types (FIG. 13g,h). Moreover, nuclei from each loading concentration had similar transcriptional states (FIG. 13i) and maintained the same relative cell type frequencies (FIG.

Figure 15:
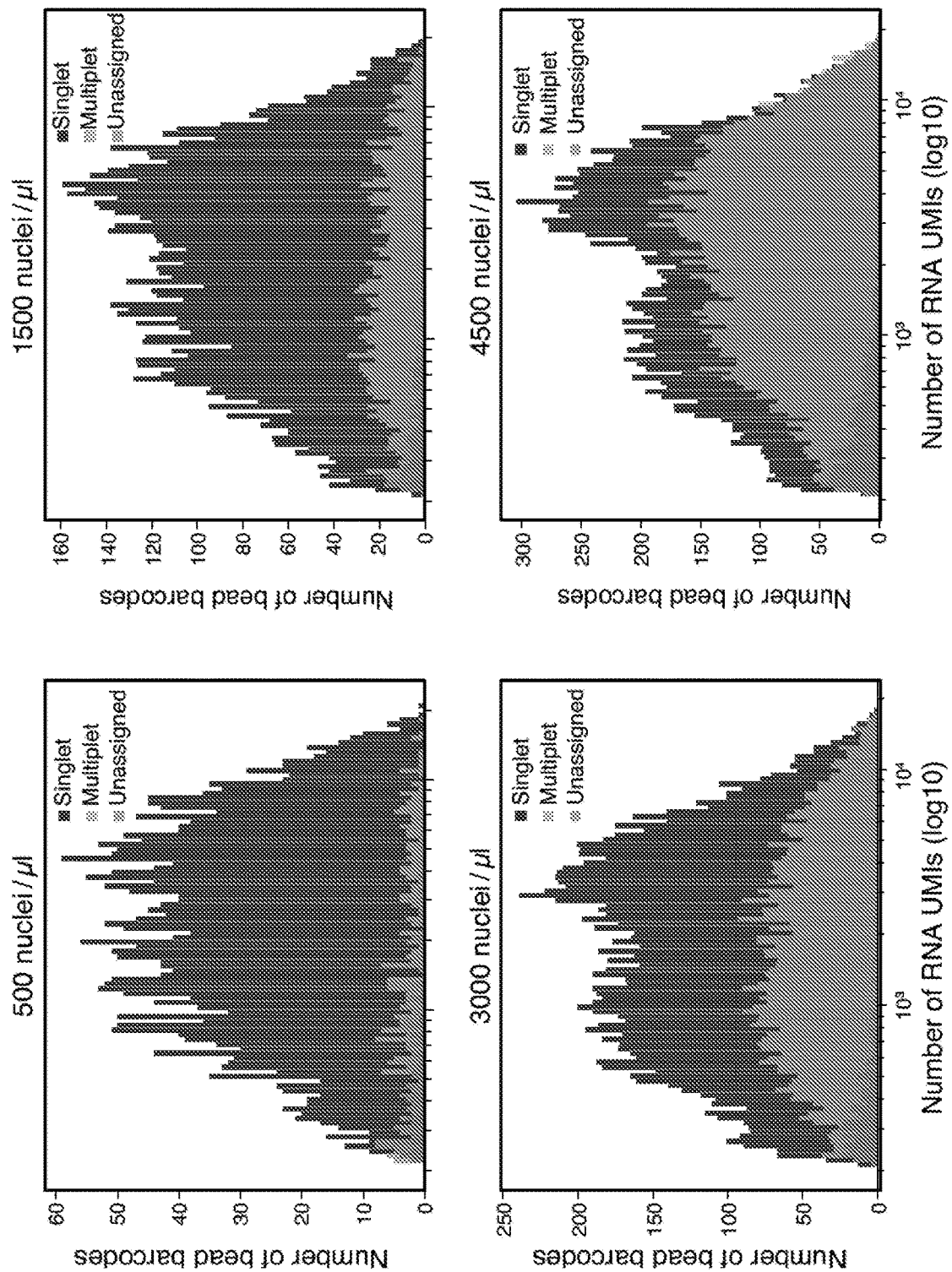
FIG. 15—Nuclei multiplets do not necessarily have a larger number of RNA UMIs. Distribution of number of bead barcodes (y axis) for beads with different numbers of detected UMIs (x axis), for singlets (blue), multiplets (orange) and unassigned droplets (green), in 8 hashed human cortex samples loaded at concentrations of 500, 1,500, 3,000 or 4,500 nuclei/µl. Although the multiplet rate rises with increasing loading concentrations, Applicants observe similar RNA UMI count distributions for multiplets and singlets, a feature not observed for single-cell hashing (Stoeckius et al., 2018).

13j). As expected, the proportion of multiplets increases with increased loading density (FIG. 15). Notably, nucleus multiplets do not typically show higher numbers of RNA UMIs compared to singlets (FIG. 15), in contrast to cell-hashing (Stoeckius et al., 2018). The lowest overall cost per nucleus (including nucleus-hashing antibodies, 10× library preparation and sequencing) was achieved for loading 14 µl of 3,000 nuclei/µl, resulting in a 56% cost reduction in the pricing structure, compared to the non-hashed loading density of 500 nuclei/µl (Methods, Table 3). Notably, these cost savings can also be achieved by splitting an individual sample into 8 hashed samples.

Discussion

Nucleus hashing is a principled method for multiplexing single nuclei. It reduces batch effects and costs and helps streamline large experimental studies. DemuxEM is a novel computational tool that enables accurate multiplet detection, nucleus identity assignment, and identification of the sources of ambient hashtag contamination. As nuclei, rather than cells, become the starting point of many additional assays—especially in epigenomics—it is likely that hashing can be extended to other single nucleus genomics assays. Together, nucleus hashing and DemuxEM allow Applicants to reliably interrogate cell types, cellular states, and functional processes in complex and archived tissues at a much larger scale than previously possible.

Materials and Methods

Human samples. The study was conducted under IRB approval L91020181. Applicants used frozen brain tissue from the dorsolateral prefrontal cortex (DLPFC) banked by two prospective studies of aging: the Religious Order Study (ROS) and the Memory and Aging Project (MAP), which recruit non-demented older individuals (age >65). Applicants selected samples for which Whole Genome Sequencing data was already available (P. L. De Jager et al., A multi-omic atlas of the human frontal cortex for aging and Alzheimer's disease research. Sci Data 5, 180142 (2018)). Applicants selected 10 males and 10 females (Table 1).

Mice. All mouse work was performed in accordance with the Institutional Animal Care and Use Committees (IACUC) and relevant guidelines at the Broad Institute and MIT, with protocol 0122-10-16. Adult female and male C57BL/6J mice, obtained from the Jackson Laboratory (Bar Harbor, Me.), were housed under specific-pathogen-free (SPF) conditions at the Broad Institute, MIT animal facilities.

Mouse tissue collection. Brains from C57BL/6J mice were obtained and split vertically along the sagittal midline. The cerebral cortices were separated and excess white matter was removed. Cortices were separated into microcentrifuge tubes and flash-frozen on dry ice. Frozen tissue was stored at ~80° C.

Nuclei isolation, antibody tagging, and snRNA-seq. A fully detailed, step-by-step protocol, is described in the Experimental Protocol section. Briefly, Applicants aimed to remove as much white matter and vasculature from the tissue before Applicants dounced it in lysis buffer, filtered the lysate, and resuspended it in staining buffer. A brief incubation with Fc receptor blocking solution is followed by incubation with the Total Seq Hashtag antibodies and 3 washes in ST-SB. Next, nuclei were counted and their concentration normalized to the desired loading concentration and pooled right before running the 10× Genomics single-cell 3' v2 assay (with minor adjustments listed in the detailed protocol), followed by library preparation and Illumina sequencing.

Buffer optimization. In cell-hashing experiments (Stoeckius et al., 2018), staining is performed with a PBS-based staining buffer (SB: 2% BSA, 0.02% Tween-20 in PBS). Applicants initially used this buffer during staining for nucleus hashing as well (gender-specific expression and species-mixing experiments) (Stoeckius et al, 2018). To further optimize the protocol, Applicants compared both a PBS-based staining buffer and a Tris-based staining buffer (ST-SB, Experimental protocol, 2% BSA, 0.02% Tween-20, 10 mM Tris, 146 mM NaCl, 1 mM $CaCl_2$, 21 mM $MgCl_2$) to a non-hashed control observing better performance in ST-SB, in terms of overall agreement with non-hashed controls and in the number of genes recovered per nucleus (FIG. 14). Applicants therefore recommend to perform the staining and washing steps of nucleus-hashing in ST-SB (Experimental protocol).

Single-nucleus RNA-Seq data analysis. Starting from BCL files obtained from Illumina sequencing, Applicants ran cellranger mkfastq to extract sequence reads in FASTQ format, followed by cellranger count to generate gene-count matrices from the FASTQ files. Since the data are from single nuclei, Applicants built and aligned reads to genome references with pre-mRNA annotations, which account for both exons and introns. Pre-mRNA annotations improve the number of detected genes significantly compared to a reference with only exon annotations (T. E. Bakken et al., Equivalent high-resolution identification of neuronal cell types with single-nucleus and single-cell RNA-sequencing. BioRxiv, (2018)). For human and mouse data, Applicants used the GRCh38 and mm10 genome references, respectively. To compare samples of interest (e.g., different loading concentrations), Applicants pooled their gene-count matrices together, and filtered out low-quality nuclei identified based on any one of the following criteria: (1) a total number of expressed genes <200; (2) a total number of expressed genes >=6,000; or (3) a percentage of UMIs from mitochondrial genes >=10%. Applicants performed dimensionality reduction, clustering and visualization on the filtered count matrix as previously described (F. A. Wolf, P. Angerer, F. J. Theis, SCANPY: large-scale single-cell gene expression data analysis. *Genome Biol* 19, 15 (2018); and K. Shekhar et al., Comprehensive Classification of Retinal Bipolar Neurons by Single-Cell Transcriptomics. *Cell* 166, 1308-1323 e1330 (2016)). Specifically, Applicants selected highly variable genes as described in Macosko et al. (Macosko et al., 2015) with a z-score cutoff at 0.5, performed PCA and selected the top 50 principal components (PCs) (G. X. Zheng et al., Massively parallel digital transcriptional profiling of single cells. *Nat Commun* 8, 14049 (2017)), clustered the data based on the 50 selected PCs using the Louvain community detection algorithm (V. A. Traag, Faster unfolding of communities: speeding up the Louvain algorithm. *Phys Rev E Stat Nonlin Soft Matter Phys* 92, 032801 (2015)) with a resolution at 1.3. Applicants identified cluster-specific gene expression by differential expression analyses between nuclei within the cluster and outside of the cluster (F. A. Wolf, P. Angerer, F. J. Theis, SCANPY: large-scale single-cell gene expression data analysis. *Genome Biol* 19, 15 (2018)) using Welch's t-test and Fisher's exact test; controlled false discovery rates (FDR) at 5% using the Benjamini-Hochberg procedure (Y. Benjamini, Y. Hochberg, Controlling the False Discovery Rate—a Practical and Powerful Approach to Multiple Testing. *J Roy Stat Soc B Met* 57, 289-300 (1995)), and annotated putative cell types based on legacy signatures of human and mouse brain cells. Applicants visualized the reduced dimensionality data using tSNE (D. Ulyanov, Multicore-tsne.github.com/DmitryUlyanov/Multicore-TSNE, (2016)) with a perplexity at 30. Note that in experiments 3 and 4 (Table 1), Applicants identified one cluster that did not express any known cell type markers and had the lowest median number of RNA UMIs among all clusters. Applicants removed it from further analysis, and repeated the above analysis workflow, except the low-quality nucleus filtration step.

DemuxEM. Suppose Applicants multiplex n samples together. For each droplet, Applicants have a count vector of hashtag UMIs from each sample, $(c_1, \ldots, c_n)$. Each hashtag UMI in the vector can either originate from a properly stained nuclear pore complex (signal) or come from ambient hashtag UMIs (background). Applicants define $\Theta=(\theta_0, \theta_1, \ldots, \theta_n)$, where $\theta_0$ probability that a hashtag is from the background, and $\theta_1, \ldots, \theta_n$ are the probabilities that the hashtag UMI is true signal $1, \ldots, n$. If a hashtag UMI is from the background, Applicants denote $P=(p_1, \ldots, p_n)$ as the probabilities that this hashtag matches the barcode sequence of samples $1, \ldots, n$. In addition, Applicants require $\sum_{i=1}^{n} p_i = 1$.

The probability of generating a hashtag that matches sample i's barcode sequence is:

$$P(\text{hashtag}=i) = \theta_0 \cdot p_i + \theta_i$$

And the log-likelihood of generating the hashtag count vector is:

$$L(\Theta) = \sum_{i=1}^{n} c_i \log(\theta_0 p_i + \theta_i) + \log \frac{\left(\sum_{i=1}^{n} c_i\right)!}{\prod_{i=1}^{n} c_i!}$$

DemuxEM estimates two sets of parameters: (1) the background distribution $P=(p_1, \ldots, p_n)$, and (2) $\Theta=(\theta_0, \theta_1, \ldots, \theta_n)$.

Applicants estimate the background distribution using empty droplets. To identify empty droplets, Applicants first collect all bead barcodes with at least one hashtag. Applicants then calculate the total number of hashtag UMIs each collected bead barcode has and performed a K-means clustering with k=2 on the total hashtag UMIs. The cluster with a lower mean hashtag UMI number was identified as empty droplets. If Applicants denote the set of identified empty droplets as B, Applicants can estimate the background distribution as follows:

$$p_i = \frac{\sum_{j \in B} c_{ji}}{\sum_{j \in B} \sum_{i=1}^{n} c_{ji}},$$

where $c_{ji}$ is the number of unique hashtags matching sample i in bead barcode j.

Applicants estimate $\Theta$ using an Expectation-Maximization algorithm. First, Applicants impose a sparse Dirichlet prior on $\Theta$, $\Theta \sim \text{Dir}(1, 0, \ldots, 0)$, to encourage the background distribution to explain as much data as possible. Applicants then follow the EM procedure below:

E step:

$$z_i = c_i \cdot \frac{\theta_i}{\theta_0 p_i + \theta_i}, i = 1, \ldots, n$$

$$z_0 = \sum_{i=1}^{n} c_i \cdot \frac{\theta_0 p_i}{\theta_0 p_i + \theta_i}$$

M step:

$$\theta_i = \frac{\max(z_i - 1, 0)}{z_0 + \sum_{i=1}^{n} \max(z_i - 1, 0)}, i = 1, \ldots, n$$

$$\theta_0 = \frac{z_0}{z_0 + \sum_{i=1}^{n} \max(z_i - 1, 0)}$$

Once Applicants have $\Theta$ estimated, Applicants first calculate the expected number of signal hashtag UMIs:

$$c_s = (1 - \theta_0) \cdot \sum_{i=1}^{n} c_i$$

If $c_s < 10$, the hashtag UMI vector contains too little signal and thus Applicants mark this droplet as 'unassigned'. Otherwise, Applicants count the number of samples that has at least 10% signal hashtag UMIs, $$\left| \left\{ i \mid \frac{\theta_i}{1 - \theta_0} \geq 0.1 \right\} \right|.$$

If this number is 1, the droplet is a singlet. Otherwise, it is a multiplet.

Estimation of cost per single nucleus in the overloading experiment. Applicants estimate the reduction in cost per single nucleus for a given pricing structure, assuming X for loading one 10× channel, Y for sequencing one Hi Seq lane, and Z for the TotalSeq nuclei hashtag cost per hashed sample, to allow readers to determine the costs for their own pricing structures. Applicants sequenced 4 HiSeq lanes in total for four overloading experiments, with proportions roughly as 1:3:6:9 (500 nuc/µl:1,500 nuc/µl:3,000 nuc/µl:4,500 nuc/µl). Based on these values, the sequencing costs for the four settings are $$\frac{4}{19}Y, \frac{12}{19}Y, \frac{24}{19}Y, \text{ and } \frac{36}{19}Y$$

respectively. Adding the 10× channel cost of X, and the TotalSeq nuclei hashtag costs of 8Z, the final cost for each setting $$X + \frac{4}{19}Y + 8Z, X + \frac{12}{19}Y + 8Z, X + \frac{24}{19}Y + 8Z, \text{ and}$$

$$X + \frac{36}{19}Y + 8Z$$

respectively. Applicants then divide each cost by the total number of singlets Applicants detected (Table 3) to obtain cost per single nucleus in each overloading setting.

Tables

TABLE 1

Human Samples (listing SEQ ID NO: 1-20)

| projid | sex | age at death | Cogdx | PathoAD | RIN | PMI | WGS (NYGC ID) | WGS ID | In Figures | hashtag | Barcode | Experiment ID | HTO proportion |
|---|---|---|---|---|---|---|---|---|---|---|---|---|---|
| 21000504 | F | 85.9 | 1 | 0 | 8.27 | 6.25 | AKZF858 | SM-CTEFQ | 1, 2E&F, S1 | TotalSeq-A0451 | TTCCTGCCATTACTA | 3 | 20% |
| 10291856 | M | 78.7 | 1 | 0 | 7.44 | 7 | TPIP513 | SM-CTDTK | 1, 2E&F, S1 | TotalSeq-A0452 | CCGTACCTCATTGTT | 3 | 20% |
| 20665307 | F | 95.2 | 1 | 1 | 7.47 | 5.33 | BBTC972 | SM-CJK4M | 1, 2E&F, S1 | TotalSeq-A0453 | GGTAGATGTCCTCAG | 3 | 20% |
| 10490993 | M | 86.5 | 1 | 1 | 8.08 | 7 | QYOD586 | SM-CJIX6 | 1, 2E&F, S1 | TotalSeq-A0454 | TGGTGTCATTCTTGA | 3 | 20% |
| 20603141 | F | 91.2 | 4 | 0 | 7.57 | 5 | WABT159 | SM-CTDSB | 1, 2E&F, S1 | TotalSeq-A0455 | ATGATGAACAGCCAG | 3 | 20% |
| 10290427 | M | 96.5 | 4 | 0 | 7.98 | 3.08 | UUQD519 | SM-CTDQF | 1, 2E&F, S1 | TotalSeq-A0456 | CTCGAACGCTTATCG | 3 | 20% |
| 29933130 | F | 94 | 4 | 1 | 7.39 | 4.42 | RPAQ271 | SM-CJIY9 | 1, 2E&F, S1 | TotalSeq-A0458 | TGACGCCGTTGTTGT | 3 | 20% |
| 11302830 | F | 85.8 | 4 | 1 | 8.41 | 1.5 | WKNN509 | SM-CTDQW | 1, 2E&F, S1 | TotalSeq-A0459 | GCCTAGTATGATCCA | 3 | 20% |
| 61142759 | F | 92.3 | 1 | 0 | 8.46 | 2.5 | RVJG598 | SM-CJIYW | 2G-J, S2 | TotalSeq-A0451 | TTCCTGCCATTACTA | 4 | 10% |
| 15738428 | M | 85.2 | 1 | 1 | 8.46 | 2.33 | XTFG797 | ROS15738428 | 2G-J, S2 | TotalSeq-A0452 | CCGTACCTCATTGTT | 4 | 10% |
| 21181988 | F | 92.2 | 1 | 0 | 8.34 | 3.08 | STVZ150 | SM-CTDTS | 2G-J, S2 | TotalSeq-A0453 | GGTAGATGTCCTCAG | 4 | 10% |
| 10271474 | M | 76.3 | 1 | 1 | 8.29 | 2.5 | YZUM149 | SM-CTEI7 | 2G-J, S2 | TotalSeq-A0454 | TGGTGTCATTCTTGA | 4 | 10% |
| 93462021 | F | 93 | 4 | 0 | 7.61 | 4.72 | OGLG380 | SM-CJGNL | 2G-J, S2 | TotalSeq-A0455 | ATGATGAACAGCCAG | 4 | 10% |
| 15420223 | M | 85.4 | 4 | 0 | 7.62 | 7.42 | UTGY293 | SM-CTDSN | 2G-J, S2 | TotalSeq-A0456 | CTCGAACGCTTATCG | 4 | 10% |
| 50403446 | F | 89.3 | 4 | 1 | 7.39 | 6.75 | DSLV819 | SM-CJEJG | 2G-J, S2 | TotalSeq-A0458 | TGACGCCGTTGTTGT | 4 | 10% |
| 10262905 | M | 90.7 | 4 | 1 | 8.04 | 9.58 | YFJR065 | SM-CTEE4 | 2G-J, S2 | TotalSeq-A0459 | GCCTAGTATGATCCA | 4 | 10% |
| 20124321 | F | 86.7 | 3 | 1 | 8.30 | 1.583333333 | JPGK989 | SM-CJGJ9 | 2C | TotalSeq-A0455 | ATGATGAACAGCCAG | 2 | 20% |
| 20152393 | F | 80.9 | 4 | 1 | 7.06 | 1.75 | INJM983 | SM-CJGGV | 2C | TotalSeq-A0456 | CTCGAACGCTTATCG | 2 | 20% |
| 11200645 | M | 83.7 | 1 | 1 | 7.54 | 4.25 | NFRB314 | SM-GLE | 2C | TotalSeq-A0457 | CTTATCACCGCTCAA | 2 | 20% |
| 10100150 | M | 84.7 | 4 | 1 | 6.44 | 11 | — | — | 2C | TotalSeq-A0458 | TGACGCCGTTGTTGT | 2 | 20% |

TABLE 1-continued

Mouse Samples (listing SEQ ID NO: 21-32)

| Mice | sex | In Figures | hashtag | Barcode | Experiment | HTO proportion |
|---|---|---|---|---|---|---|
| C57BL/6J | Female | 2C | TotalSeq-A0451 | TTCCTGCCATTACTA | 2 | 20% |
| C57BL/6J | Female | 2C | TotalSeq-A0452 | CCGTACCTCATTGTT | 2 | 20% |
| C57BL/6J | Male | 2C | TotalSeq-A0453 | GGTAGATGTCCTCAG | 2 | 20% |
| C57BL/6J | Male | 2C | TotalSeq-A0454 | TGGTGTCATTCTTGA | 2 | 20% |
| C57BL/6J | Female | 2B | TotalSeq-A0451 | TTCCTGCCATTACTA | 1 | 20% |
| C57BL/6J | Female | 2B | TotalSeq-A0452 | CCGTACCTCATTGTT | 1 | 20% |
| C57BL/6J | Female | 2B | TotalSeq-A0453 | GGTAGATGTCCTCAG | 1 | 20% |
| C57BL/6J | Female | 2B | TotalSeq-A0454 | TGGTGTCATTCTTGA | 1 | 20% |
| C57BL/6J | Male | 2B | TotalSeq-A0455 | ATGATGAACAGCCAG | 1 | 20% |
| C57BL/6J | Male | 2B | TotalSeq-A0456 | CTCGAACGCTTATCG | 1 | 20% |
| C57BL/6J | Male | 2B | TotalSeq-A0457 | CTTATCACCGTCAA | 1 | 20% |
| C57BL/6J | Male | 2B | TotalSeq-A0458 | TGACGCCGTTGTTGT | 1 | 20% |

TABLE 2

| Method | Singlet | Doublet | Unknown | Total | Multiplet rate |
|---|---|---|---|---|---|
| demuxEM | 2,435 | 69 | 5 | 2,509 | 2.8% |
| demuxlet | 1,982 | 517 | 10 | 2,509 | 20.6% |
| Seurat | 2,327 | 162 | 20 | 2,509 | 6.5% |

TABLE 3

| | Nuclei loading concentrations | | | |
|---|---|---|---|---|
| Nuclei Type | 500 nuc/ul | 1500 nuc/ul | 3000 nuc/ul | 4500 nuc/ul |
| Singlet | 3276 | 9013 | 13578 | 16170 |
| Multiplet | 242 | 1805 | 5428 | 11130 |
| Unknown | 102 | 212 | 371 | 792 |
| Total number of nuclei | 3620 | 11030 | 19377 | 28092 |
| Total cost | $X + 4/19 * Y + 8Z$ | $X + 12/19 * Y + 8Z$ | $X + 24/19 * Y + 8Z$ | $X + 36/19 * Y + 8Z$ |
| Cost per nucleus | $(X + 4/19 * Y + 8Z)/3276$ | $(X + 12/19 * Y + 8Z)/9013$ | $(X + 24/19 * Y + 8Z)/13578$ | $(X + 36/19 * Y + 8Z)/16170$ |
| Savings [%] | $(1 - (X + 4/19 * Y + 8Z)/(X + 4/19 * Y)) * 100$ | $(1 - ((X + 12/19 * Y + 8Z)/9013)/((X + 4/19 * Y)/3276)) * 100$ | $(1 - ((X + 24/19 * Y + 8Z)/13578)/((X + 4/19 * Y)/3276)) * 100$ | $(1 - ((X + 36/19 * Y + 8Z)/16170)/((X + 4/19 * Y)/3276)) * 100$ |
| Total cost non-hashed 500 nuc/ul | $X + 4/19 * Y$ | | | |
| cost per nucleus non-hashed 500 nuc/ul | $(X + 4/19 * Y)/3276$ | | | |
| 10x | X | per channel | | |
| HiSeq cost | Y | per lane | | |
| TotalSeq nuclei Hashtag | Z | per hashed sample (1 ug) | | |

Experimental Protocol

| Materials | | |
|---|---|---|
| NAME | CATALOG # | VENDOR |
| BSA-Molecular Biology Grade-12 mg | B9000S | New England Biolabs |
| Dounce homogenizers | D8938-1SET | Sigma |
| Corning™ Falcon™ Test Tube with Cell Strainer Snap Cap | 08-771-23 | Fisher Scientific |
| Pre-Separation Filters (20 μm) | 130-101-812 | Miltenyi Biotec |
| Eppendorf® LoBind microcentrifuge tubes | Z666505-100EA | Sigma Aldrich |
| Human TruStain FcX™ | 422302 | BioLegend |
| Beckman Coulter SPRI SELECT REAGENT 5 ML | NC0406406 | Fisher Scientific |
| KAPA HiFi HotStart ReadyMix | NC0465187 | Fisher Scientific |

1. Prepare Buffers Fresh

NP40 Lysis Buffer (NST): 0.1% NP40, 10 mM Tris, 146 mM NaCl, 1 mM CaCl$_2$, 21 mM MgCl$_2$, 40 U/mL of RNAse inhibitor ST Wash Buffer: (10 mM Tris, 146 mM NaCl, 1 mM CaCl$_2$, 21 mM MgCl$_2$), 0.01% BSA (NEB B9000S), 40 U/mL of RNAse inhibitor ST Staining buffer (ST-SB): 2%BSA, 0.02% Tween-20, 10 mM Tris, 146 mM NaCl, 1 mM CaCl$_2$, 21 mM MgCl$_2$)

2. Tissue Lysis and Homogenizing

Nuclei were extracted as previously described (1) with the following minor modifications:

a) For each sample to barcode and pool: prepare a separate homogenizer and douncing pestles A & B. Add 1 ml NST buffer to the dounce homogenizer and keep on ice.

Note: Keep tissues/homogenate and buffers on ice throughout the protocol. Pre-cool the centrifuge to 4C and keep at 4C for all steps.

b) Cut a 50-200 mg section of frozen brain tissue with a scalpel and dissect to remove white matter and vasculature. Mince tissue and add it to the homogenizer.

c) with a total volume of 1 mL, dounce 20 times with pestle A followed by 20 times with pestle B.

d) Add 1 ml of ST buffer, filter through 35 μm filters (Fisher 08-771-23) and transfer filtered homogenate to a 15 mL tube.

e) Rinse the homogenizer with 3× 1 ml of ST buffer, filter through 35 μm filters (Fisher 08-771-23) and add to the filtered homogenate to add up to a final volume of 5 ml.

f) Immediately spin down at 500 g for 5 mins at 4C to pellet the nuclei in swing bucket rotor g) Remove Supernatant h) Resuspend nuclei in 200 μl of ST-SB, filter with 20 um (miltenyibiotec 130-101-812) and transfer to a lo-bind 1.5 ml tube (Sigma-Aldrich, Z666505-100EA)

Count Nuclei

Nuclei were counted using the Nexcelom Cellometer Vision 10× objective and a DAPI stain.

a) DAPI was diluted to 2.5 μg/μl in ST Buffer.

b) 20 μl of the DAPI was pipet mixed with 20 ul of the nuclei suspension and 20 μl was loaded onto a cellometer cell counting chamber of standard thickness (Nexcelom catalog number: CHT4-SD100-002) and counted using a custom assay with the dilution factor set to 2.

Hashtag Antibody Staining

Note: this part mirrors the cell-hashing protocol (8), with very minor differences.

a) Add 10 μl Fc Blocking reagent (Biolegend 422302) per 1-2M of nuclei in 100 μl of ST-SB/nuclei and incubate for 5 minutes at 4C.

b) Add 1 μg of single nuclei hashing antibody per 100 μl of ST-SB/nuclei mix and incubate for 10 minutes at 4C.

c) Wash nuclei 3 times with 1.2 mL ST-SB, spin in swinging bucket rotor for 5 minutes at 500 g and 4° C.

d) Resuspend nuclei in ST-SB at 500-3,000 cells/μl.

e) Filter nuclei through MACS Pre-Separation Filters (20 μm), and count nuclei to verify concentration after filtration. Adjust to desired concentration.

f) Pool all samples at desired proportions and immediately proceed to next step.

10× Genomics Single-Nuclei Sequencing

Load 14 μl of pooled sample on 10× Genomics single-cell 3' v2 assay and process as described until before cDNA amplification.

Library Preparation
a) To increase yield of HTO products during the 10x Genomics cDNA amplification step: Add 1 µl of 2 µM HTO PCR additive primer (SEQ ID NO: 33)
(5'GTGACTGGAGTTCAGACGTGTGC*T*C)

b) After cDNA amplification: Separate HTO-derived cDNAs (<180 bp) and mRNA-derived cDNAs (>300 bp). Perform SPRI selection to separate mRNA-derived and antibody-oligo-derived cDNAs. DO NOT DISCARD SUPERNATANT FROM 0.6x SPRI. THIS CONTAINS THE HASHTAGS.
c) Add 0.6x SPRI (Beckman Coulter, B23317) to cDNA reaction as described in 10x Genomics protocol.
d) Incubate 5 minutes and place on magnet. Supernatant contains hashtags, and beads contain full length mRNA-derived cDNAs.

Library Preparation for mRNA-Derived cDNA >300 bp (Bead Fraction)

Proceed with standard 10x protocol for cDNA sequencing library preparation.

Library Preparation for mRNA-Derived cDNA <300 bp (Supernatant Fraction)

Purify Hashtags using two 2x SPRI purifications per manufacturer protocol:
Add 1.4x SPRI to supernatant to obtain a final SPRI volume of 2x SPRI.
Transfer entire volume into a low-bind 1.5 mL tube.
Incubate 10 minutes at room temperature.
Place tube on magnet and wait ~2 minutes until solution is clear.
Carefully remove and discard the supernatant.
Add 400 µl 80% ethanol to the tube without disturbing the pellet and stand for 30 seconds (only one ethanol wash).
Carefully remove and discard the ethanol wash.
Centrifuge tube briefly and return it to magnet.
Remove and discard any remaining ethanol.
Resuspend beads in 50 µl water.
Perform another round of 2x SPRI purification by adding 100 µl SPRI reagent directly onto resuspended beads.
Mix by pipetting, and incubate 10 minutes at room temperature.
Place tube on magnet and wait ~2 minutes until solution is clear.
Carefully remove and discard the supernatant.
Add 200 µl 80% ethanol to the tube without disturbing the pellet and let stand for 30 seconds (first Ethanol wash).
Carefully remove and discard the ethanol wash.
Add 200 µl 80% ethanol to the tube without disturbing the pellet and let stand for 30 seconds (second Ethanol wash).
Carefully remove and discard the ethanol wash.
Centrifuge tube briefly and return it to magnet.
Remove and discard any remaining ethanol and allow the beads to air dry for 2 minutes (do not over-dry beads).
Resuspend beads in 90 µl water.
Mix vigorously by pipetting and incubate at room temperature for 5 minutes.
Place tube on magnet and transfer clear supernatant into PCR well.
Prepare 100 µL PCR reaction with purified small fraction:
45 µl purified Hashtag fraction
50 µl 2x KAPA Hifi PCR Master Mix.
2.5 µl TruSeq DNA D7xx_s primer (containing i7 index) 10 µM. (i.e.

D701:
(SEQ ID NO: 34)
5'CAAGCAGAAGACGGCATACGAGATCGAGTAATGTGACTGGAGTTCAGA
CGTGT*G*C)

2.5 µl SI PCR oligo at 10 µM (SI

PCR:
(SEQ ID NO: 35)
5'AATGATACGGCGACCACCGAGATCTACACTCTTTCCCTACACGACGC*
T*C)

Cycling Conditions:
95° C. 3 min
95° C. 20 sec|
64° C. 30 sec|~8 cycles
72° C. 20 sec|
72° C. 5 min
Perform 1.6x SPRI purification by adding 160 µl SPRI reagent.
Incubate 5 minutes at room temperature.
Place tube on magnet and wait 1 minute until solution is clear.
Carefully remove and discard the supernatant.
Add 200 µl 80% ethanol to the tube without disturbing the pellet and let stand for 30 seconds (first ethanol wash).
Carefully remove and discard the ethanol wash.
Add 200 µl 80% ethanol to the tube without disturbing the pellet and let stand for 30 seconds (second ethanol wash).
Carefully remove and discard the ethanol wash.
Centrifuge tube briefly and return it to magnet.
Remove and discard any remaining ethanol and allow the beads to air dry for 2 minutes.
Resuspend beads in 20 µl water.
Pipette mix vigorously and incubate at room temperature for 5 minutes.
Place tube on magnet and transfer clear supernatant to PCR tube.
Quantify Library
Quantify library by standard methods (QuBit, BioAnalyzer). Hashtag library will be around 180 bp.
Sequence
Combine mRNA library and HTO library (~90% mRNA to 10% HTO), and sequence with the regular 10x RNA-seq read structure:
Read 1=26
Read 2=55 bp
Index 1=8 bp
Index 2=n/a Example 2

Perturb-seq and Optical Screens

This example shows exemplary methods for genome-wide genetic screens using Perturb-seq and optical screens, e.g., to understand circular circuits under control of specific genes.

Guide RNA molecules (gRNA) are introduced into bone marrow-derived dendritic cells (BMDCs). The guide RNA molecules may be introduced by transduction with lentiviruses expressing the guide RNA molecules at MOI of 1. After transduction, the cells are encapsulated in droplets with beads coated with oligos containing unique molecular identifiers and cellular barcodes. The identity of the gRNA is also recorded in each cell.

The gRNAs are labeled with optically detectable labels, e.g., fluorescent labels. The cells are screened and selected based on the optically detectable labels. In some cases, only a subset of cells can be selected for further testing, e.g., sequencing. In some cases, a smaller Perturb-seq and a larger optical pooled screen are performed. By joint embedding, the expression phenotype for perturbations only in the optical screen are predicted.

Figure 10:
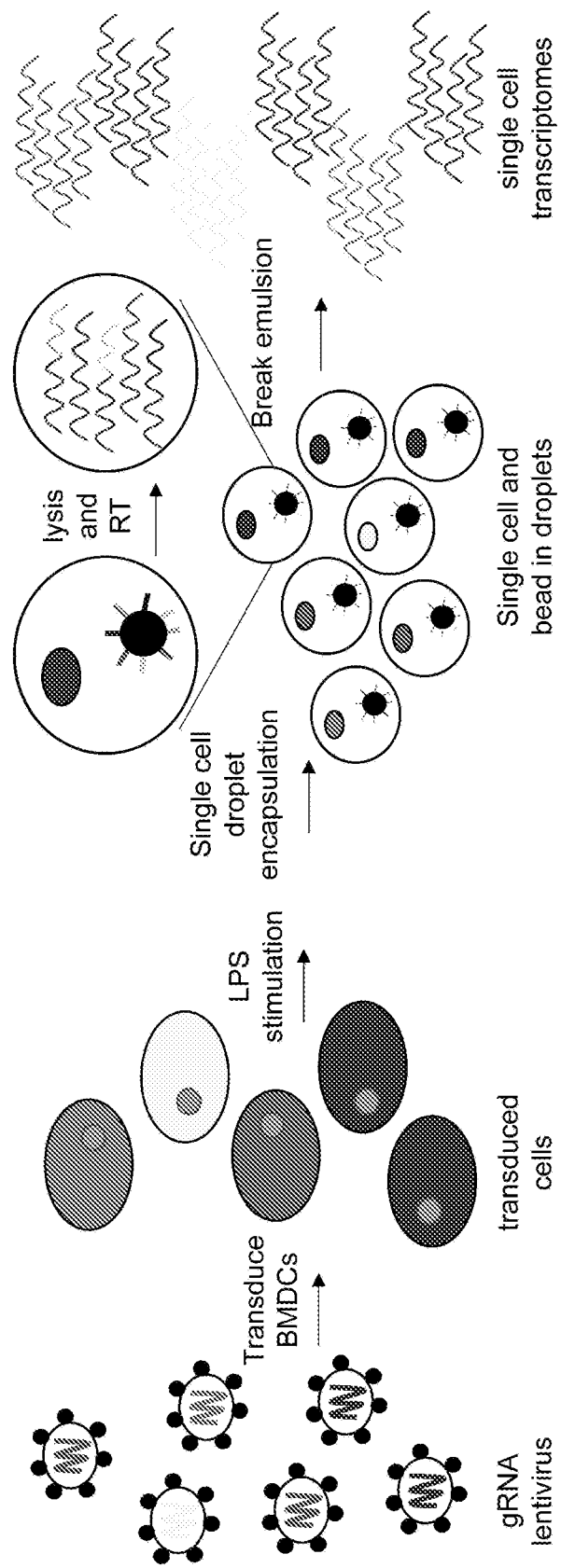
FIG. 10—illustrates an exemplary work flow for Perturb-seq.

The emulsion is broken and pooled single cell transcriptomes are sequenced via Illumina. General workflow of the method is shown in FIG. 10.

A second expression screen is then performed to validate some or all of the screen results.

The effect of perturbed genes in many different cellular contexts and in response to different stimuli (e.g., LPS activation of innate immune cells) can be determined using the methods herein.

Figure 11:
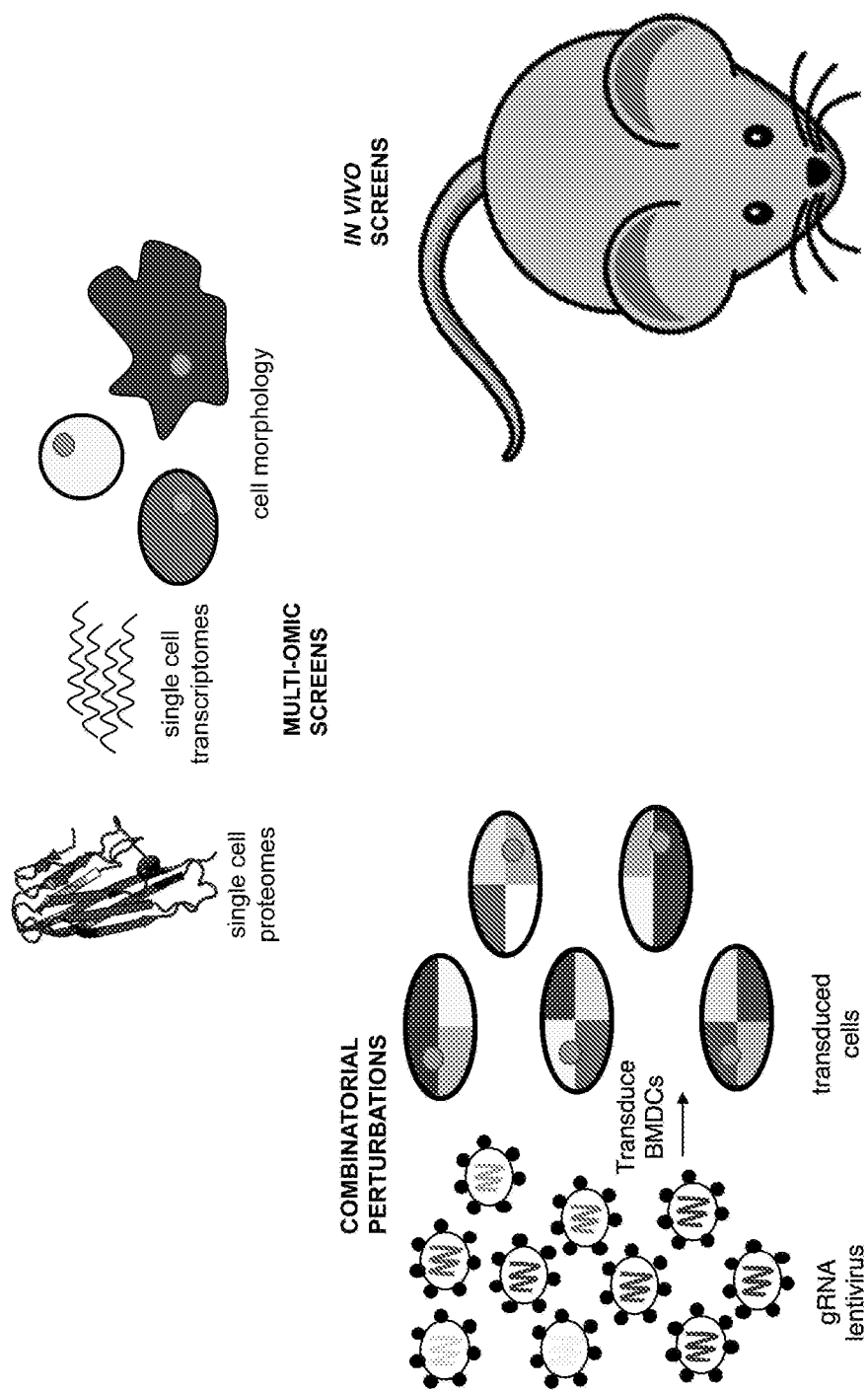
FIG. 11—illustrates exemplary work flows for tests combined with Perturb-seq and optical screen.

In some cases, combinational perturbations may be tested. The screen methods are combined with multi-omics tests, such as assaying protein levels and/or other functional readouts). In vivo perturbations may also be tested (FIG. 11).

Example 3

Decomposing Doublets

This example shows exemplary methods for decomposing doublets. Doublets may refer to two cells in a single droplet in droplet-based single cell sequencing technologies. Conventional experiments are generally designed to avoid generation of doublets, and when detected during analysis, the data regarding the doublets can be removed from future analysis. The methods herein used decompression algorithms to decompress doublets, making them useful.

Efforts to hash and overload cells have proven successful, allowing for recovery of many more single cells per 10× channel. Overloading nuclei may provide a unique opportunity to increase recovery (e.g., overload more nuclei than cells). Motor cortex nuclei were loaded onto 4 10× channels. Mathematical models were used to decompress multiples, recovering what would have been the transcriptomes of single nuclei. Other types of tissues or cells may be used too.

Specifically, nuclei 10× overloading may be tested as follows: in 4 separate channels, 15,000 nuclei, 50,000 nuclei, 100,000 nuclei, and 330,000 nuclei were loaded. The 10,000 loaded nuclei channel forms ground truth (mostly singlets). The number of nuclei from overloaded channels and the ability to decompress doublets in overloaded channels are tested.

The Cell Ranger counts were performed for the 4 overload mouse cortex nuclei channels. The results are summarized in the table below. Deeper sequence may result in higher genes numbers per cell.

| Nuclei loaded | Estimated 10X cell barcodes | Current reads per cell | Genes per cell |
| --- | --- | --- | --- |
| 15,000 | 8,439 | 5,943 | 309 |
| 50,000 | 24,340 | 3,764 | 286 |
| 100,000 | 53,450 | 5,919 | 406 |
| 330,000 | 48,822 | 8,438 | 492 |

Example 4

In Vivo Perturb-seq

In certain embodiments, Perturb-seq of target genes are performed in vivo. The perturbation methods and tools described herein allow reconstructing of a cellular network or circuit. In one embodiment, the method comprises (1) introducing single-order or combinatorial perturbations to a population of cells, (2) measuring genomic, genetic, proteomic, epigenetic and/or phenotypic differences in single cells and (3) assigning a perturbation(s) to the single cells. Not being bound by a theory, a perturbation may be linked to a phenotypic change, preferably changes in gene or protein expression. In preferred embodiments, measured differences that are relevant to the perturbations are determined by applying a model accounting for co-variates to the measured differences. The model may include the capture rate of measured signals, whether the perturbation actually perturbed the cell (phenotypic impact), the presence of subpopulations of either different cells or cell states, and/or analysis of matched cells without any perturbation. In certain embodiments, the measuring of phenotypic differences and assigning a perturbation to a single cell is determined by performing single cell RNA sequencing (RNA-seq). In preferred embodiments, the single cell RNA-seq is performed by any method as described herein (e.g., Drop-seq, InDrop, 10× genomics). In certain embodiments, unique barcodes are used to perform Perturb-seq. In certain embodiments, a guide RNA is detected by RNA-seq using a transcript expressed from a vector encoding the guide RNA. The transcript may include a unique barcode specific to the guide RNA. Not being bound by a theory, a guide RNA and guide RNA barcode is expressed from the same vector and the barcode may be detected by single cell RNA-seq. Not being bound by a theory, detection of a guide RNA barcode is more reliable than detecting a guide RNA sequence, reduces the chance of false guide RNA assignment and reduces the sequencing cost associated with executing these screens. Thus, a perturbation may be assigned to a single cell by detection of a guide RNA barcode in the cell. In certain embodiments, a cell barcode is added to the RNA in single cells, such that the RNA may be assigned to a single cell. Generating cell barcodes is described herein for single cell sequencing methods. In certain embodiments, a Unique Molecular Identifier (UMI) is added to each individual transcript and protein capture oligonucleotide. Not being bound by a theory, the UMI allows for determining the capture rate of measured signals, preferably the binding events or the number of transcripts captured. Not being bound by a theory, the data is more significant if the signal observed is derived from more than one protein binding event or transcript. In preferred embodiments, perturbations are detected in single cells by detecting a guide RNA barcode expressed as a polyadenylated transcript, a cell barcode, and a UMI. In certain example embodiments, the guide RNA may further encode an optical barcode as described in WO/2016/149422 entitled "Encoding of DNA Vector Identity via Iterative Hybridization Detection of a Barcode Transcript" filed Mar. 16, 2016. Optical barcode allows for identification of delivery of guide RNAs and association of such delivery with a particular cell phenotype. Assessment of optical barcodes and cell phenotype may be carried out prior insertion into an experimental model or described below, in the experimental model, or after removal from the experimental model.

The ability to generate high throughput in vivo single cell data provides transcriptional insight to the heterogeneity of cell states. However, the ability to perturb each candidate gene (e.g., regulatory candidate) in in vivo mouse models is laborious and time-consuming, and has become a limiting factor in the mapping and annotation of regulatory drivers. To enable the efficient testing of tens of candidate regulators Applicants have adapted the Pertub-seq system to screen for regulators in vivo (e.g., tumor mouse models). In vivo Perturb-seq may be performed with a set of perturbations. The set of perturbations may be selected based on targets in a specific pathway or determined by RNA-seq or determined by performing Perturb-seq in vitro. The perturbations may preferably include up to 10, 20, 30, 40, 50, 60, 70, 80, 100 perturbations. In certain embodiments, more than 100 perturbations are screened by in vivo Perturb-seq.

In certain embodiments, Perturb-seq of target genes are performed in vivo.

In certain embodiments, target genes may be perturbed in cells ex vivo and introduced to an animal model in vivo. As used herein "experimental models" refer to models that resemble human conditions in phenotype or response to treatment but are induced artificially in the laboratory. Some examples include, but are not limited to implanting animals with tumors to model cancers and immunization of animals with an auto-antigen to induce an immune response to model autoimmune diseases (e.g., Experimental autoimmune encephalomyelitis (EAE), see, WO 2015/130968). Cells perturbed ex vivo may include, but are not limited to tumor cells (e.g., melanoma, such as B16F10 and colon cancer, such as CT26), immune cells (e.g., tumor infiltrating lymphocytes (TIL)), or tumor microenvironment cells (e.g., cancer associated fibroblasts, microglia). Not being bound by a theory, perturbation of targets in vivo allows for measuring the effects of the perturbations on phenotype in single cells in an in vivo context and may advantageously provide network connections and/or regulatory drivers previously undetected.

In certain embodiments, perturbed cells are extracted from an in vivo organism. For example, methods for isolating TILs are known in the art. Perturbed cells may be further isolated by sorting cells expressing a selectable marker, such as a fluorescent marker as described herein.

In certain embodiments, after determining Perturb-seq effects in cancer cells and/or primary T-cells, the cells are infused back to the tumor xenograft models to observe the phenotypic effects of genome editing. Not being bound by a theory, detailed characterization can be performed based on (1) the phenotypes related to tumor progression, tumor growth, immune response, etc. (2) the TILs that have been genetically perturbed by CRISPR-Cas9 can be isolated from tumor samples, subject to cytokine profiling, qPCR/RNA-seq, and single-cell analysis to understand the biological effects of perturbing the key driver genes within the tumor-immune cell contexts. Not being bound by a theory, this provides validation of TILs biology as well as novel therapeutic targets.

A CRISPR system may be delivered to primary mouse T-cells. Over 80% transduction efficiency may be achieved with Lenti-CRISPR constructs in CD4 and CD8 T-cells. Despite success with lentiviral delivery, recent work by Hendel et al, (Nature Biotechnology 33, 985-989 (2015) doi:10.1038/nbt.3290) showed the efficiency of editing human T-cells with chemically modified RNA, and direct RNA delivery to T-cells via electroporation. In certain embodiments, perturbation in mouse primary T-cells may use these methods.

In one exemplary embodiment, Applicants perturb a list of ~50 candidate regulators by applying a pooled screen to CD8 T cells, followed by their transfer to a B16OVA tumor mouse model (see, e.g., Overwijk and Restifo, B16 as a Mouse Model for Human Melanoma, Curr Protoc Immunol. 2001 May; CHAPTER: Unit-20.1). The OT-1 TCR is expressed on CD8+ T cells and is specific for the peptide OVA257-264. After perturbation, OT1+ TILs are extracted and sequenced, enabling the identification of the gene modified by perturbation along with the transcriptional and/or proteomic profile of each cell. In certain embodiments, a regularized regression model is used to identify genes that are regulators of distinct TIL transcriptional states, or of transcriptional modules within some states but not others. Applicants have optimized conditions in the OT1/OVA tumor model, validating that sufficient numbers of cells can be extracted following transfer to conduct in vivo Perturb-seq.

In other embodiments, the Perturb-seq constructs described herein are introduced to cells in vivo (e.g., animal model). The cells may be extracted from an animal model and subjected to single cell RNA-seq and/or single cell proteomics. The perturbation may be identified and assigned to the proteomic and gene expression readouts of single cells. The constructs may include tissue specific expression of the CRISPR enzyme, whereby perturbation of target genes occurs in specific cell types. The constructs may be introduced by a vector, such as viral vector, configured for targeting a specific cell type. The expression of the CRISPR enzyme may be under the control of a tissue specific regulatory element (i.e., promoter). Specific cell types include, but are not limited to immune cells (e.g., CD8+ T cells, CD4+ T cells, Tregs, monocytes).

In certain embodiments, perturbed cells may comprise a cell in a model non-human organism, a model non-human mammal that expresses a Cas protein, a mouse that expresses a Cas protein, a mouse that expresses Cpf1, a mouse that expresses Cas13a, a mouse that expresses Cas13b, a cell in vivo or a cell ex vivo or a cell in vitro (see e.g., WO 2014/093622 (PCT/US13/074667); US Patent Publication Nos. 20120017290 and 20110265198 assigned to Sangamo BioSciences, Inc.; US Patent Publication No. 20130236946 assigned to Cellectis; Platt et al., "CRISPR-Cas9 Knockin Mice for Genome Editing and Cancer Modeling" Cell (2014), 159(2): 440-455; "Oncogenic models based on delivery and use of the CRISPR-Cas systems, vectors and compositions," WO2014204723A1; "Delivery and use of the CRISPR-Cas systems, vectors and compositions for hepatic targeting and therapy," WO2014204726A1; and "Delivery, use and therapeutic applications of the CRISPR-Cas systems and compositions for modeling mutations in leukocytes," WO2016049251). The cell(s) may also comprise a human cell. Mouse cell lines may include, but are not limited to neuro-2a cells and EL4 cell lines (ATCC TIB-39). Primary mouse T cells may be isolated from C57/BL6 mice. Primary mouse T cells may be isolated from Cas9-expressing mice.

The mouse of Platt et al., 2014 may also be used in the present invention for in vivo Perturb-seq. Platt et al. established a Cre-dependent Cas9 knockin mouse and demonstrated in vivo as well as ex vivo genome editing using adeno-associated virus (AAV)-, lentivirus-, or particle-mediated delivery of guide RNA in neurons, immune cells, and endothelial cells. Using these mice, Platt et al. simultaneously modeled the dynamics of KRAS, p53, and LKB1, the top three significantly mutated genes in lung adenocarcinoma. Delivery of a single AAV vector in the lung generated loss-of-function mutations in p53 and Lkb1, as well as homology-directed repair-mediated Kras(G12D) mutations, leading to macroscopic tumors of adenocarcinoma pathology. In certain embodiments, Cre-dependent Cas9 knockin mice or any Cre-dependent CRISPR enzyme mouse (e.g., Cpf1) may be crossed with tissue-specific Cre transgenic or knockin mice to limit expression of the CRISPR enzyme to a specific cell type and limit in vivo Perturb-seq to specific cell types (see, e.g., Sharma and Zhu, Immunologic Applications of Conditional Gene Modification Technology in the Mouse, Curr Protoc Immunol. 2014; 105: 10.34.1-10.34.13). Most of the existing Cre mouse lines can be found at the CREATE (Coordination of resources for conditional expression of mutated mouse alleles) consortium (creline.org/), which includes the Cre mouse database at Mouse Genome Informatics (MGI, loxP.creportal.org/).

In certain embodiments, expression of Cre is limited to immune cells whereby the CRISPR enzyme is expressed exclusively in immune cells. In certain embodiments, the mouse is treated, such that the mouse has a disease phenotype (e.g., cancer, autoimmune disease). In one embodiment, the mouse expresses a CRISPR enzyme exclusively in immune cells in a mouse having a disease phenotype. In a specific embodiment, a Perturb-seq sgRNA library may be introduced to a tumor such that the perturbations occur in immune cells infiltrating the tumor. Tumor infiltrating lymphocytes may be extracted from the tumor and analyzed by a single cell RNA-seq and/or proteomics method as described herein. In alternative embodiments, immune cells are analyzed after perturbation in an autoimmune model.

Some commonly used Cre mice for studying the immune system and that are applicable for use in the present invention are summarized in the Table below (Tg refers to transgenic and KI refers to knock in).

| Name | Tg/KI | Expression in cell types | Note | Reference |
|---|---|---|---|---|
| ROSA26-CreER$^{T2}$ | KI | Most cells except those in the brain | High deletion efficiency with tamoxifen treatment both in vitro and in vivo | Seibler et al. (2003) |
| Vav-Cre | Tg | All hematopoietic lineages, testis and ovaries | High deletion efficiency; may cause germ line deletion in some offspring | de Boer et al. (2003) |
| CD2-Cre | Tg | Common lymphoid progenitors (CLPs) | High deletion efficiency; some modified CD2-Cre lines may only delete genes in T cells but not B cells | Zhumabekok et al. (1995); de Boer et al. (2003) |
| Lck-Cre | Tg | Early DN stage in the thymus | Deletion efficiency varies | Lee et al. (2001) |
| CD4-Cre | Tg | Late DN to DP stage, deleting floxed genes in both CD4 and CD8 T cells | High deletion efficiency | Lee et al. (2001) |
| CD4-CreER$^{T2}$ | Tg | Deleting floxed genes only CD4 but not CD8 T cells in the periphery | Inducible by tamoxifen; deletion efficiency up to 80% in vivo | Aghajani et al. (2012) |
| dLck-Cre (line 3779) | Tg | Late DP to SP stage | ~70% deletion efficiency in CD4 T cells; higher efficiency (80% to 90%) in CD8 T cells; very low in Tregs | Wang et al. (2001) |
| OX40-Cre | KI | Tregs and activated CD4$^+$ T cells | Endogenous OX40 gene is disrupted by Cre; very low efficiency in activated CD8 T cells | Yagi et al. (2010) |
| CD8a-Cre | Tg | Mature CD8$^+$ but not CD4$^+$ T cells | Also known as E8I-Cre; Cre expression driven by the core E8I enhancer and Cd8a promoter | Maekawa et al. (2008) |
| Granzyme-B-Cre | Tg | Activated CD4$^+$ and CD8$^+$ T cells | Cre driven by truncated granzyme B promoter | Jacob and Baltimore (1999) |
| Mb1-Cre | KI | Starting from Pre-Pro-B stage | Endogenous Mb1 gene encoding Igα signaling subunit of the BCR is disrupted by Cre; deletion efficiency is better than CD19-Cre | Hobeika et al. (2006) |
| CD19-Cre | KI | Starting Pro-B stage | Endogenous Cd19 gene is disrupted by Cre; deletion efficiency is 75% to 95% | Rickert et al. (1997) |
| CD19-CreER$^{T2}$ | BAC Tg | Similar to CD19-Cre, but its activity requires tamoxifen treatment | Inducible by tamoxifen; deletion efficiency 25% to 60% | Boross et al. (2009) |
| Foxp3-YFPCre | KI | Only in Foxp3$^+$ Tregs | YFP is dim; endogenous Foxp3 expression intact | Rubtsov et al. (2008) |
| Foxp3-GFPCreER$^{T2}$ | KI | Only in Foxp3$^+$ Tregs | Inducible but with low deletion efficiency (10% to 20%); endogenous Foxp3 expression intact | Rubtsov et al. (2010) |
| Id2-CreER$^{T2}$ | KI | Id2-expressing cells: epithelial cells in the lung distal tips as well as progenitor of ILCs and T cells | Inducible but with low deletion efficiency; endogenous Id2gene is disrupted by CreER$^{T2}$ | Rawlins et al. (2009) |

In one embodiment, CRISPR/Cas9 may be used to perturb protein-coding genes or non-protein-coding DNA. CRISPR/Cas9 may be used to knockout protein-coding genes by frameshifts, point mutations, inserts, or deletions. An extensive toolbox may be used for efficient and specific CRISPR/Cas9 mediated knockout as described herein, including a double-nicking CRISPR to efficiently modify both alleles of a target gene or multiple target loci and a smaller Cas9 protein for delivery on smaller vectors (Ran, F. A., et al., In vivo genome editing using *Staphylococcus aureus* Cas9. Nature. 520, 186-191 (2015)). In one embodiment, perturbation is by deletion of regulatory elements. Non-coding elements may be targeted by using pairs of guide RNAs to delete regions of a defined size, and by tiling deletions covering sets of regions in pools.

In certain embodiments, whole genome screens can be used for understanding the phenotypic readout of perturbing potential target genes. In preferred embodiments, perturbations target expressed genes as defined by a gene signature using a focused sgRNA library. Libraries may be focused on expressed genes in specific networks or pathways. In other preferred embodiments, regulatory drivers are perturbed. In certain embodiments, Applicants perform systematic perturbation of key genes that regulate T-cell function in a high-throughput fashion. In certain embodiments, Applicants perform systematic perturbation of key genes that regulate cancer cell function in a high-throughput fashion (e.g., immune resistance or metastasis). Applicants can use gene and/or protein expression profiling data to define the target of interest and perform follow-up single-cell and population RNA-seq and/or protein analysis. Not being bound by a theory, this approach will accelerate the development of therapeutics for human disorders, in particular cancer. Not being bound by a theory, this approach will enhance the understanding of the biology of T-cells and tumor immunity, and accelerate the development of therapeutics for human disorders, in particular cancer, as described herein.

In certain embodiments, signature genes may be perturbed in single cells in vivo and gene and/or protein expression analyzed. Not being bound by a theory, networks of genes that are disrupted due to perturbation of a signature gene may be determined in an in vivo context. Understanding the network of genes effected by a perturbation performed in vivo may allow for a gene to be linked to a specific pathway that may be targeted to modulate the signature and treat a disease (e.g., cancer, autoimmune disease). Thus, in certain embodiments, in vivo Perturb-seq is used to discover novel drug targets to allow treatment of patients having a specific gene signature.

In certain embodiments, the spatial location of perturbed genes in cells or tissues is determined. In regards to localizing proteins reference is made to WO2017/044893 "DNA Microscopy" and US provisional application number 62/309,680. In one embodiment, a tissue sample obtained from an in vivo animal model after perturbation is spatially tagged with functionalized barcoded probes, whereby the barcodes indicate the spatial location of the cells in the tissue upon single cell sequencing. Not being bound by a theory, cells may be perturbed in vivo and the cellular location of cells in response to the perturbations may be analyzed.

Example 5

Multiplex Screening of Perturbations in Different Cell Types

In certain embodiments, perturb-seq may be used to screen multiple cell types in a pooled screen. In one embodiment, a pool of barcode labeled cells is produced as in the PRISM method (see, e.g., Yu et al., Nature Biotechnology 34, 419-423 (2016)). A set of perturbation constructs is introduced to the pool of cells. After perturbation, cells are analyzed by single cell sequencing. The sequencing allows identification of the cell type perturbed, the perturbation, and the gene and/or protein expression in the single cells.

REFERENCES

Acosta-Alvear, D., Zhou, Y., Blais, A., Tsikitis, M., Lents, N. H., Arias, C., Lennon, C. J., Kluger, Y. & Dynlacht, B. D. 2007, "XBP1 controls diverse cell type- and condition-specific transcriptional regulatory networks", *Molecular Cell*, vol. 27, no. 1, pp. 53-66.

Adiconis, X., Borges-Rivera, D., Satija, R., DeLuca, D. S., Busby, M. A., Berlin, A. M., Sivachenko, A., Thompson, D. A., Wysoker, A., Fennell, T., Gnirke, A., Pochet, N., Regev, A. & Levin, J. Z. Comparative analysis of RNA sequencing methods for degraded or low-input samples. *Nat Methods*. 10,623-629, doi:10.1038/nmeth.2483 (2013). PMCID:3821180.

Aguirre, A. J., Meyers, R. M., Weir, B. A., Vazquez, F., Zhang, C., Ben-David, U., Cook, A., Ha, G., Harrington, W. F., Doshi, M. B., et al 2016, "Genomic Copy Number Dictates a Gene-Independent Cell Response to CRISPR/Cas9 Targeting", *Cancer Discovery*, vol. 6, no. 8, pp. 914-929.

Altshuler, D., Daly, M. J., and Lander, E. S. (2008). Genetic Mapping in Human Disease. Science (80-.). 322, 881-888.

Amit, I., Garber, M., Chevrier, N., Leite, A. P., Donner, Y., Eisenhaure, T., Guttman, M., Grenier, J. K., Li, W., Zuk, O., et al. (2009). Unbiased Reconstruction of a Mammalian Transcriptional Network Mediating Pathogen Responses. Science (80-.). 326, 257-263.

Anders, C., Niewoehner, O., Duerst, A. & Jinek, M. 2014, "Structural basis of PAM-dependent target DNA recognition by the Cas9 endonuclease", *Nature*, vol. 513, no. 7519, pp. 569-573.

Assarsson, E., Lundberg, M., Holmquist, G., Bjorkesten, J., Thorsen, S. B., Ekman, D., Eriksson, A., Rennel Dickens, E., Ohlsson, S., Edfeldt, G., et al. (2014). Homogenous 96-plex PEA immunoassay exhibiting high sensitivity, specificity, and excellent scalability. PloS one 9, e95192.

Bamshad, M. J., Ng, S. B., Bigham, A. W., Tabor, H. K., Emond, M. J., Nickerson, D. A., and Shendure, J. (2011). Exome sequencing as a tool for Mendelian disease gene discovery. Nat. Rev. Genet. 12, 745-755.

Bandyopadhyay, S., Mehta, M., Kuo, D., Sung, M.-K., Chuang, R., Jaehnig, E. J., Bodenmiller, B., Licon, K., Copeland, W., Shales, M., et al. (2010). Rewiring of Genetic Networks in Response to DNA Damage. Science (80-.). 330, 1385-1389.

Bao, X. R., Ong, S., Goldberger, O., Peng, J., Sharma, R., Thompson, D. A., Vafai, S. B., Cox, A. G., Marutani, E., Ichinose, F., et al 2016, "Mitochondrial dysfunction remodels one-carbon metabolism in human cells", *eLife*, vol. 5.

Bassik, M. C., Kampmann, M., Lebbink, R. J., Wang, S., Hein, M. Y., Poser, I., Weibezahn, J., Horlbeck, M. a, Chen, S., Mann, M., et al. (2013a). A systematic mammalian genetic interaction map reveals pathways underlying ricin susceptibility. Cell 152, 909-922.

Bassik, M. C., Kampmann, M., Lebbink, R. J., Wang, S., Hein, M. Y., Poser, I., Weibezahn, J., Horlbeck, M. A., Chen, S., Mann, M., et al. (2013b). A Systematic Mammalian Genetic Interaction Map Reveals Pathways Underlying Ricin Susceptibility. Cell 152, 909-922.

Beerenwinkel, N., Pachter, L., and Sturmfels, B. (2007). Epistasis and Shapes of Fitness Landscapes. Stat. Sin. 17, 1317-1342.

Bendall, S. C., Simonds, E. F., Qiu, P., Amir el, A. D., Krutzik, P. O., Finck, R., Bruggner, R. V., Melamed, R., Trejo, A., Ornatsky, O. I., et al. (2011). Single-cell mass cytometry of differential immune and drug responses across a human hematopoietic continuum. Science 332, 687-696.

Berger, A. H., Brooks, A. N., Wu, X., Shrestha, Y., Chouinard, C., Piccioni, F., Bagul, M., Kamburov, A., Imielinski, M., Hogstrom, L., et al. (2016). High-throughput Phenotyping of Lung Cancer Somatic Mutations. Cancer Cell 0, 248-249.

Blecher-Gonen, R., Barnett-Itzhaki, Z., Jaitin, D., Amann-Zalcenstein, D., Lara-Astiaso, D. & Amit, I. High-throughput chromatin immunoprecipitation for genome-wide mapping of in vivo protein-DNA interactions and epigenomic states. Nat Protoc. 8, 539-554, doi:10.1038/nprot.2013.023 (2013).

Bochkis, I. M., Przybylski, D., Chen, J. & Regev, A. Changes in nucleosome occupancy associated with metabolic alterations in aged mammalian liver. Cell reports. 9, 996-1006, doi:10.1016/j.celrep.2014.09.048 (2014). PMCID:4250828.

Boone, C., Bussey, H., and Andrews, B. J. (2007). Exploring genetic interactions and networks with yeast. 8, 437-449.

Bornstein, C., Winter, D., Barnett-Itzhaki, Z., David, E., Kadri, S., Garber, M. & Amit, I. A negative feedback loop of transcription factors specifies alternative dendritic cell chromatin States. Mol Cell. 56, 749-762, doi:10.1016/j.molcel.2014.10.014 (2014). PMCID:4412443.

Botstein, D., and Risch, N. (2003). Discovering genotypes underlying human phenotypes: past successes for mendelian disease, future approaches for complex disease. Nat. Genet. 33, 228-237.

Briner, A. E., Donohoue, P. D., Gomaa, A. A., Selle, K., Slorach, E. M., Nye, C. H., Haurwitz, R. E., Beisel, C. L., May, A. P. & Barrangou, R. 2014, "Guide RNA functional modules direct Cas9 activity and orthogonality", Molecular Cell, vol. 56, no. 2, pp. 333-339.

Buettner, F., Natarajan, K. N., Casale, F. P., Proserpio, V., Scialdone, A., Theis, F. J., Teichmann, S. A., Marioni, J. C., and Stegle, O. (2015). Computational analysis of cell-to-cell heterogeneity in single-cell RNA-sequencing data reveals hidden subpopulations of cells. Nat. Biotechnol. 33, 155-160.

Cabili, M. N., Dunagin, M. C., McClanahan, P. D., Biaesch, A., Padovan-Merhar, O., Regev, A., Rinn, J. L. & Raj, A. Localization and abundance analysis of human lncRNAs at single-cell and single-molecule resolution. Genome Biol. 16, 20, doi:10.1186/s13059-015-0586-4 (2015). PMCID:4369099.

Cabili, M. N., Trapnell, C., Goff, L., Koziol, M., Tazon-Vega, B., Regev, A. & Rinn, J. L. Integrative annotation of human large intergenic noncoding RNAs reveals global properties and specific subclasses. Genes Dev. 25, 1915-1927, doi:10.1101/gad.17446611 (2011). PMCID: 3185964.

Calfon, M., Zeng, H., Urano, F., Till, J. H., Hubbard, S. R., Harding, H. P., Clark, S. G. & Ron, D. 2002, "IRE1 couples endoplasmic reticulum load to secretory capacity by processing the XBP-1 mRNA", Nature, vol. 415, no. 6867, pp. 92-96.

Candès, E. J., and Recht, B. (2009). Exact Matrix Completion via Convex Optimization. Found. Comput. Math. 9, 717-772.

Candès, E. J., Li, X., Ma, Y. & Wright, J. 2011, "Robust principal component analysis?", Journal of the ACM (JACM), vol. 58, no. 3, pp. 11.

Capaldi, A. P., Kaplan, T., Liu, Y., Habib, N., Regev, A., Friedman, N., and O'Shea, E. K. (2008). Structure and function of a transcriptional network activated by the MAPK Hog1. Nat. Genet. 40, 1300-1306.

Carter, G. W., Prinz, S., Neou, C., Shelby, J. P., Marzolf, B., Thorsson, V., and Galitski, T. (2007). Prediction of phenotype and gene expression for combinations of mutations. Mol. Syst. Biol. 3, 96.

Carbon, S., Ireland, A., Mungall, C. J., Shu, S., Marshall, B. & Lewis, S. 2009, "AmiGO: online access to ontology and annotation data", Bioinformatics (Oxford, England), vol. 25, no. 2, pp. 288-289.

Cartwright, T., Perkins, N. D., and L Wilson, C. (2016). NFKB1: a suppressor of inflammation, ageing and cancer. FEBS J. 283, 1812-1822.

Chan, M. M., Smith, Z. D., Egli, D., Regev, A. & Meissner, A. Mouse ooplasm confers context-specific reprogramming capacity. Nature genetics. 44, 978-980, doi: 10.1038/ng.2382 (2012). PMCID:3432711.

Chavez, A., Scheiman, J., Vora, S., Pruitt, B. W., Tuttle, M., P R Iyer, E., Lin, S., Kiani, S., Guzman, C. D., Wiegand, D. J., et al 2015, "Highly efficient Cas9-mediated transcriptional programming", Nature Methods, vol. 12, no. 4, pp. 326-328.

Chen, Y., Liu, P., Nielsen, A. A. K., Brophy, J. A. N., Clancy, K., Peterson, T. & Voigt, C. A. 2013, "Characterization of 582 natural and synthetic terminators and quantification of their design constraints", Nature Methods, vol. 10, no. 7, pp. 659-664.

Chen, S., Sanjana, N. E., Zheng, K., Shalem, O., Lee, K., Shi, X., Scott, D. A., Song, J., Pan, J. Q., Weissleder, R., et al. (2015). Genome-wide CRISPR Screen in a Mouse Model of Tumor Growth and Metastasis. Cell 160, 1246-1260.

Cheng, C. S., Rai, K., Garber, M., Hollinger, A., Robbins, D., Anderson, S., Macbeth, A., Tzou, A., Carneiro, M. O., Raychowdhury, R., Russ, C., Hacohen, N., Gershenwald, J. E., Lennon, N., Nusbaum, C., Chin, L., Regev, A. & Amit, I. Semiconductor-based DNA sequencing of histone modification states. Nat Commun. 4, 2672, doi: 10.1038/ncomms3672 (2013). PMCID:3917140.

Chevrier, N., Mertins, P., Artyomov, M. N., Shalek, A. K., Iannacone, M., Ciaccio, M. F., Gat-Viks, I., Tonti, E., DeGrace, M. M., Clauser, K. R., Garber, M., Eisenhaure, T. M., Yosef, N., Robinson, J., Sutton, A., Andersen, M. S., Root, D. E., von Andrian, U., Jones, R. B., Park, H., Carr, S. A., Regev, A., Amit, I. & Hacohen, N. Systematic discovery of TLR signaling components delineates viral-sensing circuits. Cell. 147, 853-867, doi:10.1016/j.cell.2011.10.022 (2011). PMCID:3809888.

Chuang, C., Lee, K., Fan, C. & Su, Y. 2009, "Porcine type III RNA polymerase III promoters for short hairpin RNA expression", Animal Biotechnology, vol. 20, no. 1, pp. 34-39.

Chung, K., Wallace, J., Kim, S. Y., Kalyanasundaram, S., Andalman, A. S., Davidson, T. J., Mirzabekov, J. J., Zalocusky, K. A., Mattis, J., Denisin, A. K., et al. (2013). Structural and molecular interrogation of intact biological systems. Nature 497, 332-337.

Chung, N. C., and Storey, J. D. (2015). Statistical significance of variables driving systematic variation in high-dimensional data. Bioinformatics 31, 545-554.

Cohen, A., and Sheva, B.- (1998). HIDDEN MARKOV MODELS IN BIOMEDICAL SIGNAL PROCESSING. 20, 1145-1150.

Cong, L., Ran, F. A., Cox, D., Lin, S., Barretto, R., Habib, N., Hsu, P. D., Wu, X., Jiang, W., Marraffini, L. a, et al. (2013). Multiplex genome engineering using CRISPR/Cas systems. Science 339, 819-823.

Costanzo, M., Baryshnikova, A., Bellay, J., Kim, Y., Spear, E. D., Sevier, C. S., Ding, H., Koh, J. L. Y., Toufighi, K., Mostafavi, S., et al. (2010). The Genetic Landscape of a Cell. Science (80-.). 327, 425-431.

Dang, Y., Jia, G., Choi, J., Ma, H., Anaya, E., Ye, C., Shankar, P. & Wu, H. 2015, "Optimizing sgRNA structure to improve CRISPR-Cas9 knockout efficiency", Genome Biology, vol. 16, pp. 280.

Duan, Q., Flynn, C., Niepel, M., Hafner, M., Muhlich, J. L., Fernandez, N. F., Rouillard, A. D., Tan, C. M., Chen, E. Y., Golub, T. R., et al. (2014). LINCS Canvas Browser: interactive web app to query, browse and interrogate LINCS L1000 gene expression signatures. Nucleic Acids Res. 42, W449-W460.

Elsharkawy, A. M., Oakley, F., Lin, F., Packham, G., Mann, D. A., and Mann, J. (2010). The NF-kappaB p50:p50: HDAC-1 repressor complex orchestrates transcriptional inhibition of multiple pro-inflammatory genes. J. Hepatol. 53, 519-527.

Engreitz, J. M., Pandya-Jones, A., McDonel, P., Shishkin, A., Sirokman, K., Surka, C., Kadri, S., Xing, J., Goren, A., Lander, E. S., Plath, K. & Guttman, M. The Xist lncRNA exploits three-dimensional genome architecture to spread across the X chromosome. Science. 341, 1237973, doi: 10.1126/science.1237973 (2013). PMCID:3778663.

Fan, H. C., Fu, G. K., and Fodor, S. P. a. (2015). Combinatorial labeling of single cells for gene expression cytometry. Science. 347, 1258367-1258367.

Fogli, A. & Boespflug-Tanguy, O. 2006, "The large spectrum of eIF2B-related diseases", Biochemical Society Transactions, vol. 34, no. Pt 1, pp. 22-29.

Friedman, J., Hastie, T. & Tibshirani, R. 2001, The elements of statistical learning, Springer series in statistics Springer, Berlin.

Galonska, C., Smith, Z. D. & Meissner, A. In Vivo and in vitro dynamics of undifferentiated embryonic cell transcription factor 1. Stem Cell Reports. 2, 245-252, doi: 10.1016/j.stemcr.2014.01.007 (2014). PMCID:3964277.

Garber, M., Yosef, N., Goren, A., Raychowdhury, R., Thielke, A., Guttman, M., Robinson, J., Minie, B., Chevrier, N., Itzhaki, Z., et al. (2012). A High-Throughput Chromatin Immunoprecipitation Approach Reveals Principles of Dynamic Gene Regulation in Mammals. Mol. Cell 47, 810-822.

Gat-Viks, I., Chevrier, N., Wilentzik, R., Eisenhaure, T., Raychowdhury, R., Steuerman, Y., Shalek, A. K., Hacohen, N., Amit, I. & Regev, A. Deciphering molecular circuits from genetic variation underlying transcriptional responsiveness to stimuli. Nature biotechnology. 31, 342-349, doi:10.1038/nbt.2519 (2013). PMCID:3622156.

Gilbert, L. A., Horlbeck, M. A., Adamson, B., Villalta, J. E., Chen, Y., Whitehead, E. H., Guimaraes, C., Panning, B., Ploegh, H. L., Bassik, M. C., et al. (2014). Genome-Scale CRISPR-Mediated Control of Gene Repression and Activation. Cell 159, 647-661.

Gilbert, L. a, Larson, M. H., Morsut, L., Liu, Z., Brar, G. a, Torres, S. E., Stern-Ginossar, N., Brandman, O., Whitehead, E. H., Doudna, J. a, et al. (2013). CRISPR-mediated modular RNA-guided regulation of transcription in eukaryotes. Cell 154, 442-451.

Gomez, D., Shankman, L. S., Nguyen, A. T., and Owens, G. K. (2013). Detection of histone modifications at specific gene loci in single cells in histological sections. Nature methods 10, 171-177.

Goodwin, E. C. & Rottman, F. M. 1992, "The 3'-flanking sequence of the bovine growth hormone gene contains novel elements required for efficient and accurate polyadenylation", The Journal of Biological Chemistry, vol. 267, no. 23, pp. 16330-16334.

Grun, D. & van Oudenaarden, A. 2015, "Design and Analysis of Single-Cell Sequencing Experiments", Cell, vol. 163, no. 4, pp. 799-810.

Gu, W., Crawford, E. D., O'Donovan, B. D., Wilson, M. R., Chow, E. D., Retallack, H. & DeRisi, J. L. 2016, "Depletion of Abundant Sequences by Hybridization (DASH): using Cas9 to remove unwanted high-abundance species in sequencing libraries and molecular counting applications", Genome Biology, vol. 17, pp. 41.

Guttman, M., Donaghey, J., Carey, B. W., Garber, M., Grenier, J. K., Munson, G., Young, G., Lucas, A. B., Ach, R., Bruhn, L., Yang, X., Amit, I., Meissner, A., Regev, A., Rinn, J. L., Root, D. E. & Lander, E. S. lincRNAs act in the circuitry controlling pluripotency and differentiation. Nature. 477, 295-300, doi:10.1038/nature10398 (2011). PMCID:3175327.

Haas, B. J., Papanicolaou, A., Yassour, M., Grabherr, M., Blood, P. D., Bowden, J., Couger, M. B., Eccles, D., Li, B., Lieber, M., Macmanes, M. D., Ott, M., Orvis, J., Pochet, N., Strozzi, F., Weeks, N., Westerman, R., William, T., Dewey, C. N., Henschel, R., Leduc, R. D., Friedman, N. & Regev, A. De novo transcript sequence reconstruction from RNA-seq using the Trinity platform for reference generation and analysis. Nat Protoc. 8, 1494-1512, doi:10.1038/nprot.2013.084 (2013). PMCID: 3875132.

Haber, J. E., Braberg, H., Wu, Q., Alexander, R., Haase, J., Ryan, C., Lipkin-Moore, Z., Franks-Skiba, K. E., Johnson, T., Shales, M., et al. (2013). Systematic triple-mutant analysis uncovers functional connectivity between pathways involved in chromosome regulation. Cell Rep. 3, 2168-2178.

Hacisuleyman, E., Goff, L. A., Trapnell, C., Williams, A., Henao-Mejia, J., Sun, L., McClanahan, P., Hendrickson, D. G., Sauvageau, M., Kelley, D. R., Morse, M., Engreitz, J., Lander, E. S., Guttman, M., Lodish, H. F., Flavell, R., Raj, A. & Rinn, J. L. Topological organization of multi-chromosomal regions by the long intergenic noncoding RNA Firre. Nat Struct Mol Biol. 21, 198-206, doi: 10.1038/nsmb.2764 (2014). PMCID:3950333.

Haldimann, A. & Wanner, B. L. 2001, "Conditional-replication, integration, excision, and retrieval plasmid-host systems for gene structure-function studies of bacteria", Journal of Bacteriology, vol. 183, no. 21, pp. 6384-6393.

Hamanaka, R. B., Bennett, B. S., Cullinan, S. B. & Diehl, J. A. 2005, "PERK and GCN2 Contribute to eIF2α Phosphorylation and Cell Cycle Arrest after Activation of the Unfolded Protein Response Pathway", Molecular Biology of the Cell, vol. 16, no. 12, pp. 5493-5501.

Han, J., Back, S. H., Hur, J., Lin, Y., Gildersleeve, R., Shan, J., Yuan, C. L., Krokowski, D., Wang, S., Hatzoglou, M., et al 2013, "ER-stress-induced transcriptional regulation increases protein synthesis leading to cell death", Nature Cell Biology, vol. 15, no. 5, pp. 481-490.

Hartl, D. L. (2014). What can Applicants learn from fitness landscapes? Curr. Opin. Microbiol. 21, 51-57.

Heckl, D., Kowalczyk, M. S., Yudovich, D., Belizaire, R., Puram, R. V., McConkey, M. E., Thielke, A., Aster, J. C., Regev, A. & Ebert, B. L. Generation of mouse models of myeloid malignancy with combinatorial genetic lesions using CRISPR-Cas9 genome editing. *Nature biotechnology.* 32,941-946, doi:10.1038/nbt.2951 (2014). PMCID: 4160386.

Heimberg, G., Bhatnagar, R., El-Samad, H., and Thomson, M. (2016). Low Dimensionality in Gene Expression Data Enables the Accurate Extraction of Transcriptional Programs from Shallow Sequencing. Cell Syst. 2, 239-250.

Helft, J., Böttcher, J., Chakravarty, P., Zelenay, S., Huotari, J., Schraml, B. U., Goubau, D., and Reis e Sousa, C. (2015). GM-CSF Mouse Bone Marrow Cultures Comprise a Heterogeneous Population of CD11c+MHCII+ Macrophages and Dendritic Cells. Immunity 42, 1197-1211.

Hetz, C. 2012, "The unfolded protein response: controlling cell fate decisions under ER stress and beyond", *Nature Reviews. Molecular Cell Biology*, vol. 13, no. 2, pp. 89-102.

Horlbeck, M. A., Gilbert, L. A., Villalta, J. E., Adamson, B., Pak, R. A., Chen, Y., Fields, A. P., Park, C. Y., Corn, J. E. & Kampmann, M. 2016, "Compact and highly active next-generation libraries for CRISPR-mediated gene repression and activation", *eLife*, vol. 5, pp. e19760.

Hu, S., Ni, W., Hazi, W., Zhang, H., Zhang, N., Meng, R. & Chen, C. 2011, "Cloning and functional analysis of sheep U6 promoters", *Animal Biotechnology*, vol. 22, no. 3, pp. 170-174.

Huang, D. W., Sherman, B. T. & Lempicki, R. A. 2009a, "Bioinformatics enrichment tools: paths toward the comprehensive functional analysis of large gene lists", *Nucleic Acids Research*, vol. 37, no. 1, pp. 1-13.

Huang, D. W., Sherman, B. T. & Lempicki, R. A. 2009b, "Systematic and integrative analysis of large gene lists using DAVID bioinformatics resources", *Nature Protocols*, vol. 4, no. 1, pp. 44-57.

Hughes, T. R., Marton, M. J., Jones, A. R., Roberts, C. J., Stoughton, R., Armour, C. D., Bennett, H. a, Coffey, E., Dai, H., He, Y. D., et al. (2000). Functional Discovery via a Compendium of Expression Profiles. Cell 102, 109-126.

Jaitin, D. A., Kenigsberg, E., Keren-Shaul, H., Elefant, N., Paul, F., Zaretsky, I., Mildner, A., Cohen, N., Jung, S., Tanay, A. & Amit, I. Massively parallel single-cell RNA-seq for marker-free decomposition of tissues into cell types. *Science.* 343, 776-779, doi:10.1126/science.1247651 (2014). PMCID:4412462.

Janssen, K. P., Knez, K., Spasic, D., and Lammertyn, J. (2013). Nucleic acids for ultra-sensitive protein detection. Sensors 13, 1353-1384.

Jiang, F., Zhou, K., Ma, L., Gressel, S. & Doudna, J. A. 2015, "STRUCTURAL BIOLOGY. A Cas9-guide RNA complex preorganized for target DNA recognition", *Science* (New York, N.Y.), vol. 348, no. 6242, pp. 1477-1481.

Jin, F., Hazbun, T., Michaud, G. A., Salcius, M., Predki, P. F., Fields, S., and Huang, J. (2006). A pooling-deconvolution strategy for biological network elucidation. Nat Methods 3, 183-189.

Joensson, H. N., and Andersson Svahn, H. (2012). Droplet Microfluidics-A Tool for Single-Cell Analysis. Angew. Chemie Int. Ed. 51, 12176-12192.

Jonikas, M. C., Collins, S. R., Denic, V., Oh, E., Quan, E. M., Schmid, V., Weibezahn, J., Schwappach, B., Walter, P., Weissman, J. S., et al 2009, "Comprehensive characterization of genes required for protein folding in the endoplasmic reticulum", *Science* (New York, N.Y.), vol. 323, no. 5922, pp. 1693-1697.

Jovanovic, M., Rooney, M. S., Mertins, P., Przybylski, D., Chevrier, N., Satija, R., Rodriguez, E. H., Fields, A. P., Schwartz, S., Raychowdhury, R., Mumbach, M. R., Eisenhaure, T., Rabani, M., Gennert, D., Lu, D., Delorey, T., Weissman, J. S., Carr, S. A., Hacohen, N. & Regev, A. Dynamic profiling of the protein life cycle in response to pathogens. *Science.* 347, 1259038, doi:10.1126/science.1259038 (2015). PMCID:PMC Journal—In Process.

Jovanovic, M., Rooney, M. S., Mertins, P., Przybylski, D., Chevrier, N., Satija, R., Rodriguez, E. H., Fields, A. P., Schwartz, S., Raychowdhury, R., et al. (2015). Dynamic profiling of the protein life cycle in response to pathogens. Science (80-.). 347, 1259038-1259038.

Kabadi, A. M., Ousterout, D. G., Hilton, I. B., and Gersbach, C. A. (2014). Multiplex CRISPR/Cas9-based genome engineering from a single lentiviral vector. Nucleic Acids Res. 42, 1-11.

Kampmann, M., Bassik, M. C., and Weissman, J. S. (2014). Functional genomics platform for pooled screening and generation of mammalian genetic interaction maps. Nat. Protoc. 9, 1825-1847.

Kanda, S., Yanagitani, K., Yokota, Y., Esaki, Y. & Kohno, K. 2016, "Autonomous translational pausing is required for XBP1u mRNA recruitment to the ER via the SRP pathway", *Proceedings of the National Academy of Sciences of the United States of America*, vol. 113, no. 40, pp. E5895.

Kantlehner, M., Kirchner, R., Hartmann, P., Ellwart, J. W., Alunni-Fabbroni, M., and Schumacher, A. (2011). A high-throughput DNA methylation analysis of a single cell. Nucleic acids research 39, e44.

Kearns, N. A., Genga, R. M., Enuameh, M. S., Garber, M., Wolfe, S. A. & Maehr, R. Cas9 effector-mediated regulation of transcription and differentiation in human pluripotent stem cells. *Development.* 141,219-223, doi: 10.1242/dev.103341 (2014). PMCID:3865759.

Kelley, D. & Rinn, J. Transposable elements reveal a stem cell-specific class of long noncoding RNAs. *Genome Biol.* 13, R107, doi:10.1186/gb-2012-13-11-r107 (2012). PMCID:3580499.

Kemmeren, P., Sameith, K., Van De Pasch, L. A. L., Benschop, J. J., Lenstra, T. L., Margaritis, T., O'Duibhir, E., Apweiler, E., Van Wageningen, S., Ko, C. W., et al. (2014). Large-scale genetic perturbations reveal regulatory networks and an abundance of gene-specific repressors. Cell 157, 740-752.

Kharchenko, P. V, Silberstein, L., and Scadden, D. T. (2014). Bayesian approach to single-cell differential expression analysis. Nat. Methods 11, 740-742.

Klein, A. M., Mazutis, L., Akartuna, I., Tallapragada, N., Veres, A., Li, V., Peshkin, L., Weitz, D. A., and Kirschner, M. W. (2015). Droplet barcoding for single-cell transcriptomics applied to embryonic stem cells. Cell 161, 1187-1201.

Komor, A. C., Kim, Y. B., Packer, M. S., Zuris, J. A. & Liu, D. R. 2016, "Programmable editing of a target base in genomic DNA without double-stranded DNA cleavage", *Nature*, vol. 533, no. 7603, pp. 420-424.

Konermann, S., Brigham, M. D., Trevino, A. E., Joung, J., Abudayyeh, O. O., Barcena, C., Hsu, P. D., Habib, N., Gootenberg, J. S., Nishimasu, H., et al. (2014). Genome-scale transcriptional activation by an engineered CRISPR-Cas9 complex. Nature 517, 583-588.

Kowalczyk, M. S., Tirosh, I., Heckl, D., Rao, T. N., Dixit, A., Haas, B. J., Schneider, R. K., Wagers, A. J., Ebert, B. L., and Regev, A. (2015). Single-cell RNA-seq reveals changes in cell cycle and differentiation programs upon aging of hematopoietic stem cells. Genome Res. 25, 1860-1872.

Kuleshov, M. V., Jones, M. R., Rouillard, A. D., Fernandez, N. F., Duan, Q., Wang, Z., Koplev, S., Jenkins, S. L., Jagodnik, K. M., Lachmann, A., et al 2016, "Enrichr: a comprehensive gene set enrichment analysis web server 2016 update", Nucleic Acids Research, vol. 44, no. W1, pp. 90.

Kumar, R. M., Cahan, P., Shalek, A. K., Satij a, R., DaleyKeyser, A. J., Li, H., Zhang, J., Pardee, K., Gennert, D., Trombetta, J. J., Ferrante, T. C., Regev, A., Daley, G. Q. & Collins, J. J. Deconstructing transcriptional heterogeneity in pluripotent stem cells. Nature. 516, 56-61, doi:10.1038/nature13920 (2014). PMCID: 4256722.

Labzin, L. I., Schmidt, S. V, Masters, S. L., Beyer, M., Krebs, W., Klee, K., Stahl, R., Lütjohann, D., Schultze, J. L., Latz, E., et al. (2015). ATF3 Is a Key Regulator of Macrophage IFN Responses. J. Immunol. 195, 4446-4455.

Lamb, J., Crawford, E. D., Peck, D., Modell, J. W., Blat, I. C., Wrobel, M. J., Lerner, J., Brunet, J., Subramanian, A., Ross, K. N., et al. (2006). The Connectivity Map: Using. Science (80-.). 313, 1929-1935.

Lambeth, L. S Wise, T. G., Moore, R. J., Muralitharan, M. S. & Doran, T. J. 2006, "Comparison of bovine RNA polymerase III promoters for short hairpin RNA expression", Animal Genetics, vol. 37, no. 4, pp. 369-372.

Lara-Astiaso, D., Weiner, A., Lorenzo-Vivas, E., Zaretsky, I., Jaitin, D. A., David, E., Keren-Shaul, H., Mildner, A., Winter, D., Jung, S., Friedman, N. & Amit, I. Immunogenetics. Chromatin state dynamics during blood formation. Science. 345, 943-949, doi:10.1126/science.1256271 (2014). PMCID:4412442.

Laufer, C., Fischer, B., Billmann, M., Huber, W., and Boutros, M. (2013). Mapping genetic interactions in human cancer cells with RNAi and multiparametric phenotyping. Nat. Methods 10, 427-431.

Lawrence, M. S., Stojanov, P., Mermel, C. H., Robinson, J. T., Garraway, L. A., Golub, T. R., Meyerson, M., Gabriel, S. B., Lander, E. S., and Getz, G. (2014). Discovery and saturation analysis of cancer genes across 21 tumour types. Nature 505, 495-501.

Lee, A., Iwakoshi, N. N. & Glimcher, L. H. 2003, "XBP-1 regulates a subset of endoplasmic reticulum resident chaperone genes in the unfolded protein response", Molecular and Cellular Biology, vol. 23, no. 21, pp. 7448-7459.

Lee, M. N., Ye, C., Villani, A. C., Raj, T., Li, W., Eisenhaure, T. M., Imboywa, S. H., Chipendo, P. I., Ran, F. A., Slowikowski, K., Ward, L. D., Raddassi, K., McCabe, C., Lee, M. H., Frohlich, I. Y., Hafler, D. A., Kellis, M., Raychaudhuri, S., Zhang, F., Stranger, B. E., Benoist, C. O., De Jager, P. L., Regev, A. & Hacohen, N. Common genetic variants modulate pathogen-sensing responses in human dendritic cells. Science. 343,1246980, doi: 10.1126/science.1246980 (2014). PMCID:4124741.

Liang, S., Zhang, W., McGrath, B. C., Zhang, P. & Cavener, D. R. 2006, "PERK (eIF2alpha kinase) is required to activate the stress-activated MAPKs and induce the expression of immediate-early genes upon disruption of ER calcium homoeostasis", The Biochemical Journal, vol. 393, no. Pt 1, pp. 201-209.

Liberali, P., Snijder, B., and Pelkmans, L. (2014). Single-cell and multivariate approaches in genetic perturbation screens. Nat. Rev. Genet. 16, 18-32.

Lin, J. H., Li, H., Yasumura, D., Cohen, H. R., Zhang, C., Panning, B., Shokat, K. M., Lavail, M. M. & Walter, P. 2007, "IRE1 signaling affects cell fate during the unfolded protein response", Science (New York, N.Y.), vol. 318, no. 5852, pp. 944-949.

Lin, Z., Chen, M. & Ma, Y. 2010, "The augmented lagrange multiplier method for exact recovery of corrupted low-rank matrices", arXiv preprint arXiv: 1009.5055.

Lorthongpanich, C., Cheow, L. F., Balu, S., Quake, S. R., Knowles, B. B., Burkholder, W. F., Solter, D., and Messerschmidt, D. M. (2013). Single-cell DNA-methylation analysis reveals epigenetic chimerism in preimplantation embryos. Science 341, 1110-1112.

Lutz, R. & Bujard, H. 1997, "Independent and tight regulation of transcriptional units in Escherichia coli via the LacR/O, the TetR/O and AraC/I1-I2 regulatory elements", Nucleic Acids Research, vol. 25, no. 6, pp. 1203-1210.

Macosko, E. Z., Basu, A., Satija, R., Nemesh, J., Shekhar, K., Goldman, M., Tirosh, I., Bialas, A. R., Kamitaki, N., Martersteck, E. M., et al. (2015). Highly Parallel Genome-wide Expression Profiling of Individual Cells Using Nanoliter Droplets. Cell 161, 1202-1214.

Makarova, K. S., Haft, D. H., Barrangou, R., Brouns, S. J. J., Charpentier, E., Horvath, P., Moineau, S., Mojica, F. J. M., Wolf, Y. I., Yakunin, A. F., et al. (2011). Evolution and Classification of the CRISPR—Cas Systems. Nat. Rev. Microbiol. 9, 467-477.

Manolio, T. A., Collins, F. S., Cox, N. J., Goldstein, D. B., Hindorff, L. A., Hunter, D. J., McCarthy, M. I., Ramos, E. M., Cardon, L. R., Chakravarti, A., et al. (2009). Finding the missing heritability of complex diseases. Nature 461, 747-753.

Martincorena, I., and Campbell, P. J. (2015). Somatic mutation in cancer and normal cells. Science (80-.). 349, 1483-1489.

Meerbrey, K. L., Hu, G., Kessler, J. D., Roarty, K., Li, M. Z., Fang, J. E., Herschkowitz, J. I., Burrows, A. E., Ciccia, A., Sun, T., et al 2011, "The pINDUCER lentiviral toolkit for inducible RNA interference in vitro and in vivo", Proceedings of the National Academy of Sciences of the United States of America, vol. 108, no. 9, pp. 3665-3670.

Meier, J. A., and Larner, A. C. (2014). Toward a new STATe: the role of STATs in mitochondrial function. Semin. Immunol. 26, 20-28.

Melnikov, A., Murugan, A., Zhang, X., Tesileanu, T., Wang, L., Rogov, P., Feizi, S., Gnirke, A., Callan, C. G., Kinney, J. B., et al. (2012). Systematic dissection and optimization of inducible enhancers in human cells using a massively parallel reporter assay. Nat. Biotechnol. 30, 271-277.

Müller-Kuller, U., Ackermann, M., Kolodziej, S., Brendel, C., Fritsch, J., Lachmann, N., Kunkel, H., Lausen, J., Schambach, A., Moritz, T., et al 2015, "A minimal ubiquitous chromatin opening element (UCOE) effectively prevents silencing of juxtaposed heterologous promoters by epigenetic remodeling in multipotent and pluripotent stem cells", Nucleic Acids Research, pp. gkv019.

Munoz, D. M., Cassiani, P. J., Li, L., Billy, E., Korn, J. M., Jones, M. D., Golji, J., Ruddy, D. A., Yu, K., McAllister, G., et al 2016, "CRISPR Screens Provide a Comprehensive Assessment of Cancer Vulnerabilities but Generate False-Positive Hits for Highly Amplified Genomic Regions", Cancer Discovery, vol. 6, no. 8, pp. 900-913.

Na, Y. R., Kim, S. Y., Gaublomme, J. T., Shalek, A. K., Jorgolli, M., Park, H. & Yang, E. G. Probing enzymatic activity inside living cells using a nanowire-cell "sandwich" assay. *Nano Lett.* 13,153-158, doi:10.1021/nl3037068 (2013). PMCID:3541459.

Nagano, T., Lubling, Y., Stevens, T. J., Schoenfelder, S., Yaffe, E., Dean, W., Laue, E. D., Tanay, A., and Fraser, P. (2013). Single-cell Hi-C reveals cell-to-cell variability in chromosome structure. Nature 502, 59-64.

Neumann, B., Walter, T., Hériché, J.-K., Bulkescher, J., Erfle, H., Conrad, C., Rogers, P., Poser, I., Held, M., Liebel, U., et al. (2010). Phenotypic profiling of the human genome by time-lapse microscopy reveals cell division genes. Nature 464, 721-727.

Nishimasu, H., Ran, F. A., Hsu, P. D., Konermann, S., Shehata, S. I., Dohmae, N., Ishitani, R., Zhang, F. & Nureki, 0.2014, "Crystal structure of Cas9 in complex with guide RNA and target DNA", *Cell*, vol. 156, no. 5, pp. 935-949.

Nissim, L., Perli, S. D., Fridkin, A., Perez-Pinera, P. & Lu, T. K. 2014, "Multiplexed and programmable regulation of gene networks with an integrated RNA and CRISPR/Cas toolkit in human cells", *Molecular Cell*, vol. 54, no. 4, pp. 698-710.

Okabe, Y., and Medzhitov, R. (2014). Tissue-Specific Signals Control Reversible Program of Localization and Functional Polarization of Macrophages. Cell 157, 832-844.

Pardon, E., Laeremans, T., Triest, S., Rasmussen, S. G., Wohlkonig, A., Ruf, A., Muyldermans, S., Hol, W. G., Kobilka, B. K., and Steyaert, J. (2014). A general protocol for the generation of Nanobodies for structural biology. Nature protocols 9, 674-693.

Parnas, O., Jovanovic, M., Eisenhaure, T. M., Herbst, R. H., Dixit, A., Ye, C. J., Przybylski, D., Platt, R. J., Tirosh, I., Sanjana, N. E., et al. (2015). A Genome-wide CRISPR Screen in Primary Immune Cells to Dissect Regulatory Networks. Cell 162, 675-686.

Perfetto, S. P., Chattopadhyay, P. K., and Roederer, M. (2004). Seventeen-colour flow cytometry: unravelling the immune system. Nature reviews Immunology 4, 648-655.

Phillips, P. C. (2008). Epistasis—the essential role of gene interactions in the structure and evolution of genetic systems.

Platt, R. J., Chen, S., Zhou, Y., Yim, M. J., Swiech, L., Kempton, H. R., Dahlman, J. E., Parnas, O., Eisenhaure, T. M., Jovanovic, M., et al. (2014). CRISPR-Cas9 Knockin Mice for Genome Editing and Cancer Modeling. Cell 159, 440-455.

Plumb, R., Zhang, Z., Appathurai, S. & Mariappan, M. 2015, "A functional link between the co-translational protein translocation pathway and the UPR", *eLife*, vol. 4.

Pollen, A. A., Nowakowski, T. J., Shuga, J., Wang, X., Leyrat, A. A., Lui, J. H., Li, N., Szpankowski, L., Fowler, B., Chen, P., et al 2014, "Low-coverage single-cell mRNA sequencing reveals cellular heterogeneity and activated signaling pathways in developing cerebral cortex", *Nature Biotechnology*, vol. 32, no. 10, pp. 1053-1058.

Qi, L. S., Larson, M. H., Gilbert, L. A., Doudna, J. A., Weissman, J. S., Arkin, A. P., and Lim, W. A. (2013). Repurposing CRISPR as an RNA-Guided Platform for Sequence-Specific Control of Gene Expression. Cell 152, 1173-1183.

Rabani, M., Raychowdhury, R., Jovanovic, M., Rooney, M., Stumpo, D. J., Pauli, A., Hacohen, N., Schier, A. F., Blackshear, P. J., Friedman, N., Amit, I. & Regev, A. High-resolution sequencing and modeling identifies distinct dynamic RNA regulatory strategies. *Cell.* 159, 1698-1710, doi:10.1016/j.cell.2014.11.015 (2014). PMCID: 4272607.

Rajagopal, N., Srinivasan, S., Kooshesh, K., Guo, Y., Edwards, M. D., Banerjee, B., Syed, T., Emons, B. J. M., Gifford, D. K., and Sherwood, R. I. (2016). High-throughput mapping of regulatory DNA. Nat. Biotechnol. 34, 167-174.

Ramsauer, K., Farlik, M., Zupkovitz, G., Seiser, C., Kröger, A., Hauser, H., and Decker, T. (2007). Distinct modes of action applied by transcription factors STAT1 and IRF1 to initiate transcription of the IFN-gamma-inducible gbp2 gene. Proc. Natl. Acad. Sci. U.S.A. 104, 2849-2854.

Ram, O., Goren, A., Amit, I., Shoresh, N., Yosef, N., Ernst, J., Kellis, M., Gymrek, M., Issner, R., Coyne, M., Durham, T., Zhang, X., Donaghey, J., Epstein, C. B., Regev, A. & Bernstein, B. E. Combinatorial patterning of chromatin regulators uncovered by genome-wide location analysis in human cells. *Cell.* 147, 1628-1639, doi: 10.1016/j.cell.2011.09.057 (2011). PMCID:3312319.

Ran, F. A., Cong, L., Yan, W. X., Scott, D. A., Gootenberg, J. S., Kriz, A. J., Zetsche, B., Shalem, O., Wu, X., Makarova, K. S., et al. (2015). In vivo genome editing using *Staphylococcus aureus* Cas9. Nature 520, 186-191.

Ron, D. & Walter, P. 2007, "Signal integration in the endoplasmic reticulum unfolded protein response", *Nature Reviews. Molecular Cell Biology*, vol. 8, no. 7, pp. 519-529.

Rosvall, M., and Bergstrom, C. T. (2008). Maps of random walks on complex networks reveal community structure. Proc. Natl. Acad. Sci. 105, 1118-1123.

Sack, L. M., Davoli, T., Xu, Q., Li, M. Z. & Elledge, S. J. 2016, "Sources of Error in Mammalian Genetic Screens", G3 (Bethesda, Md.), vol. 6, no. 9, pp. 2781-2790.

Sackton, T. B., and Hartl, D. L. (2016). Perspective Genotypic Context and Epistasis in Individuals and Populations. Cell 166, 279-287.

Satija, R., Farrell, J. A., Gennert, D., Schier, A. F. & Regev, A. Spatial reconstruction of single-cell gene expression data. *Nature biotechnology.* 33, 495-502, doi:10.1038/nbt.3192 (2015).

Sauvageau, M., Goff, L. A., Lodato, S., Bonev, B., Groff, A. F., Gerhardinger, C., Sanchez-Gomez, D. B., Hacisuleyman, E., Li, E., Spence, M., Liapis, S. C., Mallard, W., Morse, M., Swerdel, M. R., D'Ecclessis, M. F., Moore, J. C., Lai, V., Gong, G., Yancopoulos, G. D., Frendewey, D., Kellis, M., Hart, R. P., Valenzuela, D. M., Arlotta, P. & Rinn, J. L. Multiple knockout mouse models reveal lincRNAs are required for life and brain development. *eLife.* 2, e01749, doi:10.7554/eLife.01749 (2013). PMCID: 3874104.

Sawyers, C. (2004). Targeted cancer therapy. Nature 432, 294-297.

Schölkopf, B., Platt, J. C., Shawe-Taylor, J., Smola, A. J. & Williamson, R. C. 2001, "Estimating the support of a high-dimensional distribution", *Neural computation*, vol. 13, no. 7, pp. 1443-1471.

Schwartz, S., Agarwala, S. D., Mumbach, M. R., Jovanovic, M., Mertins, P., Shishkin, A., Tabach, Y., Mikkelsen, T. S., Satija, R., Ruvkun, G., Carr, S. A., Lander, E. S., Fink, G. R. & Regev, A. High-resolution mapping reveals a conserved, widespread, dynamic mRNA methylation program in yeast meiosis. *Cell.* 155, 1409-1421, doi:10.1016/j.cell.2013.10.047 (2013). PMCID:3956118.

Schwartz, S., Bernstein, D. A., Mumbach, M. R., Jovanovic, M., Herbst, R. H., Leon-Ricardo, B. X., Engreitz, J. M., Guttman, M., Satija, R., Lander, E. S., Fink, G. & Regev, A. Transcriptome-wide mapping reveals widespread dynamic-regulated pseudouridylation of ncRNA and mRNA. Cell. 159, 148-162, doi:10.1016/j.cell.2014.08.028 (2014). PMCID:4180118.

Schwartz, S., Mumbach, M. R., Jovanovic, M., Wang, T., Maciag, K., Bushkin, G. G., Mertins, P., Ter-Ovanesyan, D., Habib, N., Cacchiarelli, D., Sanjana, N. E., Freinkman, E., Pacold, M. E., Satija, R., Mikkelsen, T. S., Hacohen, N., Zhang, F., Carr, S. A., Lander, E. S. & Regev, A. Perturbation of m6A writers reveals two distinct classes of mRNA methylation at internal and 5' sites. Cell reports. 8, 284-296, doi:10.1016/j.celrep.2014.05.048 (2014). PMCID:4142486.

Shahni, R., Cale, C. M., Anderson, G., Osellame, L. D., Hambleton, S., Jacques, T. S., Wedatilake, Y., Taanman, J.-W., Chan, E., Qasim, W., et al. (2015). Signal transducer and activator of transcription 2 deficiency is a novel disorder of mitochondrial fission. Brain 138, 2834-2846.

Shakya, A., Callister, C., Goren, A., Yosef, N., Garg, N., Khoddami, V., Nix, D., Regev, A. & Tantin, D. Pluripotency transcription factor Oct4 mediates stepwise nucleosome demethylation and depletion. Mol Cell Biol. 35, 1014-1025, doi:10.1128/MCB.01105-14 (2015). PMCID: 4333097.

Shalek, A. K., Gaublomme, J. T., Wang, L., Yosef, N., Chevrier, N., Andersen, M. S., Robinson, J. T., Pochet, N., Neuberg, D., Gertner, R. S., Amit, I., Brown, J. R., Hacohen, N., Regev, A., Wu, C. J. & Park, H. Nanowire-mediated delivery enables functional interrogation of primary immune cells: application to the analysis of chronic lymphocytic leukemia. Nano Lett. 12, 6498-6504, doi: 10.1021/nl3042917 (2012). PMCID:3573729.

Shalek, A. K., Satija, R., Adiconis, X., Gertner, R. S., Gaublomme, J. T., Raychowdhury, R., Schwartz, S., Yosef, N., Malboeuf, C., Lu, D., et al. (2013). Single-cell transcriptomics reveals bimodality in expression and splicing in immune cells. Nature 498, 236-240.

Shalek, A. K., Satija, R., Shuga, J., Trombetta, J. J., Gennert, D., Lu, D., Chen, P., Gertner, R. S., Gaublomme, J. T., Yosef, N., et al. (2014). Single-cell RNA-seq reveals dynamic paracrine control of cellular variation. Nature 510, 363-369.

Shalem, O., Sanjana, N. E., Hartenian, E., Shi, X., Scott, D. A., Mikkelsen, T. S., Heckl, D., Ebert, B. L., Root, D. E., Doench, J. G., et al. (2014). Genome-scale CRISPR-Cas9 knockout screening in human cells. Science 343, 84-87.

Shalem, O., Sanjana, N. E. & Zhang, F. 2015, "High-throughput functional genomics using CRISPR-Cas9", Nature Reviews Genetics, vol. 16, no. 5, pp. 299-311.

Shao, H., Burrage, L. C., Sinasac, D. S., Hill, A. E., Ernest, S. R., O'Brien, W., Courtland, H.-W., Jepsen, K. J., Kirby, A., Kulbokas, E. J., et al. (2008). Genetic architecture of complex traits: large phenotypic effects and pervasive epistasis. Proc. Natl. Acad. Sci. U.S.A. 105, 19910-19914.

Shendure, J., and Akey, J. M. (2015). The origins, determinants, and consequences of human mutations. Science (80-.). 349, 1478-1483.

Shendure, J., and Fields, S. (2016). Massively Parallel Genetics. Genetics 203, 617-619.

Shi, J., Wang, E., Milazzo, J. P., Wang, Z., Kinney, J. B. & Vakoc, C. R. 2015, "Discovery of cancer drug targets by CRISPR-Cas9 screening of protein domains", Nature biotechnology, vol. 33, no. 6, pp. 661-667.

Shoulders, M. D., Ryno, L. M., Genereux, J. C., Moresco, J. J., Tu, P. G., Wu, C., Yates, J. R., Su, A. I., Kelly, J. W. & Wiseman, R. L. 2013, "Stress-independent activation of XBP1s and/or ATF6 reveals three functionally diverse ER proteostasis environments", Cell Reports, vol. 3, no. 4, pp. 1279-1292.

Sidrauski, C., Tsai, J. C., Kampmann, M., Hearn, B. R., Vedantham, P., Jaishankar, P., Sokabe, M., Mendez, A. S., Newton, B. W., Tang, E. L., et al 2015, "Pharmacological dimerization and activation of the exchange factor eIF2B antagonizes the integrated stress response", eLife, vol. 4, pp. e07314.

Sisler, J. D., Morgan, M., Raj e, V., Grande, R. C., Derecka, M., Meier, J., Cantwell, M., Szczepanek, K., Korzun, W. J., Lesnefsky, E. J., et al. (2015). The Signal Transducer and Activator of Transcription 1 (STAT1) Inhibits Mitochondrial Biogenesis in Liver and Fatty Acid Oxidation in Adipocytes. PLoS One 10, e0144444.

Smith, R. P., Taher, L., Patwardhan, R. P., Kim, M. J., Inoue, F., Shendure, J., Ovcharenko, I., and Ahituv, N. (2013). Massively parallel decoding of mammalian regulatory sequences supports a flexible organizational model. Nat. Genet. 45, 1021-1028.

Smith, Z. D., Chan, M. M., Humm, K. C., Karnik, R., Mekhoubad, S., Regev, A., Eggan, K. & Meissner, A. DNA methylation dynamics of the human preimplantation embryo. Nature. 511, 611-615, doi:10.1038/nature13581 (2014). PMCID:4178976.

Smith, Z. D., Chan, M. M., Mikkelsen, T. S., Gu, H., Gnirke, A., Regev, A. & Meissner, A. A unique regulatory phase of DNA methylation in the early mammalian embryo. Nature. 484, 339-344, doi: 10. 1038/nature10960 (2012). PMCID:3331945.

Smyth, R. P., Davenport, M. P. & Mak, J. 2012, "The origin of genetic diversity in HIV-1", Virus Research, vol. 169, no. 2, pp. 415-429.

Snijder, B., Sacher, R., Ramo, P., Damm, E., Liberali, P. & Pelkmans, L. 2009, "Population context determines cell-to-cell variability in endocytosis and virus infection", Nature, vol. 461, no. 7263, pp. 520-523.

Sokolov, A., Carlin, D. E., Paull, E. O., Baertsch, R., and Stuart, J. M. (2016). Pathway-Based Genomics Prediction using Generalized Elastic Net. PLOS Comput. Biol. 12, e1004790.

Stegle, O., Teichmann, S. A., and Marioni, J. C. (2015). Computational and analytical challenges in single-cell transcriptomics. Nat. Rev. Genet. 16, 133-145.

Sun, L., Goff, L. A., Trapnell, C., Alexander, R., Lo, K. A., Hacisuleyman, E., Sauvageau, M., Tazon-Vega, B., Kelley, D. R., Hendrickson, D. G., Yuan, B., Kellis, M., Lodish, H. F. & Rinn, J. L. Long noncoding RNAs regulate adipogenesis. Proceedings of the National Academy of Sciences of the United States of America. 110, 3387-3392, doi:10.1073/pnas.1222643110 (2013). PMCID:3587215.

Tanenbaum, M. E., Gilbert, L. A., Qi, L. S., Weissman, J. S. & Vale, R. D. 2014, "A protein-tagging system for signal amplification in gene expression and fluorescence imaging", Cell, vol. 159, no. 3, pp. 635-646.

Tang, H., Klopfenstein, D., Pedersen, B., Flick, P., Sato, K., Ramirez, F., Yunes, J., and Mungall, C. (2015). GOATOOLS: Tools for Gene Ontology.

Theile, C. S., Witte, M. D., Blom, A. E., Kundrat, L., Ploegh, H. L., and Guimaraes, C. P. (2013). Site-specific N-terminal labeling of proteins using sortase-mediated reactions. Nature protocols 8, 1800-1807.

Thomason, L. C., Costantino, N. & Court, D. L. 2007, "E. coli genome manipulation by P1 transduction", Current Protocols in Molecular Biology, vol. Chapter 1, pp. Unit 1.17.

Thomason, L. C., Sawitzke, J. A., Li, X., Costantino, N. & Court, D. L. 2014, "Recombineering: genetic engineering in bacteria using homologous recombination", *Current Protocols in Molecular Biology*, vol. 106, pp. 39.

Tong, A. H. Y. (2004). Global Mapping of the Yeast Genetic Interaction Network. Science (80-.). 303, 808-813.

Trapnell, C. 2015, "Defining cell types and states with single-cell genomics", *Genome Research*, vol. 25, no. 10, pp. 1491-1498.

Trapnell, C., Cacchiarelli, D., Grimsby, J., Pokharel, P., Li, S., Morse, M., Lennon, N. J., Livak, K. J., Mikkelsen, T. S. & Rinn, J. L. The dynamics and regulators of cell fate decisions are revealed by pseudotemporal ordering of single cells. *Nature biotechnology.* 32, 381-386, doi:10.1038/nbt.2859 (2014). PMCID:4122333.

Trapnell, C., Hendrickson, D. G., Sauvageau, M., Goff, L., Rinn, J. L. & Pachter, L. Differential analysis of gene regulation at transcript resolution with RNA-seq. *Nature biotechnology.* 31, 46-53, doi:10.1038/nbt.2450 (2013). PMCID:3869392.

Trombetta, J. J., Gennert, D., Lu, D., Satija, R., Shalek, A. K. & Regev, A. Preparation of Single-Cell RNA-Seq Libraries for Next Generation Sequencing. *Curr Protoc Mol Biol.* 107, 4 22 21-24 22 17, doi:10.1002/0471142727.mb0422s107 (2014). PMCID:4338574.

Tsumura, A., Hayakawa, T., Kumaki, Y., Takebayashi, S., Sakaue, M., Matsuoka, C., Shimotohno, K., Ishikawa, F., Li, E., Ueda, H. R., et al. (2006). Maintenance of self-renewal ability of mouse embryonic stem cells in the absence of DNA methyltransferases Dnmt1, Dnmt3a and Dnmt3b. Genes to Cells 11, 805-814.

Tussiwand, R., Lee, W.-L., Murphy, T. L., Mashayekhi, M., K C, W., Albring, J. C., Satpathy, A. T., Rotondo, J. A., Edelson, B. T., Kretzer, N. M., et al. (2012). Compensatory dendritic cell development mediated by BATF-IRF interactions. Nature 490, 502-507.

Tyynismaa, H., Carroll, C. J., Raimundo, N., Ahola-Erkkilä, S., Wenz, T., Ruhanen, H., Guse, K., Hemminki, A., Peltola-Mjosund, K. E., Tulkki, V., et al 2010, "Mitochondrial myopathy induces a starvation-like response", *Human Molecular Genetics*, vol. 19, no. 20, pp. 3948-3958.

Van Der Maaten, L. 2014, "Accelerating t-SNE using tree-based algorithms.", *Journal of machine learning research*, vol. 15, no. 1, pp. 3221-3245.

Visscher, P. M., Brown, M. A., McCarthy, M. I., and Yang, J. (2012). Five Years of GWAS Discovery. Am. J. Hum. Genet. 90, 7-24.

Walter, P. & Ron, D. 2011, "The unfolded protein response: from stress pathway to homeostatic regulation", *Science (New York, N.Y.)*, vol. 334, no. 6059, pp. 1081-1086.

Wang, L., Shalek, A. K., Lawrence, M., Ding, R., Gaublomme, J. T., Pochet, N., Stojanov, P., Sougnez, C., Shukla, S. A., Stevenson, K. E., Zhang, W., Wong, J., Sievers, Q. L., MacDonald, B. T., Vartanov, A. R., Goldstein, N. R., Neuberg, D., He, X., Lander, E., Hacohen, N., Regev, A., Getz, G., Brown, J. R., Park, H. & Wu, C. J. Somatic mutation as a mechanism of Wnt/beta-catenin pathway activation in CLL. *Blood.* 124, 1089-1098, doi: 10.1182/blood-2014-01-552067 (2014). PMCID: 4133483.

Wang, T., Wei, J. J., Sabatini, D. M., and Lander, E. S. (2014). Genetic screens in human cells using the CRISPR-Cas9 system. Science 343, 80-84.

Wang, T., Birsoy, K., Hughes, N. W., Krupczak, K. M., Post, Y., Wei, J. J., Lander, E. S., and Sabatini, D. M. (2015). Identification and characterization of essential genes in the human genome. Science (80-.). 350, 1096-1101.

Wang, Y., Shen, J., Arenzana, N., Tirasophon, W., Kaufman, R. J. & Prywes, R. 2000, "Activation of ATF6 and an ATF6 DNA binding site by the endoplasmic reticulum stress response", *The Journal of Biological Chemistry*, vol. 275, no. 35, pp. 27013-27020.

Wei, L., Fan, M., Xu, L., Heinrich, K., Berry, M. W., Homayouni, R., and Pfeffer, L. M. (2008). Bioinformatic analysis reveals cRel as a regulator of a subset of interferon-stimulated genes. J. Interferon Cytokine Res. 28, 541-551.

Washietl, S., Kellis, M. & Garber, M. Evolutionary dynamics and tissue specificity of human long noncoding RNAs in six mammals. *Genome Res.* 24, 616-628, doi:10.1101/gr.165035.113 (2014). PMCID:3975061.

Weinberger, E. D. (1991). Fourier and Taylor series on fitness landscapes. Biol. Cybern. 65, 321-330.

Wong, A. S. L., Choi, G. C. G., Cui, C. H., Pregernig, G., Milani, P., Adam, M., Perli, S. D., Kazer, S. W., Gaillard, A., Hermann, M., et al. (2016). Multiplexed barcoded CRISPR-Cas9 screening enabled by CombiGEM. Proc. Natl. Acad. Sci. 113, 2544-2549.

Wu, C., Yosef, N., Thalhamer, T., Zhu, C., Xiao, S., Kishi, Y., Regev, A. & Kuchroo, V. K. Induction of pathogenic TH17 cells by inducible salt-sensing kinase SGK1. *Nature.* 496, 513-517, doi:10.1038/nature11984 (2013). PMCID:3637879.

Yosef, N., and Regev, A. (2016). Writ large: Genomic dissection of the effect of cellular environment on immune response. Science (80-.). 354, 64-68.

Yosef, N., Shalek, A. K., Gaublomme, J. T., Jin, H., Lee, Y., Awasthi, A., Wu, C., Karwacz, K., Xiao, S., Jorgolli, M., Gennert, D., Satija, R., Shakya, A., Lu, D. Y., Trombetta, J. J., Pillai, M. R., Ratcliffe, P. J., Coleman, M. L., Bix, M., Tantin, D., Park, H., Kuchroo, V. K. & Regev, A. Dynamic regulatory network controlling TH17 cell differentiation. *Nature.* 496, 461-468, doi:10.1038/nature11981 (2013). PMCID:3637864.

Yu, C., Mannan, A. M., Yvone, G. M., Ross, K. N., Zhang, Y.-L., Marton, M. A., Taylor, B. R., Crenshaw, A., Gould, J. Z., Tamayo, P., et al. (2016). High-throughput identification of genotype-specific cancer vulnerabilities in mixtures of barcoded tumor cell lines. Nat. Biotechnol. 34, 419-423.

Zalatan, J. G., Lee, M. E., Almeida, R., Gilbert, L. A., Whitehead, E. H., La Russa, M., Tsai, J. C., Weissman, J. S., Dueber, J. E., Qi, L. S., et al. (2015). Engineering Complex Synthetic Transcriptional Programs with CRISPR RNA Scaffolds. Cell 160, 339-350.

Zetsche, B., Gootenberg, J. S., Abudayyeh, O. O., Slaymaker, I. M., Makarova, K. S., Essletzbichler, P., Volz, S. E., Joung, J., van der Oost, J., Regev, A., et al. (2015). Cpf1 Is a Single RNA-Guided Endonuclease of a Class 2 CRISPR-Cas System. Cell 163, 759-771.

Zetsche, B., Heidenreich, M., Mohanraju, P., Fedorova, I., Kneppers, J., DeGennaro, E. M., Winblad, N., Choudhury, S. R., Abudayyeh, O. O., Gootenberg, J. S., et al 2016, "Multiplex gene editing by CRISPR-Cpf1 through autonomous processing of a single crRNA array", bioRxiv.

Zhang, X., Liu, Q., Luo, C., Deng, Y., Cui, K. & Shi, D. 2014, "Identification and characterization of buffalo 7SK and U6 pol III promoters and application for expression of short hairpin RNAs", *International Journal of Molecular Sciences*, vol. 15, no. 2, pp. 2596-2607.

Zheng, G. X. Y., Terry, J. M., Belgrader, P., Ryvkin, P., Bent, Z. W., Wilson, R., Ziraldo, S. B., Wheeler, T. D., McDermott, G. P., Zhu, J., et al 2016, "Massively parallel digital transcriptional profiling of single cells", bioRxiv,.

Zuk, O., Hechter, E., Sunyaev, S. R., and Lander, E. S. (2012). The mystery of missing heritability: Genetic interactions create phantom heritability. Proc. Natl. Acad. Sci. U.S.A. 109, 1193-1198.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of multiplexing samples for single cell or nuclei sequencing comprising:
   a) labeling single cells or nuclei from each of a plurality of samples with a sample barcode oligonucleotide unique to each sample, wherein the cells or nuclei are labeled by a method comprising labeling primary amines or thiols of membrane proteins with a functional group and binding or linking the sample barcode oligonucleotides to the functional group through a complementary molecule or functional group; and
   b) constructing a multiplexed single cell or nuclei sequencing library for the plurality of samples comprising cell of origin barcodes, wherein the sample barcode oligonucleotide on each labeled cell or nuclei receives a cell of origin barcode.

2. The method according to claim 1, further comprising sequencing the library and demultiplexing in silico based on the cell of origin barcodes and the sample barcodes.

3. The method according to claim 1, wherein the single cells or nuclei are functionalized on primary amines with biotin and the cells or nuclei are labeled with antibodies specific to biotin linked to the sample barcode oligonucleotide, preferably; or
   wherein the single cells or nuclei functionalized on primary amines or thiols with an acceptor molecule capable of being covalently linked to the sample barcode oligonucleotide by click chemistry and wherein the cells or nuclei are labeled with sample barcode oligonucleotides modified for click chemistry; or
   wherein the single cells or nuclei are functionalized on primary amines with a biotin moiety and the sample barcode oligonucleotide comprises avidin, whereby the cells or nuclei are labeled by biotin-avidin binding.

4. The method according to claim 1, wherein constructing a single cell or nuclei sequencing library comprises sorting cells or nuclei into individual discrete volumes, each volume comprising cell of origin barcodes specific to the volume, optionally, wherein the individual discrete volumes are droplets, microfluidic chambers, microwells, or wells; or
wherein constructing a single cell or nuclei sequencing library comprises split and pool barcoding.

5. The method according to claim 1, wherein the multiplexed single cell or nuclei sequencing library is an RNA sequencing library; or
wherein the multiplexed single cell or nuclei sequencing library is an Assay for Transposase-Accessible Chromatin using sequencing (ATAC-seq) library; or
wherein the multiplexed single cell or nuclei sequencing library provides a proteomics readout; or
wherein the multiplexed single cell or nuclei sequencing library provides a targeted gene expression readout, wherein specific genes are targeted with a probe capable of being labeled with the sample barcode.

6. The method according to claim 1, wherein the multiplexed single cell or nuclei sequencing library provides a readout comprising transcriptome, ATAC, proteomic, targeted gene expression, or any combination thereof.

7. The method according to claim 1, further comprising sequencing the library and defining each cell barcode as a singlet, doublet, or unknown by applying an algorithm that calculates the probability that a sample barcode detected with a cell barcode was due to background or a sample, wherein if a cell barcode is associated with two sample barcodes and the probability of background is low the cell barcode is associated with a doublet.

8. The method according to claim 7, wherein only singlets are analyzed.

9. A method of multiplexing samples for single nuclei sequencing comprising:
a) labeling single nuclei from each of a plurality of samples with one or more antibodies conjugated to a sample barcode oligonucleotide that is unique to each sample, wherein the labeling is performed in a Tris based buffer comprising Tris, a detergent, a blocking protein, and one or more salts; and
b) constructing a multiplexed single nuclei sequencing library for the plurality of samples comprising cell of origin barcodes, wherein the sample barcode oligonucleotide on each labeled nuclei receives a cell of origin barcode.

10. The method according to claim 9, wherein the single nuclei are obtained from a population of cells, fresh tissue, frozen tissue or fixed formalin paraffin embedded (FFPE) tissues.

11. The method according to claim 9, further comprising sequencing the library and demultiplexing in silico based on the cell of origin barcodes and the sample barcodes.

12. The method according to claim 9,
wherein the one or more antibodies are specific for one or more proteins present on the nuclear membrane of the single nuclei in the plurality of samples, or wherein the one or more antibodies are specific for one or more nuclear pore proteins; and
optionally wherein the one or more antibodies are selected from the group consisting of Lamin-A, Lamin-B, Lamin-C, NUP98, NUP153, and NUP214.

13. The method according to claim 9, wherein constructing a single nuclei sequencing library comprises sorting nuclei into individual discrete volumes, each volume comprising cell of origin barcodes specific to the volume, optionally, wherein the individual discrete volumes are droplets, microfluidic chambers, microwells, or wells; or
wherein constructing a single nuclei sequencing library comprises split and pool barcoding.

14. The method according to claim 9, wherein the multiplexed single nuclei sequencing library is an RNA sequencing library; or
wherein the multiplexed single nuclei sequencing library is an ATAC sequencing library; or
wherein the multiplexed single nuclei sequencing library provides a proteomics readout; or
wherein the multiplexed single nuclei sequencing library provides a targeted gene expression readout, wherein specific genes are targeted with a probe capable of being labeled with the sample barcode.

15. The method according to claim 9, wherein the multiplexed single nuclei sequencing library provides a readout comprising transcriptome, ATAC, proteomic, targeted gene expression, or any combination thereof.

16. The method according to claim 9, further comprising sequencing the library and defining each cell barcode as a singlet, doublet, or unknown by applying an algorithm that calculates the probability that a sample barcode detected with a cell barcode was due to background or a sample, wherein if a cell barcode is associated with two sample barcodes and the probability of background is low the cell barcode is associated with a doublet.

17. The method according to claim 16, wherein only singlets are analyzed.

18. The method according to claim 9, further comprising enriching for nuclei expressing one or more genes of interest, and optionally wherein nuclei are stained with fluorescent RNA probes specific for the one or more genes of interest and enriched by FACS.

19. The method of claim 9, wherein nuclei are labeled in a buffer comprising BSA, Tween-20, Tris, and NaCl.

20. The method of claim 19, wherein nuclei are labeled in a buffer comprising about 2% BSA, 0.02% Tween-20, 10 mM Tris, and 146 mM NaCl.

21. The method of claim 20, wherein nuclei are labeled in a buffer comprising about 2% BSA, 0.02% Tween-20, 10 mM Tris, 146 mM NaCl, 1 mM $CaCl_2$), and 21 mM $MgCl_2$.

* * * * *

UNITED STATES PATENT AND TRADEMARK OFFICE
CERTIFICATE OF CORRECTION

PATENT NO. : 11,332,736 B2
APPLICATION NO. : 16/770380
DATED : May 17, 2022
INVENTOR(S) : Aviv Regev et al.

It is certified that error appears in the above-identified patent and that said Letters Patent is hereby corrected as shown below:

In the Specification

In Column 14, Line 20, delete "1-Nrp," and insert -- 1, NRP, --.

In Column 15, Line 7, delete "NETS" and insert -- NHS --.

In Column 33, Line 36, delete "SILEX" and insert -- SELEX --.

In Column 33, Line 42, delete "oligonucleotide;" and insert -- oligonucleotides --.

In Column 33, Line 61, after "O-alkyl," insert -- O-allyl, --.

In Column 33, Line 61, after "S-alkyl," insert -- S-allyl, --.

In Column 41, Line 50, delete "$^{131}$I)" and insert -- $^{131}$I), --.

In Column 61, Line 51, delete "~80° C." and insert -- -80° C. --.

In Columns 65-66, Line 23 (Table 1), delete "GLE" and insert -- CJGLE --.

In Column 70, Line 34, delete "Supernatant" and insert -- supernatant --.

In Column 87, Line 29, delete "L. S" and insert -- L. S., --.

In Column 88, Line 62, delete "al2016," and insert -- al 2016, --.

In Column 92, Line 10, delete "Raj e," and insert -- Raje, --.

Signed and Sealed this
Twentieth Day of June, 2023

Katherine Kelly Vidal
*Director of the United States Patent and Trademark Office*

CERTIFICATE OF CORRECTION (continued)
U.S. Pat. No. 11,332,736 B2

In the Claims

In Column 104, Lines 58-59, in Claim 3, delete "oligonucleotide, preferably;" and insert -- oligonucleotide; --.

In Column 104, Line 60, in Claim 3, after "nuclei" insert -- are --.

In Column 106, Line 55, in Claim 21, delete "$CaCl_2$)," insert -- $CaCl_2$, --.